United States Patent [19]

Shibayama et al.

[11] Patent Number: 5,683,998
[45] Date of Patent: Nov. 4, 1997

[54] TRICYCLIC TRIAZOLO DERIVATIVES, PROCESSES FOR PRODUCING THE SAME AND THE USES OF THE SAME

[75] Inventors: Katsuhiro Shibayama, Kounan; Tetsuya Makino, Kamakura; Takayuki Imaoka, Kamakura; Tetsuya Katou, Kamakura; Masayuki Kaneko, Yokohama, all of Japan

[73] Assignee: Toray Industries, Inc., Tokyo, Japan

[21] Appl. No.: 432,714

[22] Filed: May 2, 1995

Related U.S. Application Data

[63] Continuation of Ser. No. 960,417, filed as PCT/JP92/00523, Apr. 23, 1992, abandoned.

[30] Foreign Application Priority Data

| Apr. 23, 1991 | [JP] | Japan | 3-091961 |
| Jun. 20, 1991 | [JP] | Japan | 3-148804 |
| Dec. 11, 1991 | [JP] | Japan | 3-327541 |
| Jan. 16, 1992 | [JP] | Japan | 4-005741 |

[51] Int. Cl.$^6$ ............ A61K 31/495; C07D 519/00; C07D 487/04; C07D 243/12
[52] U.S. Cl. ............ 514/218; 514/250; 540/499; 540/506; 540/558; 540/575; 544/354; 544/346; 544/370; 546/192; 546/194; 546/199; 546/214; 546/225; 546/232; 546/241; 548/262.4; 548/306.4; 548/310.1; 560/22; 564/441; 564/442
[58] Field of Search ............ 514/250, 218; 544/346; 540/575

[56] References Cited

U.S. PATENT DOCUMENTS

| 4,464,373 | 8/1984 | Barnes | 544/346 |
| 4,668,678 | 5/1987 | Brown et al. | 544/346 |
| 5,116,841 | 5/1992 | Watjen | 544/346 |

FOREIGN PATENT DOCUMENTS

| 0 240 899 | 10/1987 | European Pat. Off. |
| 49-125395 | 11/1974 | Japan |
| 2-256681 | 10/1990 | Japan |
| 3-149543 | 6/1991 | Japan |

OTHER PUBLICATIONS

Derwent Abstract for JP2-256681 (1990).

*Primary Examiner*—Mark L. Berch
*Attorney, Agent, or Firm*—Birch, Stewart, Kolasch & Birch, LLP

[57] ABSTRACT

Novel tricyclic triazolo derivatives and pharmaceutically acceptable salts thereof, which are useful as anti-inflammation agents, anti-allergy agents or anti-PAF agents as well as processes for producing the same are disclosed. The triazolo derivatives of the present invention are represented by the formula (I):

[wherein $R^1$ represents hydrogen, lower alkyl or $C_3$–$C_5$ cycloalkyl; $R^2$ and $R^3$ respectively represent hydrogen, lower alkyl, lower alkoxy or halogen; W represents C=O or $CR^4R^5$ (wherein $R^4$ and $R^5$ respectively represents hydrogen or lower alkyl); A represents $C_1$–$C_5$ straight or branched saturated or unsaturated alkylene which may contain one or more hetero atoms; l represents 0 to 2, n represents 1 to 3, ... represents single bond or double bond; Y represents N or C; Z represents $C(B)Ar^1Ar^2$ (wherein B represents hydrogen, hydroxy or methoxy, $Ar^1$ and $Ar^2$ respectively represent hydrogen or substituted or non-substituted aryl), $CAr^1Ar^2$ (wherein $Ar^1$ and $Ar^2$ represent the same meanings as mentioned above), O—$CHAr^1Ar^2$ (wherein $Ar^1$ and $Ar^2$ represent the same meanings as mentioned above) or condensed aromatic ring].

16 Claims, No Drawings

TRICYCLIC TRIAZOLO DERIVATIVES, PROCESSES FOR PRODUCING THE SAME AND THE USES OF THE SAME

This application is a continuation of application Ser. No. 07/960,417 filed as PCT/JP92/00523 on Apr. 23, 1992, now abandoned.

TECHNICAL FIELD

This invention relates to novel tricyclic triazolo derivatives useful as anti-inflammatories and antiallergics, which strongly antagonize the actions of platelet activating factor (hereinafter referred to as "PAF") and which also have antihistaminic property, as well as to processes for producing the same and uses of the same.

BACKGROUND ART

In recent years, PAF is strongly drawing attention and its relevancy to various diseases is being revealed. That is, it is assumed that PAF relates to inflammation, allergic diseases, anaphylaxis shock, septic shock, DIC, endotoxin shock, diseases of cardiac muscle, asthma, lung edema, alimentary canal ulcers, nephritis, hepatitis and rejection after transplantation [see Extra Number of Modern Chemistry 17, Platelet Activating Factor—Biochemistry.Physiology.Pathology-, Keizo WAKU, Keizo INOUE ed., published by Tokyo Kagaku Dojin]. Thus, it is expected that a compound which antagonizes the actions of PAF exhibits therapeutic effects for the above-mentioned diseases and other diseases in which it is desired to antagonize PAF.

In fact, by administration of a PAF-antagonist, the Arthus reaction of mouse which is a model of inflammation reaction was suppressed. Thus, it was shown that PAF is related to inflammation reaction (Jpn. J. Pharmacol., 46, 55P (1988)).

On the other hand, it is known that chemical mediators other than PAF, such as histamine and leukotriene are released from various cells as a result of antigen-antibody reactions. Therefore, it is expected that a compound which has an antagonistic property to PAF and antihistaminic property exhibits stronger antiallergic effects than a PAF antagonist alone or than an antihistaminic alone.

To date, thienotriazolo-1,4-diazepine-based compounds are known as anti-PAF agents (Japanese Laid-open Patent Application (Kokai) Nos. 61-176591, 2-256681 and 2-256682). As a compound having both antihistaminic property and antagonistic property to PAF, only benzocycloheptapyridine-based compound is known (EP 270818).

Although triazoloquinoxaline derivatives are known, it has only been reported that they have antianxiety property [J. Heterocyclic Chem. 27, 691 (1990)].

On the other hand, a triazolobenzimidazol compound of the following formula has been reported to have anti-bacterial property (Pestic. Sci., 29, 143 (1990)).

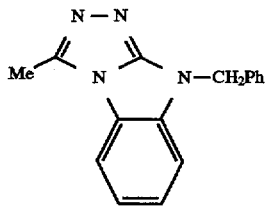

The compound of the following formula is one whose production process is known (J. Heterocycl. Chem., 15, 1027 (1978)).

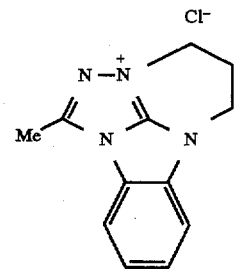

However, it has not been reported that these compounds have anti-PAF properties or antiallergic properties.

DISCLOSURE OF THE INVENTION

A novel and useful anti-PAF agent is expected to have prophylactic and therapeutic effects against wide variety of diseases, and is desired. Further, an antiallergic which has antihistaminic property in addition to anti-PAF property is expected to have prophylactic and therapeutic effects against allergic and inflammation diseases, and is desired.

An object of the present invention is to provide a novel tricyclic triazolo derivative which has both the antagonistic property to PAF and antihistaminic property and so useful as an anti-inflammatory, antiallergic and anti-PAF agent, as well as pharmaceutically acceptable salts thereof. Another object of the present invention is to provide intermediates useful for the tricyclic triazolo derivative. Still another object of the present invention is to provide a process for producing the triazolo derivative according to the present invention.

The present invention provides a novel tricyclic triazolo derivative of the formula (I):

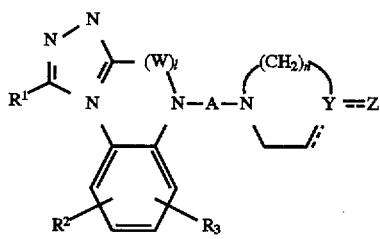

[wherein $R^1$ represents hydrogen, lower alkyl or $C_3$–$C_5$ cycloalkyl; $R^2$ and $R^3$ respectively represent hydrogen, lower alkyl, lower alkoxy or halogen; W represents C=O or $CR^4R^5$ (wherein $R^4$ and $R^5$ respectively represents hydrogen or lower alkyl); A represents $C_1$–$C_5$ straight or branched saturated or unsaturated alkylene which may contain one or more hetero atoms; l represents 0 to 2, n represents 1 to 3, ... represents single bond or double bond; Y represents N or C; Z represents $C(B)Ar^1Ar^2$ (wherein B represents hydrogen, hydroxy or methoxy, $Ar^1$ and $Ar^2$ respectively represent hydrogen or substituted or non-substituted aryl), $CAr^1Ar^2$ (wherein $Ar^1$ and $Ar^2$ represent the same meanings as mentioned above), O—$CHAr^1Ar^2$ (wherein $Ar^1$ and $Ar^2$ represent the same meanings as mentioned above) or condensed aromatic ring] and pharmaceutically acceptable salts thereof, as well as an anti-inflammatory, an antiallergic and an anti-PAF agent comprising the triazolo derivative or a pharmaceutically acceptable salt thereof as an effective ingredient. Further, the present invention provides a dihydrotriazolo quinoxaline derivative of the formula II:

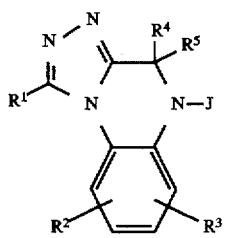

(II)

(wherein $R^1$, $R^2$, $R^3$, $R^4$ and $R^5$ represent the same meanings as mentioned above; J represents hydrogen or —A—B (wherein B represents halogen, —$OR^{10}$ (wherein $R^{10}$ represents a protective group for alcohol) or —$CO_2L$ (wherein L represents hydrogen or lower alkyl); and A represents the same meanings as mentioned above).

By the present invention, novel triazolo derivatives which have both antihistaminic properties and antagonistic effects to PAF, which are useful as antiallergics, anti-inflammatories and anti-PAF agents were provided. The derivatives and pharmaceutically acceptable salts thereof according to the present invention are expected to have prophylactic and therapeutic effects against various diseases in which histamine and PAF play roles, in addition to the above-mentioned diseases. In particular, they can be used as antiasthmatics, lenitives for shocks and as therapeutic agents for thrombosis.

In the definitions of the above-mentioned symbols, halogen means fluorine, chlorine, bromine and iodine; and lower alkyl and the alkyl moiety of lower alkoxy mean $C_1$–$C_6$ straight or branched alkyl such as methyl, ethyl, n-propyl, isopropyl, n-butyl, isobutyl, t-butyl, n-pentyl and n-hexyl. Among these, preferred groups are methyl and ethyl groups. In the definition of A, $C_1$–$C_5$ straight or branched saturated or unsaturated alkylene means, for example, methylene, ethylene, trimethylene, tetramethylene, pentamethylene, methylethylene, ethylethylene, methyltrimethylene, ethyltrimethylene, methyltetramethylene or the following structures:

—$CH_2$—CH=CH—  —$CH_2$—CH=CH—$CH_2$—
—$CH_2$—C≡C—  —$CH_2$—C≡C—$CH_2$—
—$CH_2OCH_2CH_2$—  —$CH_2CH_2OCH_2CH_2$—
—$CH_2CH(OH)CH_2$—

In the definition of Z, $Ar^1$ and $Ar^2$ mean, when they are aromatic hydrocarbons, $C_6$–$C_{10}$ aryl such as phenyl and naphthyl, and when they are heterocyclic rings, they mean, for example, furyl, thienyl, pyridyl, pyrimidinyl, oxazolyl, isoxazolyl, thiazolyl, isothiazolyl, imidazolyl, pyrazolyl or benzofuranyl, and include condensed heterocyclic rings such as benzofuranyl, benzothienyl, indolyl, quinolyl and isoquinolyl. In the above-described definitions, the substituents in every group means, the same or different, substituent groups selected from the group consisting of $C_1$–$C_6$ alkyl, $C_1$–$C_6$ alkoxy, acyl, sulfonyl, halogen, halogenated alkyl, alkylamino, nitro, cyano, hydroxy, mercapto and alkylthio groups, the number of substituent groups on an aromatic ring being 1–3. Thus, substituted aryl means, for example, 4-chlorophenyl, 4-bromophenyl, 4-fluorophenyl, 4-methylphenyl, 4-methoxyphenyl, 4-trifluoromethylphenyl, 3-chlorophenyl, 3-bromophenyl, 3-fluorophenyl, 3-methylphenyl, 3-methoxyphenyl, 3-trifluoromethylphenyl, 2-chlorophenyl, 2-bromophenyl, 2-fluorophenyl, 2-methylphenyl, 2-methoxyphenyl, 2-trifluoromethylphenyl, 2,3-dichlorophenyl, 3,4-dichlorophenyl, 2,3-dimethoxyphenyl, 3,4-dimethoxyphenyl, 3,4,5-trimethoxyphenyl, 5-methyl-2-thienyl, 5-methyl-3-thienyl, 5-methyl-4-thienyl, 5-methyl-2-pyridyl, 5-methyl-3-pyridyl, 5-methyl-4-pyridyl and the like. Substituted or non-substituted aralkyl means, for example, benzyl, 4-fluorobenzyl, 4-chlorobenzyl, 2-thienylmethyl, 2-furylmethyl and the like, preferably 4-fluorobenzyl. Condensed aromatic ring means, for example, naphthalene, quinoline, benzimidazole, benzofuran, benzothiophen, benzisoxazole, benzthiazole, imidazopyridine and the like. Preferred substituents are shown as follows:

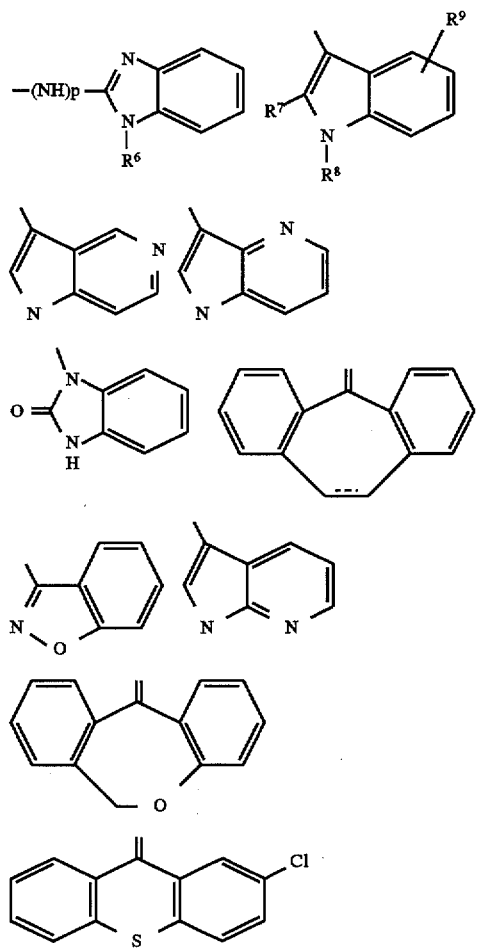

wherein $R^6$ represents substituted or non-substituted aralkyl or alkoxyalkyl; p represents 0 or 1, $R^7$ and $R^8$ respectively represents hydrogen or lower alkyl, $R^9$ represents hydrogen, lower alkyl, lower alkoxy or halogen; ___ represents single bond or double bond.

Alkoxyalkyl means, for example, ethoxyethyl, methoxyethyl, methoxypropyl and the like, and preferably ethoxyethyl. Examples of the protective group for alcohol represented by $R^{10}$ include lower alkyl such as methyl, ethyl and isopropyl, benzyl, tetrahydropyranyl, methoxymethyl, methylthiomethyl and the like.

The pharmaceutically acceptable salts of the compound of the formula (I) include inorganic acid salts such as hydrochloric acid salt, hydrobromic acid salt, sulfuric acid salt, boric acid salt and phosphoric acid salt; organic acid salts such as acetic acid salt, maleic acid salt, fumaric acid salt, tartaric acid salt, succinic acid salt, malic acid salt, lactic acid salt, citric acid salt, malonic acid salt, benzoic acid salt and paratoluene sulfonic acid salt; and addition salts of amino acids such as lysine, glycine, phenylalanine and glutamic acid.

Processes for producing the compound of the formula (I) will now be described. It should be noted, however, the production processes are not limited thereto, and the reaction conditions are appropriately selected from those described hereinafter in each production process.

The compound of the formula (I) according to the present invention may be produced by reacting the compound of the formula (XVII):

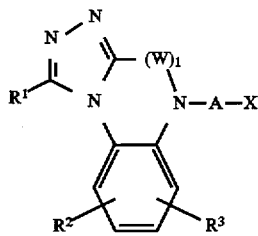

(XVII)

(wherein X represents a halogen atom, and $R^1$, $R^2$, $R^3$, A, W and l represent the same meanings as mentioned above) or an acid addition salt thereof with a compound of the formula (IV):

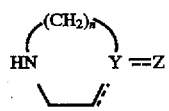

(IV)

(wherein Y, Z, n and ⋯ represent the same meanings as mentioned above) or an acid addition salt thereof (inorganic acid salts such as hydrochloric acid salt and sulfuric acid salt; and organic acid salts such as acetic acid salt), the compound of the formula (XVII) being produced by reacting a compound of the formula (III):

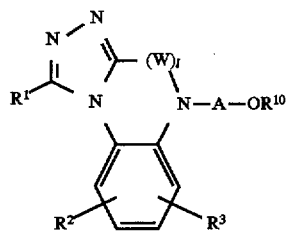

(III)

(wherein $R^1$, $R^2$, $R^3$, $R^{10}$, A, W and l represent the same meanings as mentioned above) with a hydrogen halide solution.

In this process, the hydrogen halide solution may be aqueous hydrobromic acid, hydrogen bromide-acetic acid solution, concentrated hydrochloric acid and the like. The reaction between the compound of the formula (III) and the hydrogen halide solution may usually be carried out at 30° C. to the boiling point of the solvent used for 10 minutes to 1 week. The produced compound of the formula (XVII) may be obtained by adding aqueous solution of sodium hydroxide, potassium carbonate, sodium carbonate, sodium hydrogen carbonate or the like and by extracting the resultant with an organic solvent. Alternatively, after the reaction, the solvent may be evaporated to dryness and the compound may be used as an acid addition salt in the subsequent reaction.

The reaction between the compound of the formula (XVII) or an acid addition salt thereof with a compound of the formula (IV) or an acid addition salt thereof may usually be carried out in a solvent inert to the reaction (such as dimethylformamide, dimethylacetamide, 2-butanone, ethanol, n-butanol, tetrahydrofuran and dichloromethane as well as mixed solvents thereof) for 10 minutes to 1 week. The reaction temperature may preferably be 0°–150° C. To increase the reaction rate, an organic base such as triethylamine or pyridine; or an inorganic base such as potassium carbonate, sodium carbonate, sodium hydrogen carbonate, calcium hydride, potassium iodide or potassium acetate may be employed as a catalyst.

The compound of the formula (I) may also be produced by using a compound of the formula (V) as a material according to the following process. That is, the compound of the formula (I) may be obtained by reacting the compound of the formula (V):

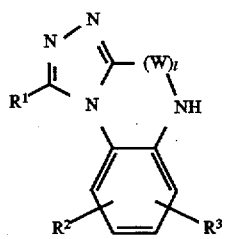

(V)

(wherein $R^1$, $R^2$, $R^3$, W and l represent the same meanings as mentioned above)

with a compound of the formula (VI):

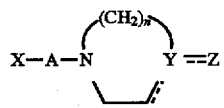

(VI)

(wherein X represents a halogen atom, and A, Y, Z, n and ⋯ represent the same meanings as mentioned above).

The reaction may be carried out in a solvent inert to the reaction (such as dimethylformamide, dimethylacetamide, tetrahydrofuran and dioxane) in the presence of an inorganic base (such as sodium hydride, calcium hydride, sodium amide and potassium hydroxide or an organic base (such as pyridine, potassium t-butoxide, and triethylamine) at 0° C. to the refluxing temperature of the employed solvent for 5 minutes to 5 hours.

The compound of the formula (I) may also be produced by using a compound of the formula (XVIII) according to the following method.

That is, a compound of the formula (XIXa):

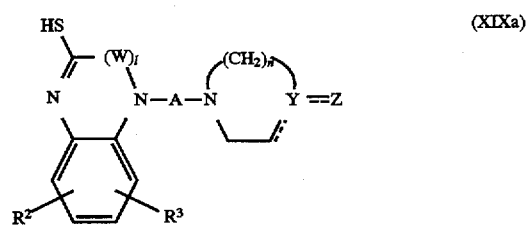

(XIXa)

(wherein $R^2$, $R^3$, A, W, Y, Z, l, n, ⋯ represent the same meanings as mentioned above)

is obtained by reacting a compound of the formula (XVIII):

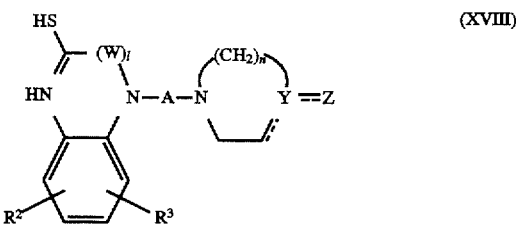

(wherein $R^2$, $R^3$, A, W, Y, Z, l, n, ... represent the same meanings as mentioned above)
with a reagent to give thione, such as phosphorus pentasulfide or Lawesson's Reagent (trademark). This reaction may usually be carried out in a solvent inert to the reaction (such as pyridine, acetonitrile, toluene, xylene, tetrahydrofuran, chloroform, dioxane, diethyl ether and Diglyme) at 30°–100° C. for 1 minutes to 5 hours.

Alternatively, a compound of the formula (XIXb):

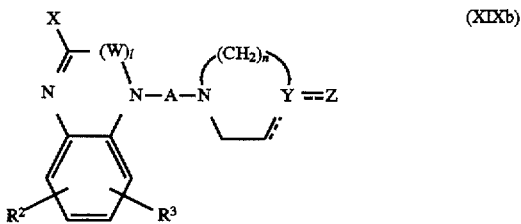

(wherein X represents a halogen atom, and $R^2$, $R^3$, A, W, Y, Z, l, n, ... represent the same meanings as mentioned above) is obtained by reacting the compound of the formula (XVIII) with a halogenating agent. Examples of the halogenating agent include phosphorus oxychloride, thionyl chloride, phosphorus trichloride and the like, as well as thionyl chloride-dimethylformamide, phosphorus oxychloride-N-methylformanilide and the like. The reaction may be carried out in an inert solvent (such as benzene, toluene, xylene, chloroform or the like) at 0° C. to the refluxing temperature of the employed solvent for 5 minutes to 6 hours.

Alternatively, a compound of the formula (XIXc):

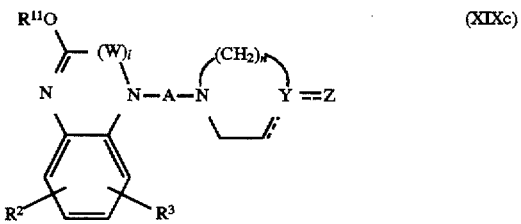

(wherein $R^{11}$ represents a lower alkyl group, and $R^2$ $R^3$, A, W, Y, Z, l, n, ... represent the same meanings as mentioned above)
is obtained by reacting the compound of the formula (XVIII) with an alkylating agent. Examples of the alkylating agent include trialkyloxoniumtetrafluoro borate, dialkyl sulfate and the like.

The compound of the formula (I) may be obtained by reacting the compound represented by the formula (XIXa), (XIXb) or (XIXc) obtained as mentioned above with a compound of the formula (VIII):

$$R^1CONHNH_2 \qquad (VIII)$$

(wherein $R^1$ represents the same meanings as mentioned above)

in a solvent inert to the reaction (such as xylene, n-butanol, n-hexanol, acetonitrile and cyclohexane) at 50° C. to the refluxing temperature of the employed solvent for 30 minutes to 6 hours. To increase the reaction rate, the reaction may be carried out in the presence of an organic acid (such as acetic acid or propionic acid), an inorganic acid (such as hydrochloric acid or sulfuric acid) or silica gel.

Alternatively, the compound represented by the formula (XIXa), (XIXb) or (XIXc) is reacted with hydrazine in a solvent inert to the reaction (such as methanol, ethanol, n-propanol or n-butanol) at 0°–50° C. for 5 minutes to 3 hours to obtain a compound of the formula (XX):

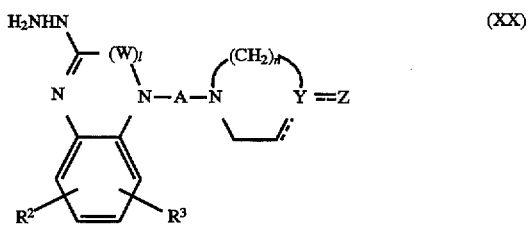

(wherein $R^2$ $R^3$ A, W, Y, Z, l n, ... represents the same meanings as mentioned above), and the compound of the formula (I) may be obtained by reacting this compound of the formula (XX) with a compound of the formula (X):

$$R^1C(OR^{12})_3 \qquad (X)$$

(wherein $R^{12}$ represents a lower alkyl group and $R^1$ represents the same meanings as mentioned above) or with a compound of the formula (XI):

$$R^1CO_2H \qquad (XI)$$

(wherein $R^1$ represents the same meanings as mentioned above)
or a reactive derivative thereof in a solvent inert to the reaction (such as toluene, xylene, methanol, ethanol, n-butanol, acetonitrile or dioxane) at 0° C. to the refluxing temperature of the employed solvent for 10 minutes to 8 hours. In this reaction, to increase the reaction rate, the reaction may be carried out in the presence of an organic acid (such as acetic acid and propionic acid), an inorganic acid (such as hydrochloric acid or sulfuric acid) or silica gel.

Among the compounds represented by the formula (I), the compound of the formula (Ib):

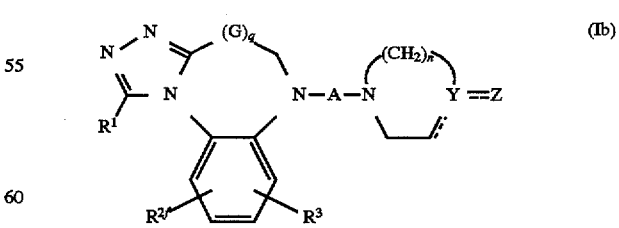

(wherein G represents $CR^4R^5$, q represents 0 or 1, and $R^1$, $R^2$, $R^3$, $R^4$, $R^5$, A, Y, Z, n, ... represent the same meanings as mentioned above)
may be produced by reacting a compound of the formula (XII):

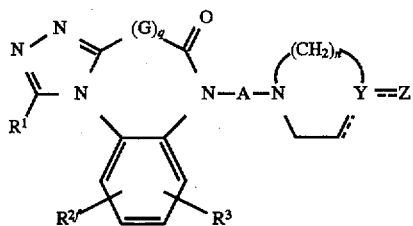
(XII)

(wherein $R^1$, $R^2$, $R^3$, A, G, Y, Z, n, q, ___ represent the same meanings as mentioned above)
with a reducing agent.

Examples of the reducing agent employed in the reaction include lithium aluminum hydride, aluminum hydride, borane, sodium borohydride, lithium borohydride and the like. The reaction temperature may be 0° C. to the refluxing temperature of the solvent, and the reaction time may be 5 minutes to 6 hours.

Among the compounds represented by the formula (I), the compound of the formula (Ic):

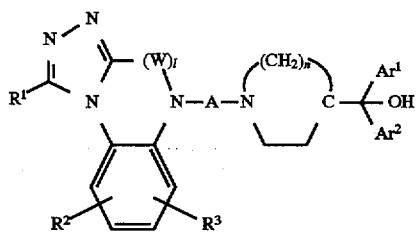
(Ic)

(wherein $R^1$, $R^2$, $R^3$, $Ar^1$, $Ar^2$, A, W, l and n represent the same meanings as mentioned above)
may be produced by reacting a compound of the formula (XIII):

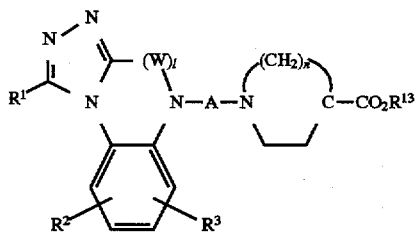
(XIII)

(wherein $R^{13}$ represents lower alkyl, and $R^1 R^2 R^3$, A, W, l and n represent the same meanings as mentioned above)
or a compound of the formula (XIV):

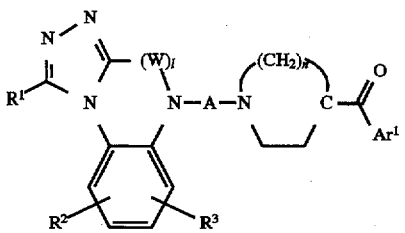
(XIV)

(wherein $Ar^1$, $R^1$, $R^2$, $R^3$, A, W, l and n represent the same meanings as mentioned above)
with a compound of the formula (XV):

ArMgX  (XV)

(wherein X represents a halogen atom, Ar represents $Ar^1$ and/or $Ar^2$ (wherein $Ar^1$ and $Ar^2$ represent the same meanings as mentioned above))

or with a compound of the formula (XVI):

ArLi  (XVI)

(wherein Ar represents $Ar^1$ and/or $Ar^2$ (wherein $Ar^1$ and $Ar^2$ represent the same meanings as mentioned above)).

The reaction may be carried out in a solvent inert to the reaction (such as diethyl ether and tetrahydrofuran) at −78° C. to the refluxing temperature of the employed solvent for 5 minutes to 10 hours.

The compound of the formula (Id):

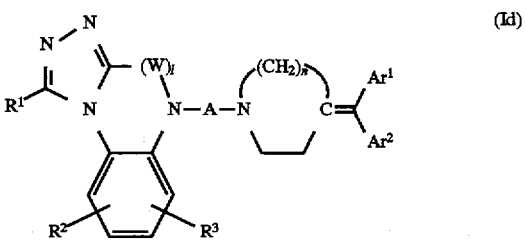
(Id)

(wherein $R^1$, $R^2$, $R^3$, $Ar^1$, $Ar^2$, A, W, l and n represent the same meanings as mentioned above)

may be produced by dehydrating the compound of the formula (Ic).

As the dehydrating agent, strong acids such as concentrated hydrochloric acid and concentrated sulfuric acid, and dehydrating agents such as thionyl chloride may be used. The reaction may be carried out at 0°–100° C. for 5 minutes to 5 hours.

The compound represented by the formula (XIII) or (XIV), which are used as starting materials in the above-described reaction may be produced by the following reaction steps.

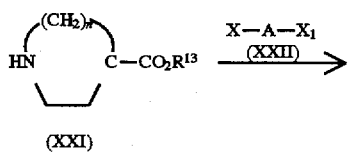

(XXI)

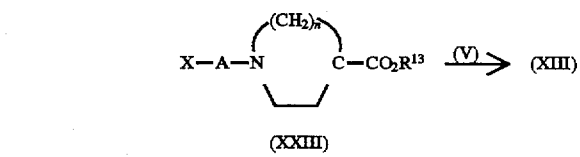
(XIII)

(XXIII)

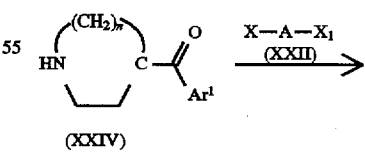

(XXIV)

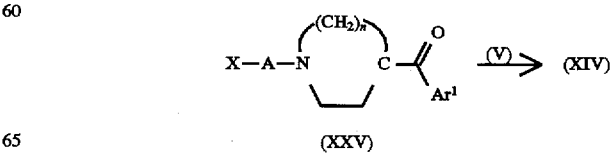
(XIV)

(XXV)

By reacting a compound of the formula (XXI):

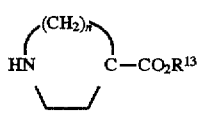
(XXI)

(wherein $R^{13}$ and n represent the same meanings as mentioned above)
with a compound of the formula (XXII):

(XXII)

(wherein A represents the same meanings as mentioned above, X and $X_1$, the same or different, represent halogen), the compound of the formula (XXIII):

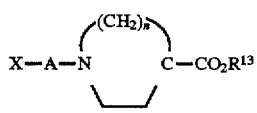
(XXIII)

(wherein A, X, $R^{13}$ and n represent the above-mentioned meanings) is obtained. Then the compound of the formula (XIII) is obtained by reacting a compound of the formula (XXIII) with the compound of the formula (V).

The reaction between the compound of the formula (XXI) and the compound of the formula (XXII) may be carried out in a solvent inert to the reaction (such as dimethylformamide, dimethylacetamide, 2-butanone, ethanol, n-butanol, tetrahydrofuran or dichloromethane, or a mixture thereof) at 0°–150° C. for 10 minutes to 1 week. It is preferred to add an organic base such as triethylamine, potassium acetate, or pyridine, or an inorganic base such as potassium carbonate, sodium carbonate, sodium hydrogen carbonate, calcium hydride or, potassium iodide as a catalyst.

The reaction between the compound of the formula (XXIII) and the compound of the formula (V) may be carried out in a solvent inert to the reaction (such as dimethylformamide, dimethylacetamide, tetrahydrofuran or dioxane) in the presence of an inorganic base (such as sodium hydride, calcium hydride, sodium amide or, potassium hydroxide) or an organic base (such as pyridine, potassium t-butoxide, or triethylamine) at 0° C. to the refluxing temperature of the solvent for 5 minutes to 5 hours.

The compound of the formula (XXV) may be produced by reacting the compound of the formula (XXIV) and the compound of the formula (XXII). This reaction can be proceeded by the same operation as that for the reaction for converting the compound of the formula (XXI) to the compound of the formula (XXIII). The compound of the formula (XIV) may be produced by reacting the compound of the formula (XXV) with the compound of the formula (V). This reaction can be proceeded by the same operation as that for the reaction for converting the compound of the formula (XXIII) to the compound of the formula (XIII).

The processes for producing the compounds which are used as materials in the above-described reactions will now be described.

Firstly, the production process of the compound of the formula (III) will now be described.
Synthesis of Compound (IIIa) Which is Compound of the Formula (III) Wherein W is C=O and l is 1

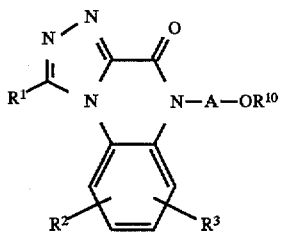
(IIIa)

(wherein $R^1$, $R^2$, $R^3$, $R^{10}$ and A represent the same meanings as mentioned above)

Among the compounds represented by the formula (III), the compound of the formula (IIIa) may be obtained by using a compound of the formula (XXVI) as a starting material according to the following reaction steps.

That is, by reacting the compound of the formula (XXVI) with a compound of the formula (XXVII):

$H_2N-A-OR^{10}$ (XXVII)

(wherein $R^{10}$ and A represent the same meanings as mentioned above),
the compound of the formula (XXVIII) is obtained. The reaction may be carried out in the absence of a solvent, or usually in the presence of water or an organic solvent (such as tetrahydrofuran, ethanol, benzene, toluene or dimethylformamide) or a mixture thereof, at room temperature to the refluxing temperature of the solvent for 1 hour to 1 month. To promote the reaction, an acid capturing agent may be added to the system. Examples of the acid capturing agent include organic bases such as pyridine and triethylamine, and inorganic bases such as potassium carbonate and sodium carbonate.

By reducing the compound of the formula (XXVIII), the compound of the formula (XXIX) is obtained. The reaction, for example, the catalytic reduction employing platinum oxide, paradium, Raney nickel or the like may be carried out in water or in an organic solvent (such as methanol, ethanol or dimethylformamide) at atmospheric pressure to 50 atms. In this reaction, acetic acid, hydrochloric acid or the like may coexist in the system. The reduction may be carried out using a metal such as iron, zinc or tin under acidic condition employing hydrochloric acid, acetic acid or the like. In cases where zinc powder is used, the reaction may be carried out also under the neutral or basic condition. Alternatively, the reduction may be carried out by employing a metal hydride (such as lithium aluminum hydride or sodium borohydride) in an inert solvent (such as ether, tetrahydrofuran or dioxane) or by employing a sulfur-containing compound such as sodium sulfide, sodium hydrosulfide or sodium dithionite in a solvent such as ethanol, toluene, water or aqueous ammonia. Although the reaction conditions differ depending on the method of reduction, the reaction proceeds at 0°–100° C. in 30 minutes to 1 week.

By reacting the compound of the formula (XXIX) with an oxalic acid derivative of the formula (XXX):

(wherein E represents $OR^{14}$ or X, $R^{14}$ represents hydrogen or lower alkyl, and X represents a halogen atom), the compound of the formula (XXXI) is obtained. The reaction may be carried out in an inert solvent (such as o-dichlorobenzene, toluene or xylene) at 0° C. to the refluxing temperature of the solvent for 5 minutes to 6 hours.

By subjecting the compound of the formula (XXXI) to the same operation as that for converting the compound of the formula (XVIII) to the compound of the formula (XIXa–c), a compound of the formula (XXXII) (in the formula, Q represents halogen, —SH or —$OR^{11}$ (wherein $R^{11}$ represents lower alkyl) is obtained.

By subjecting the compound of the formula (XXXII) to the same operation as that for converting the compound of the formula (XIXa–c) to the compound of the formula (I), a compound of the formula (IIIa) may be obtained.

Synthesis of Compound (IIIb) Which is Represented by the Formula (III) Wherein W is $CR^4R^5$ and l is 1

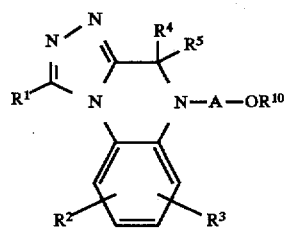

(wherein $R^1$, $R^2$, $R^3$, $R^4$, $R^5$, $R^{10}$ and A represent the same meanings as mentioned above)

Among the compounds represented by the formula (III), the compound represented by the formula (IIIb) may be obtained by using the compound of the formula (XXVI) as a starting material according to the following reaction steps.

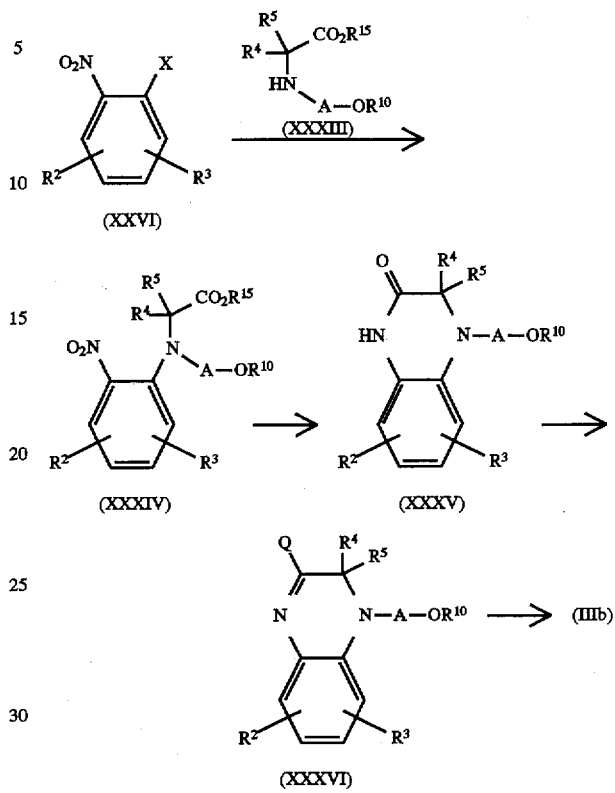

By reacting the compound of the formula (XXVI) with a compound of the formula (XXXIII):

(wherein $R^{15}$ represents lower alkyl, and $R^4$, $R^5$, $R^{10}$ and A represent the same meanings as mentioned above), the compound of the formula (XXXIV) is obtained. The reaction is carried out by the same operation as that for converting the compound of the formula (XXVI) to the compound of the formula (XXVIII). Then the compound of the formula (XXXV) is obtained by reducing the compound of the formula (XXXIV). The reaction is carried out by the same operation as that for converting the compound of the formula (XXVIII) to the compound of the formula (XXIX). The compound of the formula (XXXV) is then subjected to the same operation as that for converting the compound of the formula (XVIII) to the compound of the formula (XIXa–c) to obtain the compound of the formula (XXXVI). The compound of the formula (XXXVI) is then subjected to the same operation as that for converting the compound of the formula (XIXa–c) to the compound of the formula (I) to obtain the compound of the formula (IIIb).

In the above-described reaction steps, the compound of the formula (XXXIII) may be produced by the following reaction.

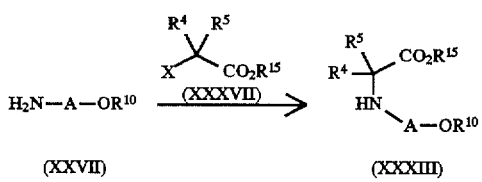

The compound of the formula (XXXIII) may be produced by reacting a compound of the formula (XXVII) with a compound of the formula (XXXVII):

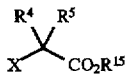

(XXXVII)

(wherein X represents halogen, and $R^4$, $R^5$ and $R^{15}$ represent the same meanings as mentioned above). The reaction may be carried out in an inert solvent (such as tetrahydrofuran, ethanol, 2-butanone, benzene or toluene) at 0° C. to the refluxing temperature of the employed solvent for 5 minutes to 24 hours.

Synthesis of Compound (IIIc) Represented by the Formula (III) Wherein l is 0

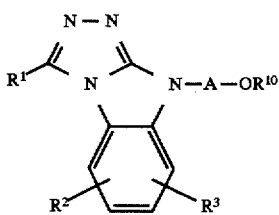

(IIIc)

(wherein $R^1$, $R^2$, $R^3$, $R^{10}$ and A represent the same meanings as mentioned above)

Among the compounds represented by the formula (III), the compound represented by the formula (IIIc) may be obtained by using a compound of the formula (XXIX) as a starting material according to the following reaction steps.

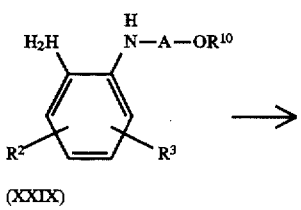

(XXIX)

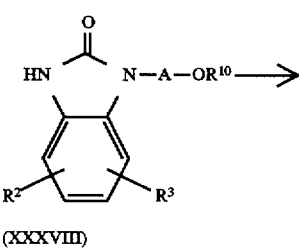

(XXXVIII)

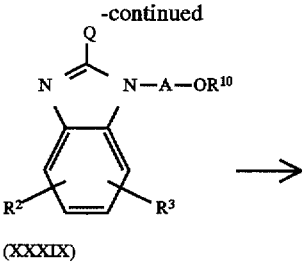

(XXXIX)

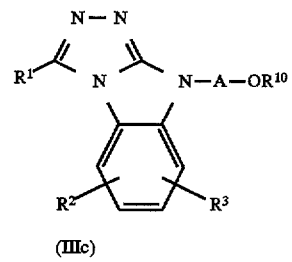

(IIIc)

The compound of the formula (XXIX) is reacted with urea to obtain the compound of the formula (XXXVIII). This reaction may be carried out in the absence of a solvent at 80° C. to 200° C. for 5 minutes to 20 hours. The compound of the formula (XXXVIII) is then subjected to the same operation as that for converting the compound of the formula (XVIII) to the compound of the formula (XIXa–c), to obtain the compound of the formula (XXXIX). Finally, the compound of the formula (XXXIX) is then subjected to the same operation as that for converting the compound of the formula (XIXa–c) to the compound of the formula (I), to obtain the compound of the formula (IIIc).

Synthesis of Compound (IIId) Represented by the Formula (III) Wherein W is $CR^4R^5$ and l is 2

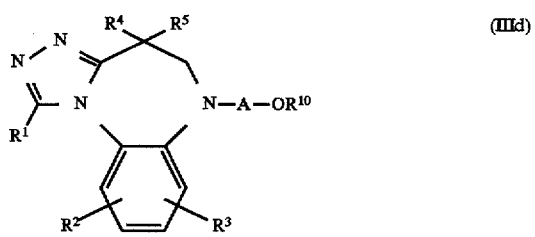

(IIId)

(wherein $R^1$, $R^2$, $R^3$, $R^4$, $R^5$, $R^{10}$ and A represent the same meanings as mentioned above)

Among the compounds represented by the formula (III), the compound of the formula (IIId) may be obtained by using a compound of the formula (XXIX) as a starting material according to the following reaction steps.

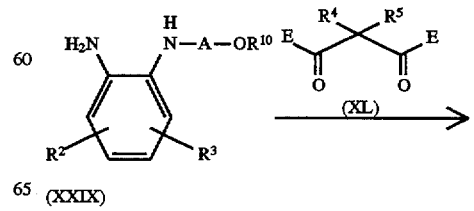

(XXIX)

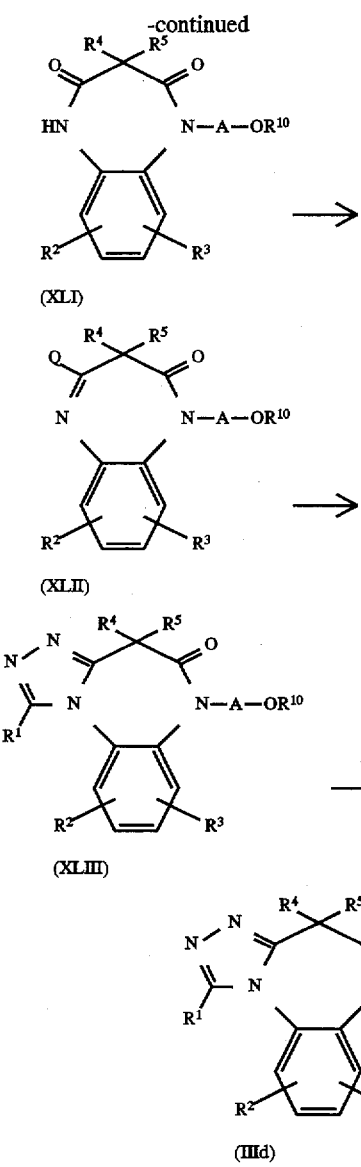

(XLI)

(XLII)

(XLIII)

(IIId)

The compound of the formula (XLI) is obtained by reacting the compound of the formula (XXIX) with a compound of the formula (XL):

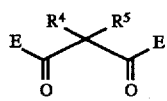

(XL)

(wherein E represents $OR^{14}$ or X, $R^{14}$ represents hydrogen or lower alkyl, X represents halogen, and $R^4$ and $R^5$ represent the same meanings as mentioned above). The reaction may be carried out by the same operation as that for converting the compound of the formula (XXIX) to the compound of the formula (XXXI). Then the compound of the formula (XLI) is subjected to the same operation as that for converting the compound of the formula (XVIII) to the compound of the formula (XIXa–c) to obtain the compound of the formula (XLII). The compound of the formula (XLII) is then subjected to the same operation as that for converting the compound of the formula (XIXa–c) to the compound of the formula (I) to obtain the compound of the formula (XLIII). Finally, the compound of the formula (IIId) is obtained by reducing the compound of the formula (XLIII).

Examples of the reducing agent employed in the reaction include lithium aluminum hydride, aluminum hydride, borane, sodium borohydride, lithium borohydride and the like. The reaction temperature may be 0° C. to the refluxing temperature of the solvent and the reaction time may be 5 minutes to 6 hours.

The compound of the formula (III) may be produced by alkylating the compound of the formula (V). That is, the compound of the formula (III) may be produced by reacting the compound of the formula (V) with a compound of the formula (XLIV):

(XLIV)

(wherein X represents halogen, and $R^{10}$ and A represent the same meanings as mentioned above).

The reaction may preferably be carried out in the presence of an inorganic base such as sodium carbonate, potassium hydride, sodium hydride, sodium amide, or calcium hydride, or an organic base such as triethylamine, potassium t-butoxide or pyridine, in an inert solvent (such as ethanol, n-butanol, dimethylformamide, dimethylacetamide, tetrahydrofuran, dioxane or 2-butanone) at 0° C. to the boiling point of the employed solvent for 1 minute to 24 hours.

The production process of the compound of the formula (V) will now be described.

Synthesis of Compound (Va) Which is Represented by the Formula (V) Wherein W is C=O and l is 1

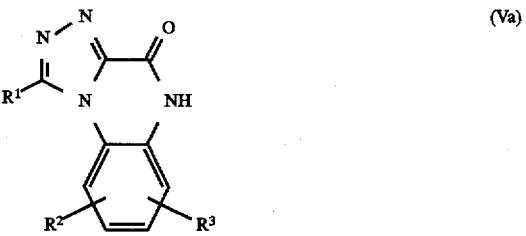

(Va)

(wherein $R^1$, $R^2$ and $R^3$ represent the same meanings as mentioned above)

Among the compounds represented by the formula (V), the compound of the formula (Va) may be produced by using the compound of the formula (XLV) as a starting material according to the following reaction steps.

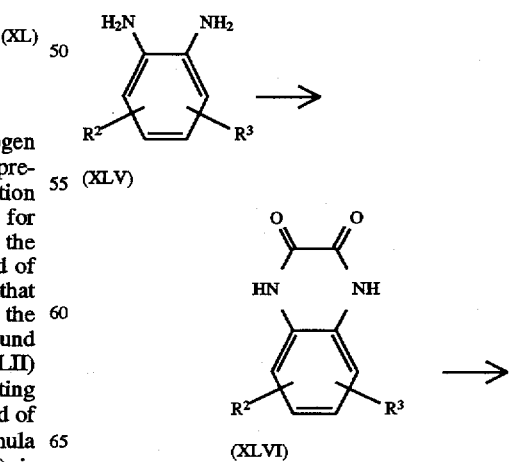

(XLV)

(XLVI)

-continued

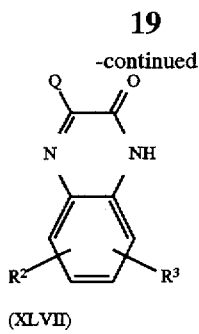

(XLVII)

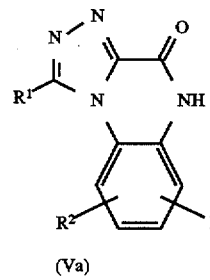

(Va)

By reacting the compound of the formula (XLV) with the compound of the formula (XXX), the compound of the formula (XLVI) is obtained. The reaction may be carried out in the same manner as in the reaction for converting the compound of the formula (XXIX) to the compound of the formula (XXXI). The compound of the formula (XLVI) is then subjected to the same operation as that for converting the compound of the formula (XVIII) to the compound of the formula (XIXa–c) to obtain a compound of the formula (XLVII). Finally, by subjecting the compound of the formula (XLVII) to the same operation as that for converting the compound of the formula (XIXa–c) to the compound of the formula (I), the compound of the formula (Va) is obtained.

Synthesis of Compound (Vb) Which is Represented by Formula (V) Wherein W is $CR^4R^5$ and l is 1

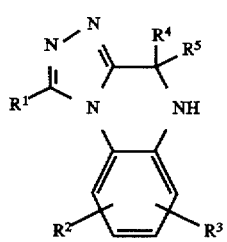

(wherein $R^1$, $R^2$, $R^3$, $R^4$ and $R^5$ represent the same meanings as mentioned above)

Among the compounds represented by the formula (V), the compound of the formula (Vb) may be produced by employing the compound of the formula (XLV) as a starting material according to the following reaction steps.

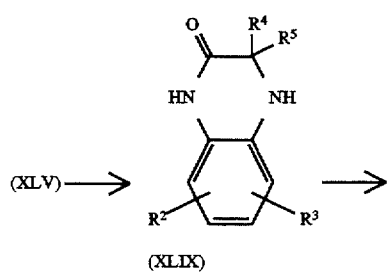

-continued

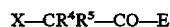

(L)                                   (Vb)

By reacting the compound of the formula (XLV) with a compound of the formula (XLVIII):

$$X\text{—}CR^4R^5\text{—}CO\text{—}E \qquad \text{(XLVIII)}$$

(wherein E represents $OR^{14}$ or X, $R^{14}$ represents hydrogen or lower alkyl, X represents halogen and $R^4$ and $R^5$ represent the same meanings as mentioned above), the compound of the formula (XLIX) is obtained. The reaction may be carried out in an inert solvent (such as tetrahydrofuran, ethanol, 2-butanone, benzene or toluene) at 0° C. to the refluxing temperature of the solvent for 5 minutes to 24 hours. By subjecting the compound of the formula (XLIX) to the same operation as that for converting the compound of the formula (XVIII) to the compound of the formula (XIXa–c), the compound of the formula (L) may be obtained. By subjecting the compound of the formula (L) to the same operation as that for converting the compound of the formula (XIXa–c) to the compound of the formula (I), the compound of the formula (Vb) may be obtained.

Synthesis of Compound (Vc) Represented by the Formula (V) Wherein l is 0

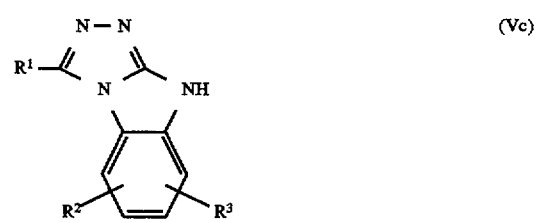

(wherein $R^1$, $R^2$ and $R^3$ represent the same meanings as mentioned above)

Among the compounds represented by the formula (V), the compound represented by the formula (Vc) may be produced by using the compound of the formula (XLV) as a starting material according to the following reaction steps.

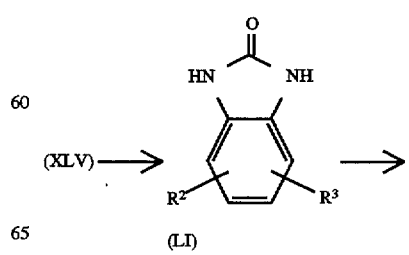

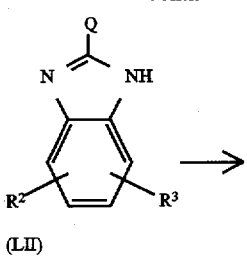
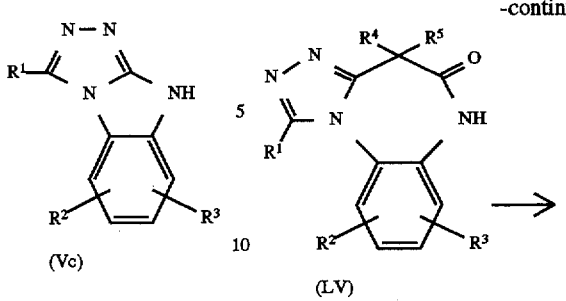

The compound of the formula (LI) may be obtained by reacting the compound of the formula (XLV) with urea. The reaction may be carried out in the same manner as the reaction for converting the compound of the formula (XXIX) to the compound of the formula (XXXVIII). The compound of the formula (LII) may be obtained by subjecting the compound of the formula (LI) to the same operation as that for converting the compound of the formula (XVIII) to the compound of the formula (XIXa–c). By subjecting the compound of the formula (LII) to the same operation as that for converting the compound of the formula (XIXa–c) to the compound of the formula (I), the compound of the formula (Vc) may be obtained.

Synthesis of Compound (Vd) Represented by the Formula (V) Wherein W is $CR^4R^5$ and l is 2

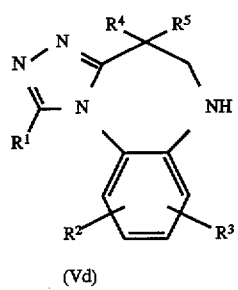

(wherein $R^1$, $R^2$, $R^3$, $R^4$ and $R^5$ represent the same meanings as mentioned above)

Among the compounds represented by the formula (V), the compound represented by the formula (Vd) may be obtained by using the compound of the formula (XLV) as a starting material according to the following reaction steps.

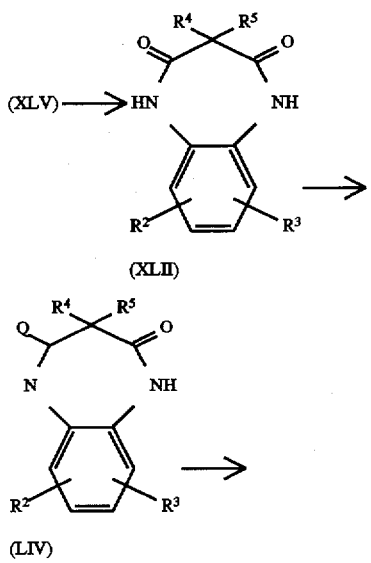

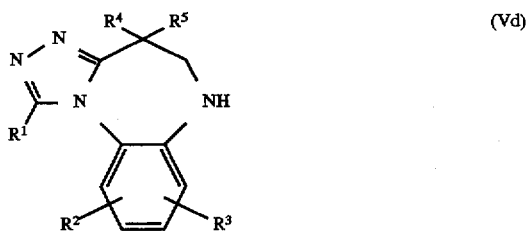

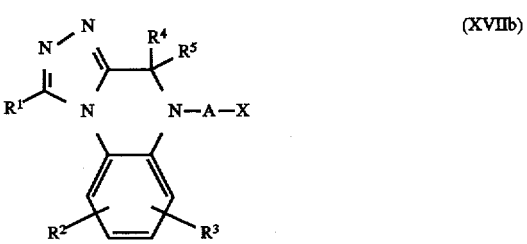

By reacting the compound of the formula (XLV) with the compound of the formula (XL), the compound of the formula (LIII) may be obtained. The reaction may be carried out in the same manner as the reaction for converting the compound of the formula (XXIX) to the compound of the formula (XLI). The compound of the formula (LIII) is subjected to the same operation as that for converting the compound of the formula (XVIII) to the compound of the formula (XIXa–c), to obtain the compound of the formula (LIV). By subjecting the compound of the formula (LIV) to the same operation as that for converting the compound of the formula (XIXa–c) to the compound of the formula (I), the compound of the formula (LV) is obtained. The compound of the formula (Vd) may be obtained by subjecting the compound of the formula (LV) to the same operation as that for converting the compound of the formula (XII) to the compound of the formula (Ib).

Among the compounds represented by the formula (XVII), the compound of the formula (XVIIb):

(wherein X represents halogen and $R^1$, $R^2$, $R^3$, $R^4$, $R^5$ and A represent the same meanings as mentioned above) which is a compound represented by the formula (XVII) wherein W is $CR^4R^5$ and l is 1, may be obtained by employing a compound of the formula (Vb) as a starting material according to the following method.

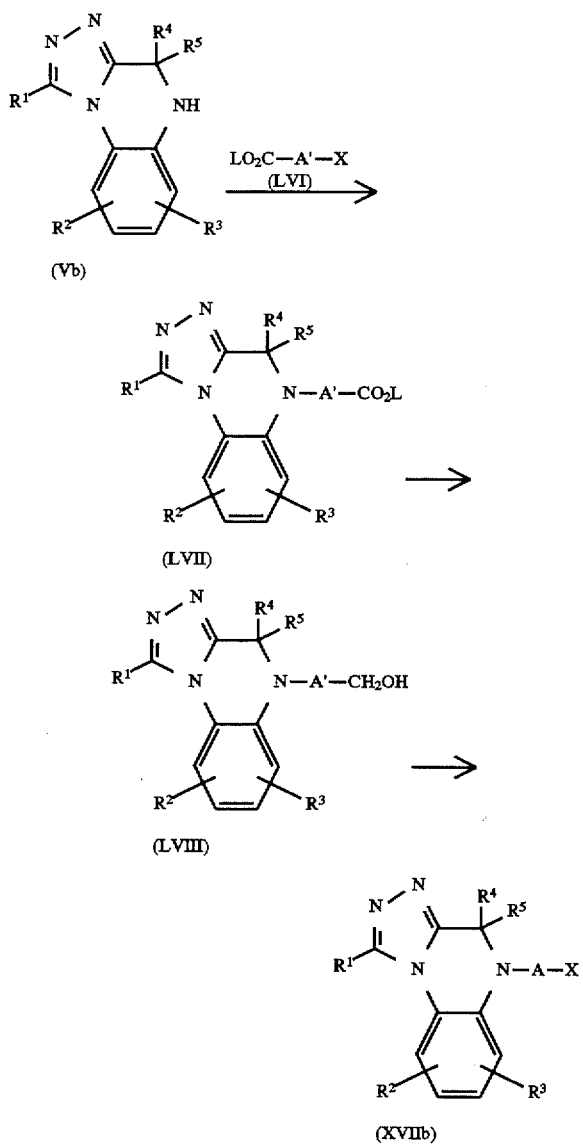

(Vb)

(LVII)

(LVIII)

(XVIIb)

That is, a compound of the formula (Vb):

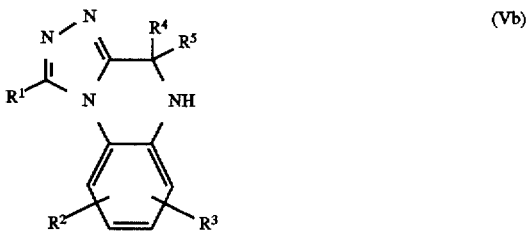

(Vb)

(wherein $R^1$, $R^2$, $R^3$, $R^4$ and $R^5$ represent the same meanings as mentioned above)
is reacted with a compound of the formula (LVI):

$LO_2C-A'-X$  (LVI)

(wherein X represents halogen, A' represents a $C_1$–$C_4$ saturated or unsaturated straight or branched alkylene (one or more hetero atoms may be contained), and L represents the same meaning as mentioned above) to obtain a compound of the formula (LVII):

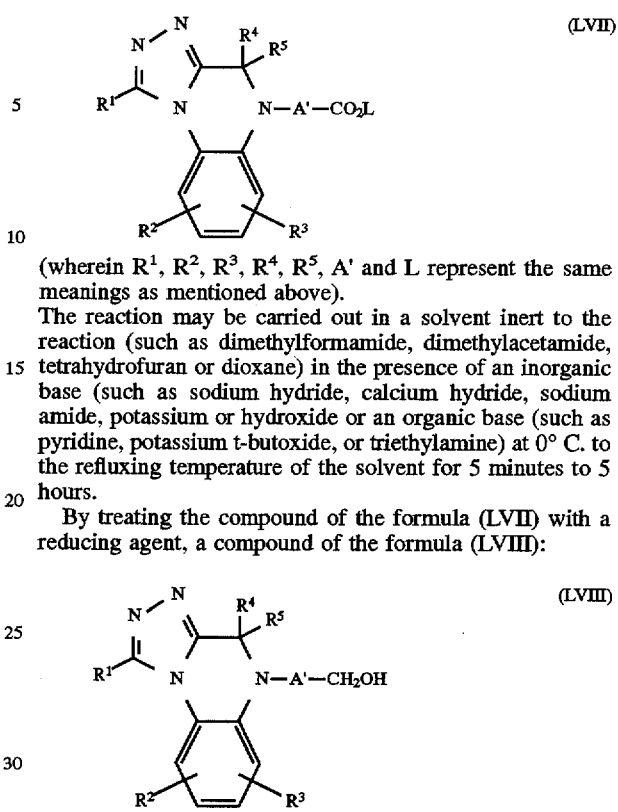

(LVII)

(wherein $R^1$, $R^2$, $R^3$, $R^4$, $R^5$, A' and L represent the same meanings as mentioned above).

The reaction may be carried out in a solvent inert to the reaction (such as dimethylformamide, dimethylacetamide, tetrahydrofuran or dioxane) in the presence of an inorganic base (such as sodium hydride, calcium hydride, sodium amide, potassium or hydroxide or an organic base (such as pyridine, potassium t-butoxide, or triethylamine) at 0° C. to the refluxing temperature of the solvent for 5 minutes to 5 hours.

By treating the compound of the formula (LVII) with a reducing agent, a compound of the formula (LVIII):

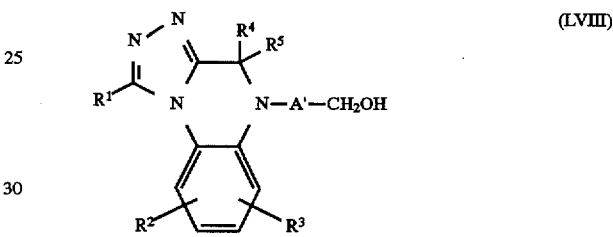

(LVIII)

(wherein $R^1$, $R^2$, $R^3$, $R^4$, $R^5$ and A' represent the same meanings as mentioned above)
may be obtained. Examples of the reducing agent to be employed in the reaction include lithium aluminum hydride, aluminum hydride, borane, sodium borohydride, lithium borohydride and the like. The reaction temperature may be 0° C. to the refluxing temperature of the solvent used and the reaction time may be 5 minutes to 6 hours.

Finally, by treating the compound of the formula (LVIII) with a halogenating agent, the compound of the formula (XVIIb) may be produced. Examples of the halogenating agent include phosphorus oxychloride, thionyl chloride and phosphorus trichloride, as well as thionyl chloride-dimethylformamide, phosphorus oxychloride-N-methylformanilide and the like. The reaction may be carried out in an inert solvent (such as benzene, toluene, xylene or chloroform) at 0° C. to the refluxing temperature of the employed solvent for 5 minutes to 6 hours.

The thus obtained compound of the formula (I) may be separated from the reaction mixture and purified by conventional methods such as recrystallization and chromatography. By treating the compound of the formula (I) with an inorganic acid, organic acid or an amino acid according to a conventional method, the compound may be converted to the pharmaceutically acceptable salts described above.

Among the compounds of the present invention, those having an asymmetric carbon atom are usually obtained as racemic compounds. The racemic compound may be divided into optical isomers according to a conventional method. Such optical isomers may also be produced by employing optically active compounds as starting materials. In cases where diastereomers exist, each diastereomer may be purified by fractional recrystallization or by chromatography.

In the processes for producing the intermediates of the compound of the formula (I), the compounds employed in the reactions may be in the form of inorganic salts such as hydrochloric acid salt and sulfuric acid salt or in the form of organic salts such as tartaric acid salt and fumaric acid salt as long as the reactions are not adversely affected.

[Action]

The compound of the formula (I) and pharmaceutically acceptable salts thereof exhibit anti-PAF property and anti-histaminic property, and are useful for prophylaxis and treatment of inflammatory diseases, allergic diseases (such as bronchial asthma and psoriasis), diseases caused by PAF (e.g., diseases of circulatory organs, such as thrombosis, apoplexy, cardiac infarction, angina pectoris, thrombophlebitis, nephritis, diabetic nephritis, endotoxin shock, intravascular blood coagulation syndrome caused by endotoxin, anaphylaxis shock and hemorrhagic shock; diseases of digestive organs such as stomach ulcer; pneumonia; rejection after organ transplantation due to increase in the production of PAF; disorders of organs by surgery of organs and the like), and diseases for which PAF antagonists are effective (such as hyperendocerinemia).

The compound of the formula (I) and acid addition salts thereof may be administered as they are in the form of powder or in the form of an appropriate medical formulation to mammals orally or parenterally.

Examples of the formulations for oral administration include tablets, pills, powders, capsules, granules, medicated syrups, emulsions and suspensions. These formulations may be prepared by the known methods and contain carriers or vehicles usually used in the formulations. For example, as the carrier or vehicle of tablets, lactose, starch, sucrose, magnesium stearate and the like may be employed.

Examples of the formulations for parenteral administration include ointments, injection solutions, fomentations, liniments, suppositories, formulations for percutaneous absorption and the like. The injection solution may be formulated according to known methods. For example, the injection solution may be formulated by dissolving, suspending or emulsifying the compound of the formula (I) or salts thereof in aseptic aqueous or oily solution usually used in injection solutions. Examples of the aqueous solution for injection include physiological saline and glucose solution, and examples of the oily solution include sesame oil and soybean oil. Solubilizers may be added to the injection solutions. The suppositories used for rectal administration may be formulated by, for example, mixing the compound of the formula (I) or salts thereof with a usual base for suppositories and molding the mixture.

Although the effective dose and the number of administration of the compound of the formula (I) and the pharmaceutically acceptable salts thereof vary depending on the administration route, age and body weight of the patient and on the property and the degree of the disease to be treated, usually, 0.1–1000 mg, preferably 1–200 mg of the compound may be administered per day per an adult in one time or in several times.

The above-described formulations may contain other effective ingredients for the treatment of other diseases as long as undesired interactions are not brought about by the combination of the compound of the formula (I) or the pharmaceutically acceptable salts thereof and the other effective ingredients. Examples of such effective ingredient include steroid agents, non-steroid anti-inflammatories, lipoxygenase inhibitors, leukotriene antagonists, bronchodilators, thromboxane synthesis inhibitors, histamine release inhibitors, serotonin antagonists, adenosine receptor antagonists, adrenergic β-receptor antagonists, immunosuppressive agents, immunomodulators and the like.

An examples of the composition of a tablet containing the compound of the present invention is described below.

Formulation Example Tablet

A tablet having the following composition is formulated according to a conventional method.

| | |
|---|---|
| Compound of Example 6 | 20 mg |
| Lactose | 80 mg |
| Corn Starch | 30 mg |
| Polyvinyl Alcohol | 2 mg |
| Magnesium Stearate | 1 mg |
| Tar Pigment | Trace Amount |

[EXAMPLES]

The present invention will now be described more concretely by way of examples thereof. It should be noted that the present invention is not limited to the examples.

Example 1

4-(3-ethoxypropyl)-2-hydroxy-quinoxalin-3(4H)-one (1)

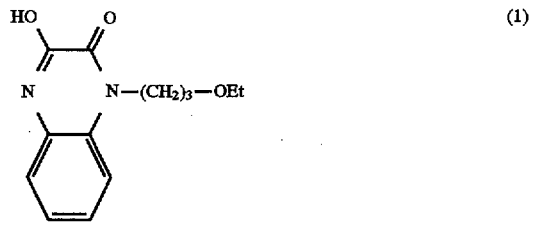

In a solution containing 26.9 g of oxalyl chloride in 200 ml of o-dichlorobenzene at 60° C. under stirring, a solution containing 35.5 g of N-(3-ethoxypropyl)-o-phenylenediamine in 220 ml of o-dichlorobenzene is added for 42 minutes in several times. The mixture is then heated and stirred at 130° C. for 1.1 hours. The mixture is subjected to filtration during hot and the filtrate is cooled. Ether is added to the filtrate and the crystals are filtered, washed and dried, followed by combining second crystals to obtain 25.2 g of (1).

IR(KBr) cm$^{-1}$:2868,1690,1665,1311,1122,756

$^1$HNMR(DMSO-d6) δ:7.35(1H,m),7.20–7.17(3H,m), 4.17(2H,t,J=7.1),3.52–3.29(4H,m),1.86(2H,quint,J=6.9), 1.11(3H,t,J=6.9)

MS: 248(M+)

Example 2

4-(3-ethoxypropyl)-2-chloro-quinoxalin-3(4H)-one (2)

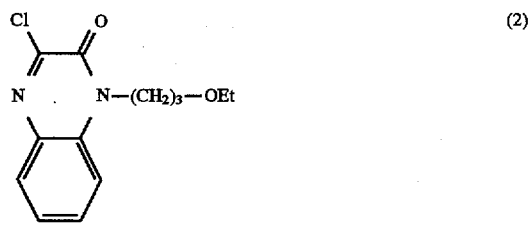

To 22.5 g of (1), 330 ml of toluene, 10 ml of dimethylformamide and 10 ml of thionyl chloride are added and the resulting mixture is heated to reflux for 2 hours. The mixture is then subjected to filtration during hot and the filtrate is concentrated. The resultant is purified by silica gel column chromatography (ethyl acetate:hexane=1:3–1:2) to obtain 23.5 g of (2) in the form of yellow oil.

IR(Neat) cm$^{-1}$:2976,2870,1669,1605,1468,1114,1083, 756,629

$^1$HNMR(CDCl3) δ:7.83(1H,m),7.55(2H,m),7.36(1H,m), 4.43(2H,t,J=7.0),3.52(2H,t,J=5.8),3.49(2H,q,J=7.0), 2.07 (2H,m),1.23(3H,t,J=7.0)

MS: 266(M+)

Example 3

5-(3-ethoxypropyl)-4,5-dihydro-1-methyl-[1,2,4]triazolo[4,3-a]quinoxalin-4(5H)-one (3)

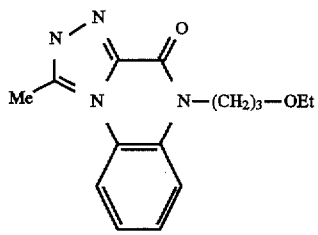

(3)

To 23.3 g of (2) and 7.79 g of acetohydrazide, 180 ml of n-butanol is added and the resultant is heated to reflux for 0.9 hours. Then 60 ml of n-butanol is added and the resultant is heated to reflux for 1.5 hours. The solvent is evaporated, and dichloromethane and water are added to carry out extraction. The organic layer is washed with water and dried. The solvent is evaporated and the product is recrystallized from isopropanol, followed by washing with ethyl acetate and drying to obtain 18.9 g of (3) in the form of yellow crystals. mp:120.5°–123° C.

IR(KBr) cm$^{-1}$:2966,1678,1429,775,768

$^1$HNMR(CDCl3) δ:8.02(1H,dd,J=7.9,1.5),7.65–7.21(3H, m),4.46(2H,t,J=7.4),3.62–3.39(4H,m), 3.09(3H,s),2.05(2H, m),1.22(3H,t,J=7.0)

MS: 286(M+)

Example 4

4,5-dihydro-1-methyl-5-[3-[4-(diphenylmethylene) piperidin-1-yl]propyl][1,2,4]triazolo[4,3-a]quinoxalin-4 (5H)-one (4)

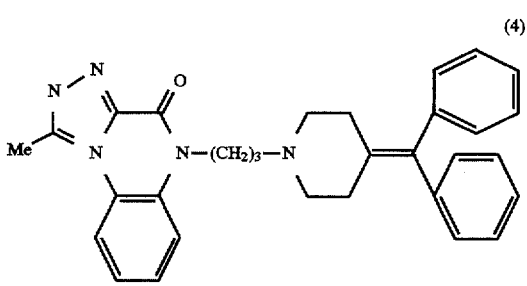

(4)

To 2.51 g of (3), 18 ml of 48% hydrobromic acid is added and the mixture is heated to reflux for 2.7 hours. After evaporating the solvent under reduced pressure, 1.96 g of 4-(diphenylmethylene)piperidine, 2.33 g of sodium carbonate and 18 ml of dimethylformamide are added to the mixture and the resulting mixture is stirred at 60°–70° C. for 4.9 hours. The solvent is evaporated and water and dichloromethane are added, followed by filtration using Celite. The filtrate is extracted and the organic layer is washed with water and dried. The solvent is evaporated and the residue is purified by silica gel column chromatography (ethyl acetate:methanol=6:1), and the product is recrystallized from ethanol and a small amount of n-butanol to obtain 2.50 g of (4) in the form of white crystals.

mp:188.5°–189.5° C.

Elementary Analysis: as C31H31N5O.1/4H2O Calcd.:C, 75.35;H,6.43;N,14.17 Found :C,75.21;H,6.36;N,14.27

IR(KBr) cm$^{-1}$:1673,1427,760,702

$^1$HNMR(CDCl3) δ: 8.01(1H,dd,J=8.3,1.5),7.69(1H,d,J= 7.3),7.51(1H,td,J=8.1,1.5),7.36(1H,td,J=7.8,1.0),7.28(4H,t-like,J=5.9),7.20(2H,t-like,J=7.3),7.12(4H,m), 4.44(2H,t,J= 7.3),3.09(3H,s),2.51(6H,t-like), 2.39(4H,t-like,J=5.6),1.98 (2H,quint,J=7.3)

MS: 489(M+)

Example 5

4,5-dihydro-1-methyl-5-[3-[4-(diphenylmethyl)piperazin-1-yl]propyl][1,2,4]triazolo[4,3-a]quinoxalin-4(5H)-one(5)

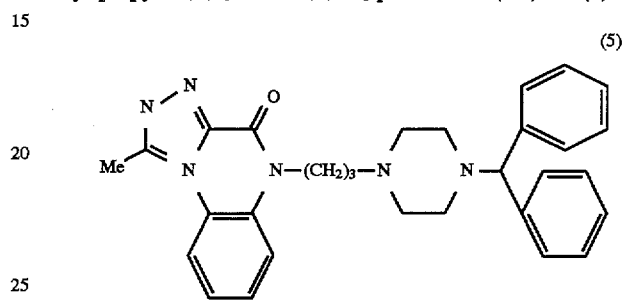

(5)

The same procedure as in Example 4 is repeated except that 1-(diphenylmethyl)piperazine is used in place of 4-(diphenylmethylene)piperidine to obtain (5) in the form of colorless amorphous.

Elementary Analysis:as C30H32N6O Calcd.:C,73.14;H, 6.55;N,17.06 Found :C,73.27;H,6.38;N,17.27

IR(KBr) cm$^{-1}$:2814,1686,1427,750,708

$^1$HNMR(CDCl3) δ:7.99(1H,dd,J=8.3,1.0),7.64(1H,d,J= 7.8),7.47(1H,td,J=7.8,1.5),7.41(4H,AB,J=7.3),7.34(1H,td, J=7.8,1.0), 7.27(4H,t,J=7.3),7.17 (2H ,t,J=7.3),4.40(2H,t,J= 6.8), 4.20(1H,s),3.08(3H,s),2.49(2H,t,J=6.8),2.47(8H,brs), 1.94(2H,quint,J=6.8)

MS: 492(M)+

Example 6

4,5-dihydro-1-methyl-5-[3-[4-[(4-chlorophenyl) phenylmethyl]piperazine-1-yl]propyl][1,2,4]triazolo[4,3-a] quinoxalin-4(5H)-one (6)

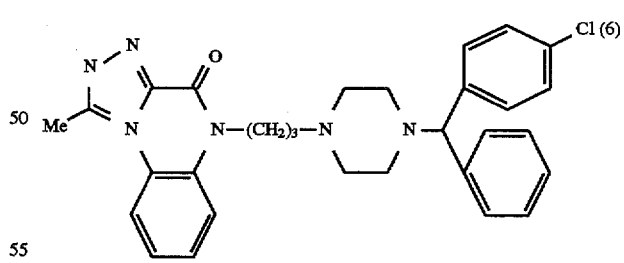

(6)

The same procedure as in Example 4 is repeated except that 1-[(4-chlorophenyl)phenylmethyl]piperazine is used in place of 4-(diphenylmethylene)piperidine to obtain (6) in the form of colorless amorphous.

IR(KBr) cm$^{-1}$:2810,1675,1425,1240,755

$^1$HNMR(CDCl3) δ:7.99(1H,dd,J=8.6,1.2),7.62(1H,d,J= 8.6), 7.47(1H,td,J=7.9,1.2),7.37–7.33(3H,m), 7.35(2H,AB, J=8.5),7.28(2H,t,J=7.9),7.24(2H,AB,J=7.9), 7.19(1H,tt,J= 7.3,1.2),4.40(2H,t,J=7.3),4.19(1H,s), 3.09(3H,s),2.50(2H,t, J=6.7),2.42(8H,brs), 1.95(2H,quint,J=6.7)

MS: 527(M+H)+

Example 7

4,5-dihydro-1-methyl-5-[3-[4-[(4-chlorophenyl) phenylmethyl]piperazin-1-yl]propyl][1,2,4]triazolo[4,3-a]quinoxalin-4(5H)-one hydrochloride (7)

In ethyl acetate, 0.69 g of the compound of Example 6 is dissolved and hydrogen chloride gas is blown into the resulting solution. After condensing the solution, generated crystals are separated by filtration and dried to obtain 0.54 g of (7).

mp:158°–161° C.

IR(KBr) cm⁻¹:3400,2940,2800,1675,1420,755

Example 8

4,5-dihydro-1-methyl-5-[3-[(4-chlorobenzyl) piperazin-1-yl]propyl][1,2,4]triazolo[4,3-a]quinoxalin-4(5H)-one (8)

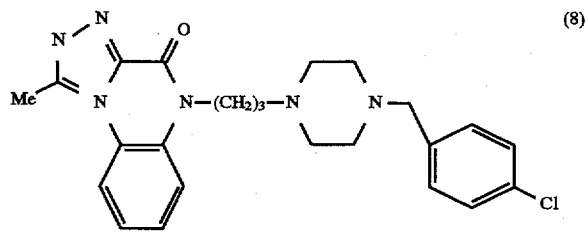

The same procedure as in Example 4 is repeated except that 1-(4-chlorobenzyl)piperazine is used in place of 4-(diphenylmethylene)piperidine to obtain (8) in the form of colorless amorphous.

Elementary analysis:as C24H27N6OCl Calcd.:C,63.92;H, 6.03;N,18.63;Cl,7.86 Found :C,64.18;H,6.26;N,18.27;Cl, 8.02

IR(KBr) cm⁻¹:2814,1682,1427,754

¹HNMR(CDCl3) δ:8.01(1H,dd,J=8.4,1.1),7.64(1H,AB, J=8.4), 7.51(1H,td,J=8.4,1.1),7.37(1H,td,J=7.9,1.1), 7.28 (2H,AB,J=8.4),7.25(2H,AB,J=8.4),4.42(2H,t,J=7.3), 3.46 (2H,s),3.10(3H,s),2.49(2H,t,J=7.0),2.47(8H,brs), 1.95(2H, quint,J=7.0)

MS: 450(M+)

Example 9

4,5-dihydro-1-methyl-5-[3-[4-(3-indolyl)piperidin-1-yl] propyl][1,2,4]triazolo[4,3-a]quinoxalin-4(5H)-one (9)

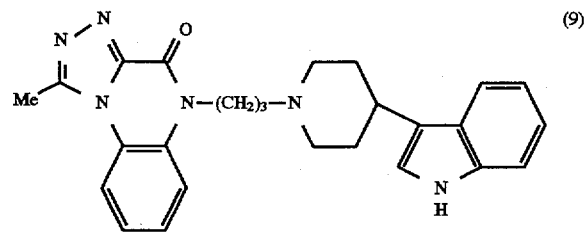

The same procedure as in Example 4 is repeated except that 4-(3-indolyl)piperidine is used in place of 4-(diphenylmethylene)piperidine to obtain (9) in the form of colorless amorphous.

mp:198°–215° C.

Elementary Analysis:as C26H28N6O Calcd.:C,70.89;H, 6.41;N,19.08 Found :C,70.68;H,6.63;N,18.84

IR(KBr) cm⁻¹:3346,1671,1460,1433,743

¹HNMR(CDCl3) δ:10.76(1H,s),8.14(1H,dd,J=7.3,1.2), 7.81(1H,d,J=7.3),7.58(1H,td,J=7.3,1.2),7.49(1H,d,J=7.9), 7.40(1H,t,J=7.3),7.32(1H,d,J=7.9),7.04(1H,t,J=7.3), 7.01 (1H,d,J=2.4),6.94(1H,t,J=7.3),4.37(2H,t,J=7.3), 2.98(3H,s), 2.88(2H,d,J=11.6),2.69(1H,t,J=11.6), 2.46(2H,t,J=6.7),2.00 (2H,t,J=11.9),1.88–1.86(4H,m), 1.47(2H,qd,J=11.9,3.1)

MS: 440(M+)

Example 10

1,2-dihydroquinoxaline-3(4H)-thione (10)

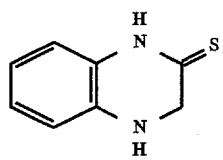

Two hundred eighty ml of Diglyme is added to 52 g of 1,2-dihydro-3-hydroxyquinoxaline, 47 g of phosphorus pentasulfide, and 59 g of sodium hydrogen carbonate, and the resulting mixture is stirred at 60° C. for 1 hour. The solvent is evaporated under reduced pressure and 500 ml of water is added to the residue. The obtained crystals are separated by filtration and washed to obtain 47 g of the captioned compound in the form of yellow green crystals. The product is recrystallized from benzene to obtain pure product.

mp:120°–123° C.

IR(KBr) cm⁻¹:3250,3180,3100,2970,1562,1510,1307

¹HNMR(CDCl3) δ:9.75(1H,brs),7.12–6.64(4H,m),4.33 (2H,s)

Example 11

1,2-dihydro-2-methylquinoxaline-3(4H)-thione (11)

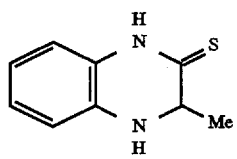

The same procedure as in Example 10 is repeated except that 1,2-dihydro-2-methyl-3-hydroxyquinoxaline is used in place of 1,2-dihydro-3-hydroxyquinoxaline to obtain (11) in the form of yellow green crystals.

mp:92°–94° C.

IR(KBr) cm⁻¹:2978,1551,1502,1383,1075,748

¹HNMR(CDCl3) δ:10.08(1H,brs),7.06–6.66(4H,m), 4.38 (1H,q,J=6.6),1.54(3H,d,J=6.6)

MS: 178(M+)

Example 12

1,2-dihydro-2,2-dimethylquinoxaline-3(4H)-thione (12)

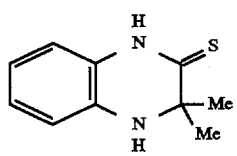

The same procedure as in Example 10 is repeated except that 1,2-dihydro-2,2-dimethyl-3-hydroxyquinoxaline is used in place of 1,2-dihydro-3-hydroxyquinoxaline to obtain (12) in the form of yellow green crystals.

mp:140°–142° C.

IR(KBr) cm⁻¹:2978,1535,1502,1359,1319,1062,745,621

¹HNMR(CDCl3) δ:9.74(1H,brs),7.0–6.6(4H,m),1.53(6H, s)

MS: 192(M+)

Example 13

4,5-dihydro-1-methyl[1,2,4]triazolo[4,3-a]quinoxaline (13)

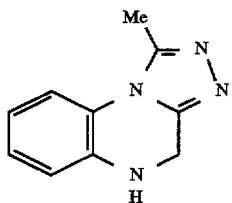
(13)

To 62 g of the compound of Example 10 and 56 g of acetohydrazide, 750 ml of n-butanol is added and the resulting mixture is heated to reflux for 4 hours. The solvent is evaporated under reduced pressure and water is added, followed by extraction with dichloromethane. The resultant is washed with water and dried. The solvent is evaporated under reduced pressure and the product is recrystallized from isopropanol to obtain 49 g of the captioned compound in the form of pale brown needle-shaped crystals.

mp:173°–174° C.

Elementary Analysis:as C10H10N4 Calcd.:C,64.50;H, 5.41;N,30.09 Found :C,64.34;H,5.51;N,29.73

IR(KBr) cm⁻¹:3230,1562,1510,1499,1431

¹HNMR(CDCl3) δ:7.50–6.82(4H,m),4.58(2H,d,J=1.8), 4.18(1H,brs),2.78(3H,s)

MS: 186(M+)

Example 14

4,5-dihydro-1,4-dimethyl[1,2,4]triazolo[4,3-a]quinoxaline (14)

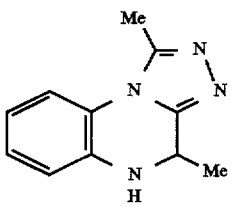
(14)

The same procedure as in Example 13 is repeated except that (11) is used in place of (10) to obtain (14) in the form of pale brown needle-shaped crystals.

mp:172°–173° C.

Elementary Analysis:as C11H12N4 Calcd.:C,65.98;H, 6.04;N,27.98 Found :C,65.84;H,6.07;N,27.91

IR(KBr) cm⁻¹:3242,1615,1533,1499,1431,1307,1135, 745

¹HNMR(CDCl3) δ:7.45(1H,d,J=7.9),7.21–6.83(3H,m), 4.70(1H,q,J=6.3),2.78(3H,s),1.70(3H,d,J=6.3)

MS: 200(M+)

Example 15

4,5-dihydro-1,4,4-trimethyl[1,2,4]triazolo[4,3-a]quinoxaline (15)

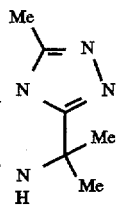
(15)

The same procedure as in Example 13 is repeated except that (12) is used in place of (10) to obtain (15) in the form of pale brown needle-shaped crystals.

mp:177°–178° C.

Elementary Analysis:as C12H14N4 Calcd.:C,67.26;H, 6.59;N,26.15 Found :C,66.99;H,6.59;N,26.00

IR(KBr) cm⁻¹:2986,1615,1531,1495,1307,737

¹HNMR(CDCl3) δ:7.52(1H,d,J=8.2),7.47–6.87(3H,m), 2.84(3H.s),1.69(6H,s)

MS: 214(M+)

Example 16

1-ethyl-4,5-dihydro[1,2,4]triazolo[4,3-a]quinoxaline (16)

(16)

In 360 ml of ethanol, 25 g of the compound of Example 10 is dissolved, and 180 ml of 80% hydrazine hydrate is added. The resulting mixture is stirred for 30 minutes. After evaporating the solvent and drying, 350 ml of ethanol, 92 ml of triethyl orthopropionate and 23 ml of sulfuric acid are added and the resulting mixture is stirred at room temperature for 1,3 hours. The resulting mixture is neutralized with aqueous sodium hydrogen carbonate solution and the resultant is extracted with dichloromethane. The organic layers are combined and washed with water and dried, followed by evaporation of the solvent under reduced pressure. The product is recrystallized from isopropanol to obtain 14 g of the pale yellow captioned compound.

mp:157°–159° C.

Elementary Analysis:as C11H12N4 Calcd.:C,65.90;H, 6.10;N,28.10 Found :C,65.84;H,6.07;N,27.91

IR(KBr) cm⁻¹:3256,1562,1499,1437,1315,745

¹HNMR(CDCl3) δ:7.49–6.84(4H,m),4.58(2H,d,J=1.8), 4.18(1H,brs), 3.13(2H,q,J=7.5),1.51(3H,t,J=7.3)

MS: 200(M+)

Example 17

4,5-dihydro-1-propyl[1,2,4]triazolo[4,3-a]quinoxaline

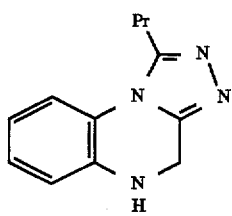
(17)

The same procedure as in Example 16 is repeated except that triethyl orthobutyrate is used in place of triethyl orthopropionate to obtain pale yellow (17).

mp:130°–132.5° C.

Elementary Analysis:as C12H14N4 Calcd.:C,67.26;H, 6.59;N,26.15 Found :C,66.80;H,6.55;N,25.92

IR(KBr) cm$^{-1}$:3244,1499,1431,1320,1299,1270,750

$^1$HNMR(CDCl3) δ:7.46–6.85(4H,m),4.56(2H,d,J=1.2), 4.25(1H,brs), 3.07(2H,t,J=7.0),1.91(2H,quint,J=7.7),1.10 (3H,t,J=7.0)

MS: 214(M+)

Example 18

5-(3-ethoxypropyl)-4,5-dihydro-1-methyl[1,2,4]triazolo[4,3-a]quinoxaline (18)

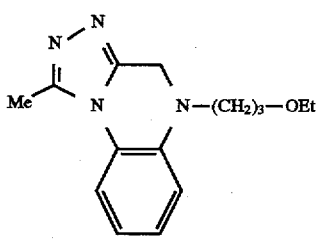
(18)

To 10 g of 60% sodium hydride, 200 ml of dimethylformamide is added, and then 32 g of the compound of Example 13 is added at 0° C. The resulting mixture is stirred at 0° C. for 30 minutes and 35 g of 1-bromo-3-ethoxypropane is added dropwise. After stirring the resulting mixture at room temperature for 1 hour, water is added and the resultant is subjected to extraction with dichloromethane. The organic layer is washed with water and dried, followed by evaporation of the solvent under reduced pressure. The residue is recrystallized from isopropanol to obtain 36 g of the captioned compound in the form of pale yellow needle-shaped crystals.

mp:118°–119° C.

Elementary Analysis:as C15H20N4O Calcd.:C,66.15;H, 7.40;N,20.57 Found :C,66.23;H,7.44;N,20.65

IR(KBr) cm$^{-1}$:1555,1504,1477,1427,1108,752

$^1$HNMR(CDCl3) δ:7.50–6.91(4H,m),4.44(2H,s),3.48 (6H,m),2.78(3H,s),1.95(2H,m), 1.26(3H,t,J=3.7)

MS: 272(M+)

Example 19

5-(3-bromopropyl)-4,5-dihydro-1-methyl[1,2,4]triazolo[4,3-a]quinoxaline (19)

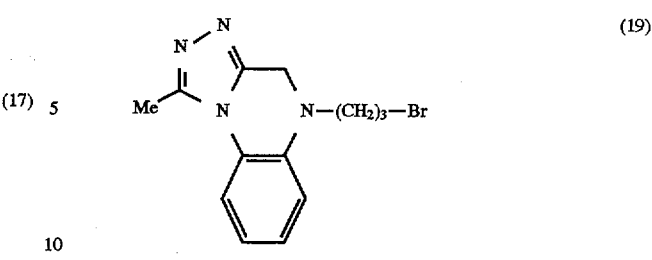
(19)

To 2.5 g of the compound of Example 18, 15 ml of 30% hydrogen bromide-acetic acid solution is added and the resultant is stirred at 100° C. for 4.1 hours. Aqueous sodium hydroxide solution is added and the resultant is subjected to extraction with dichloromethane. The organic layer is washed and dried, followed by purification with silica gel column chromatography (ethyl acetate:methanol=7:1) to obtain 1.3 g of the captioned compound in the form of crystals.

IR(KBr) cm$^{-1}$:1502,1431,750

$^1$HNMR(CDCl3) δ:7.47(1H,m),7.18(1H,m),7.02–6.85 (2H,m),4.44(2H,s),3.53(2H,t,J=7.0),3.49(2H,t,J=6.1),2.78 (3H,s),2.23(2H,m)

MS: 306(M+)

Example 20

N-(3-methoxypropyl)glycine ethyl ester (20)

MeO(CH$_2$)$_3$NHCH$_2$CO$_2$Et    (20)

A solution containing 52 g of 3-methoxypropylamine in 100 ml of tetrahydrofuran is immersed in iced water and a solution containing 27 g of ethyl bromoacetate in 30 ml of tetrahydrofuran is added dropwise for 1 hour. The resultant is stirred at room temperature for 2 hours and the solvent and the excess 3-methoxypropylamine are evaporated under reduced pressure. The residue is purified by silica gel column chromatography (ethanol:dichloromethane=1:20) to obtain 19 g of the captioned compound in the form of colorless oil.

IR(Neat) cm$^{-1}$:2982,2938,1736,1452,1185,1122

$^1$HNMR(CDCl3) δ:4.20(2H,q,J=7.2),3.48(2H,t,J=6.2), 3.44(2H,s),3.34(3H,s)2.76(2H,t,J=6.8), 1.81(2H,quint,J= 6.6),1.28(3H,t,J=7.2)

Example 21

N-(3-methoxypropyl)alanine ethyl ester (21)

MeO(CH$_2$)$_3$NHCHMeCO$_2$Et    (21)

The same procedure as in Example 20 is repeated except that ethyl 2-chloropropionate is used in place of ethyl bromoacetate to obtain (21) in the form of colorless oil.

IR(Neat) cm$^{-1}$:2934,2876,1742,1464,1373,1195,1120

$^1$HNMR(CDCl3) δ:4.18(2H,q,J=7.2),3.44(2H,t,J=6.4), 3.32(3H,s),3.32(1H,q,J=7.1),2.64(2H,td,J=6.8,2.2), 1.74 (2H,quint,J=6.6),1.29(3H,d,J=7.1),1.28(3H,t,J=7.2)

Example 22

N-(5-chloro-2-nitrophenyl)-N-(3-methoxypropyl)glycine methyl ester (22)

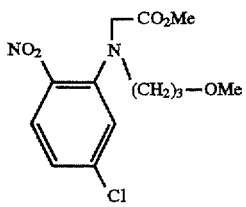

To 35 ml of ethanol and 4.5 ml of water, 3.3 g of the compound of Example 20, 3.9 g of 2,4-dichloronitrobenzene and 3.0 g of sodium hydrogen carbonate are added and the resulting mixture is heated to reflux for 1 week. After converting the resultant to acidic condition by adding 2N hydrochloric acid, the resultant is subjected to extraction with dichloromethane. The organic layer is washed with water and dried. The solvent is then evaporated and the residue is dissolved in 40 ml of methanol. The solution is immersed in iced water and 4.0 g of thionyl chloride is added dropwise for 5 minutes. After stirring the resulting mixture for 30 minutes, the mixture is stirred at room temperature overnight. The solvent is evaporated under reduced pressure and the residue is purified by silica gel column chromatography (ethyl acetate:dichloromethane=20:1) to obtain 4.7 g of the captioned compound in the form of orange oil.

IR(Neat) cm$^{-1}$:2984,1744,1522,1197,1118,1031

$^1$HNMR(CDCl3) δ:7.71(1H,d,J=8.8),7.33(1H,d,J=2.2), 6.87(1H,dd,J=8.8,2.2),3.88(2H,s),3.71(3H,s), 3.41(4H,t,J=6.2),3.31(3H,s),1.78(2H,quint,J=6.2)

Example 23

N-(5-fluoro-2-nitrophenyl)-N-(3-methoxypropyl)glycine methyl ester (23)

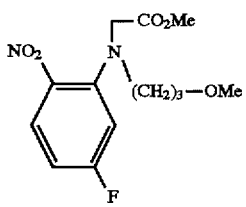

The same procedure as in Example 22 is repeated except that 2,4-difluoronitrobenzene is used in place of 2,4-dichloronitrobenzene to obtain (23) in the form of orange oil.

IR(Neat) cm$^{-1}$:2934,1748,1622,1520,1205,969,837

$^1$HNMR(CDCl3) δ:7.84(1H,m),7.00(1H,dd,J=11.0,2.4), 6.68(1H,m),3.89(2H,s)3.71(3H,s),3.42(4H,t,J=6.0), 3.31(3H,s),1.80(2H,quint,J=6.0)

Example 24

N-(4-fluoro-2-nitrophenyl)-N-(3-methoxypropyl)glycine methyl ester (24)

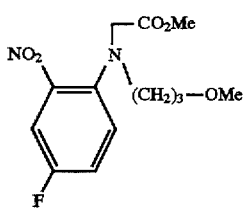

The same procedure as in Example 22 is repeated except that 2,5-difluoronitrobenzene is used in place of 2,4-dichloronitrobenzene to obtain (24) in the form of orange oil.

IR(Neat) cm$^{-1}$:2934,1742,1535,1499,1193,1120

$^1$HNMR(CDCl3) δ:7.46(3H,m),3.88(2H,s),3.68(3H,s), 3.36(4H,t,J=6.2),3.28(3H,s),1.68(2H,quint,J=6.2)

Example 25

N-(3-methoxypropyl)-N-(2-nitrophenyl)alanine methyl ester (25)

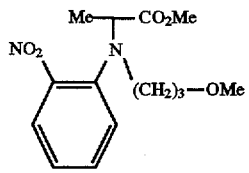

The same procedure as in Example 22 is repeated except that 2-chloronitrobenzene is used in place of 2,4-dichloronitrobenzene and that (21) is used in place of (20) to obtain (25) in the form of orange oil.

IR(Neat) cm$^{-1}$:2954,1730,1522,1357,1120,777

$^1$HNMR(CDCl3) δ:7.49(2H,m),7.18(2H,m),3.87(1H,m), 3.66(3H,s),3.37(4H,m),3.27(3H,s),1.65(2H,quint,J=6.8), 1.45(3H,d,J=7.2)

Example 26

7-chloro-1,2-dihydro-1-(3-methoxypropyl) quinoxalin-3 (4H)one (26)

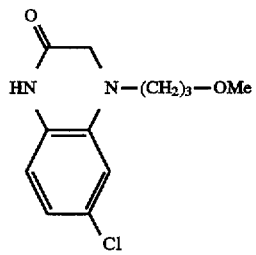

To 50 ml of water, 5.6 g of reduced iron and 5 ml of acetic acid are added and the resulting mixture is heated to 80° C. To the resultant, a solution of the compound of Example 22 in 50 ml of ethanol is added and the mixture is stirred for 1 hour. The precipitates are separated by filtration and subjected to extraction with dichloromethane. The organic layer is washed with water and dried. The solvent is evaporated and the residue is recrystallized from ethyl acetate to obtain 2.7 of the captioned compound in the form of white crystals.

mp:190°–200° C.

IR(KBr) cm$^{-1}$:2930,1684,1518,1108,835

$^1$HNMR(CDCl3) δ:8.72(1H,brs),6.65(3H,m),3.88(2H,s), 3.44(2H,t,J=5.7),3.36(3H,s),3.33(2H,t,J=7.2), 1.86(2H, quint,J=6.6)

MS: 254(M+)

Example 27

7-chloro-1,2-dihydro-1-(3-methoxypropyl) quinoxaline-3 (4H)thione (27)

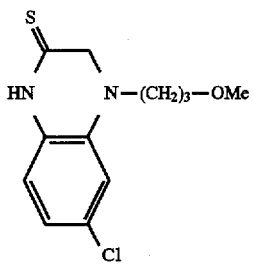
(27)

Fifteen milliliters of Diglyme is added to 2.3 g of the compound of Example 26, 2.3 g of phosphorus pentasulfide and 1.2 g of sodium hydrogen carbonate, and the resulting mixture is stirred at 80° C. for 4 hours. The solvent is evaporated and water is added. The formed precipitates are separated by filtration and washed with water to obtain 2.4 g of the captioned compound in the form of yellow crystals.

mp:140°–142° C.

IR(KBr) cm$^{-1}$:3174,2894,1584,1547,1400,1106,1009, 806

$^1$HNMR(CDCl3) δ:9.89(1H,brs),6.68(3H,m),4.23(2H,s), 3.47(2H,t,J=5.9),3.36(3H,s),3.33(2H,t,J=7.2), 1.85(2H, quint,J=6.6)

MS: 270(M+)

Examples 28–33

The same procedure as in Example 26 is repeated except that 23 is used in place of 22 to obtain compound 28; that 24 is used in place of 22 to obtain compound 29; or that 25 is used in place of 22 to obtain compound 30. The same procedure as in Example 27 is repeated except that 28 is used in place of 26 to obtain compound 31; 29 is used in place of 26 to obtain compound 32; or 30 is used in place of 26 to obtain compound 33.

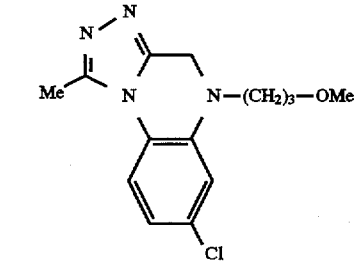

| Compound | Y | R²R³ | R⁴ | R⁵ |
| --- | --- | --- | --- | --- |
| 28 | O | 7-F | H | H |
| 29 | O | 6-F | H | H |
| 30 | O | H | Me | H |
| 31 | S | 7-F | H | H |
| 32 | S | 6-F | H | H |
| 33 | S | H | Me | H |

28: 7-fluoro-1,2-dihydro-1-(3-methoxypropyl) quinoxalin-3(4H)one
29: 6-fluoro-1,2-dihydro-1-(3-methoxypropyl) quinoxalin-3(4H)one
30: 1,2-dihydro-1-(3-methoxypropyl)-2-methylquinoxalin-3(4H)one
31: 7-fluoro-1,2-dihydro-1-(3-methoxypropyl) quinoxaline-3(4H)thione
32: 6-fluoro-1,2-dihydro-1-(3-methoxypropyl) quinoxaline-3(4H)thione- 2-methylquinoxaline-3(4H)thione These compounds have the following physical properties:
Compound Spectrum Data
28: White Crystal
mp:174°–177° C.
IR(KBr) cm$^{-1}$:2882,1680,1522,1417,1309,1114,826
$^1$HNMR(CDCl3) δ:9.78(1H,brs),6.73(1H,m),6.42(2H, m), 4.24(2H,s),3.43(2H,t,J=5.7),3.35(3H,s),3.32(2H,t,J= 6.6), 1.84(2H,quint,J=5.7)

29: White Crystal
mp:131°–133° C.
IR(KBr) cm$^{-1}$:2884,1690,1531,1406,1270,859,793
$^1$HNMR(CDCl3) δ:8.68(1H,brs),6.69(1H,s),6.62(2H,m), 3.80(2H,s),3.46(2H,t,J=5.7),3.35(3H,s),3.32(2H,t,J=6.0), 1.78(2H,quint,J=5.9)

30: Colorless Oil
IR(Neat) cm$^{-1}$:2930,1684,1510,1388,1243,1118,745
$^1$HNMR(CDCl3) δ:8.74(1H,brs),6.98(1H,m),6.77(3H, m), 3.99(1H,q,J=6.8),3.44(4H,t,J=5.9),3.34(3H,s), 1.87(2H, quint,J=5.9)1.19(3H,d,J=6.8)
MS: 234(M+)

31: Yellow Crystal
IR(KBr) cm$^{-1}$:2898,1560,1512,1406,1203,1102,808,
$^1$HNMR(CDCl3) δ:9.78(1H,brs),6.81–6.36(3H,m),4.24 (2H,s),3.43(2H,t,J=5.7),3.35(3H,s), 3.32(2H,t,J=7.6),1.84 (2H,quint,J=6.8)
MS: 254(M+)

32: Yellow Crystal
IR(KBr) cm$^{-1}$:2932,1557,1510,1270,1139,1106,845
$^1$HNMR(CDCl3) δ:9.76(1H,brs),6.68(3H,m),4.16(2H,s), 3.43(2H,t,J=5.7)3.35(3H,s),3.31(2H,t,J=7.9), 1.83(2H, quint,J=6.4)

33: Yellow Crystal
IR(KBr) cm$^{-1}$:3108,2988,1547,1512,1392,1303,1104, 893
$^1$HNMR(CDCl3) δ:9.77(1H,brs),7.09(1H,m),6.80(2H,s), 4.45(1H,q,J=6.8),3.43(2H,m),3.35(3H,s),3.14(2H,m), 1.86 (2H,quint,J=6.6),1.25(3H,d,J=6.8)
MS: 250(M+)

Example 34

7-chloro-4,5-dihydro-1-methyl-5-(3-methoxypropyl) [1,2,4] triazolo[4,3-a]quinoxaline (34)

To 2.3 g of the compound of Example 27 and 1.8 g of acetohydrazide, 24 ml of n-butanol is added and the resulting mixture is heated to reflux for 8 hours. Water is added thereto and the resultant is subjected to extraction with dichloromethane. The organic layer is washed with water and dried. The resultant is purified by silica gel column chromatography (ethanol:dichloromethane=1:10) to obtain 1.8 g of the captioned compound in the form of pale brown crystals.

mp:101°–104° C.

Elementary Analysis:as C14H17N4OCl Calcd.:C, 57.44;H,5.85;N,19.14;Cl,12.11 Found :C,57.68;H,5.97;N, 19.33;Cl,12.35

IR(KBr) cm$^{-1}$:2878,1549,1512,1441,1199,1114,1004,

¹HNMR(CDCl3) δ:7.37(1H,d,J=8.3),6.95(1H,d,J=2.8), 6.86(1H,dd,J=8.3,2.8),4.46(2H,s),3.44(4H,t,J=5.7), 3.36 (3H,s),2.76(3H,s),1.91(2H,quint,J=6.0)
MS: 292(M+)

Examples 35–41

The same procedure as in Example 18 is repeated except that 16 is used in place of 13 to obtain compound 35; that 17 is used in place of 13 to obtain compound 36; that 15 is used in place of 13 to obtain compound 37; or that ethoxybutyl bromide is used in place of ethoxypropyl bromide to obtain compound 38. The same procedure as in Example 34 is repeated except that 31 is used in place of 27 to obtain compound 39; that 32 is used in place of 27 to obtain compound 40; or that 33 is used in place of 27 to obtain compound 41.

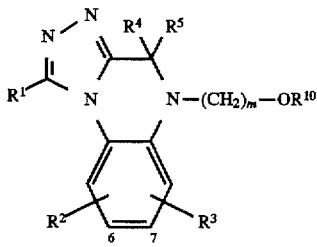

| Compound | R¹ | R²R³ | R⁴ | R⁵ | m | R10 |
|---|---|---|---|---|---|---|
| 35 | Et | H | H | H | 3 | Et |
| 36 | Pr | H | H | H | 3 | Et |
| 37 | Me | H | Me | Me | 3 | Et |
| 38 | Me | H | H | H | 4 | Et |
| 39 | Me | 7-F | H | H | 3 | Me |
| 40 | Me | 8-F | H | H | 3 | Me |
| 41 | Me | H | Me | H | 3 | Me |

35: 1-ethyl-4,5-dihydro-5-(3-ethoxypropyl) [1,2,4]triazolo[4,3-a]quinoxaline
36: 4,5-dihydro-1-propyl-5-(3-ethoxypropyl) [1,2,4]triazolo[4,3-a]quinoxaline
37: 4,5-dihydro-1,4,4-trimethyl-5-(3-ethoxypropyl) [1,2,4]triazolo[4,3-a]quinoxaline
38: 4,5-dihydro-1-methyl-5-(4-ethoxybutyl) [1,2,4]triazolo[4,3-a]quinoxaline
39: 7-fluoro-4,5-dihydro-1-methyl-5-(3-methoxypropyl) [1,2,4]triazolo[4,3-a]quinoxaline
40: 8-fluoro-4,5-dihydro-1-methyl-5-(3-methoxypropyl) [1,2,4]triazolo[4,3-a]quinoxaline
41: 4,5-dihydro-1,4-dimethyl-5-(3-methoxypropyl) [1,2,4]triazolo[4,3-a]quinoxaline The above-described compounds have the following physical properties:
Compound Spectrum Data
35:Yellow Oil
IR(Neat) cm⁻¹: 3414,2978,2872,1611,1557,1502,1473, 1437,1112,748,427
¹HNMR(CDCl3) δ:7.49–6.91(4H,m),4.43(2H,s), 3.61–3.37(6H,m),3.12(2H,q,J=7.3),2.04–1.75(2H,m), 1.50 (3H,t,J=7.5),1.22(3H,t,J=6.8)
MS: 286(M+)
36:Yellow Oil
IR(Neat) cm⁻¹:3500,2972,2874,1502,1435,748,480
¹HNMR(CDCl3) δ:7.49–6.92(4H,m),4.42(2H,s), 3.60–3.15(6H,m),3.02(2H,q,J=8.1),2.17–1.75(4H,m), 1.31–1.01(6H,m)
MS: 300(M+)
37:Colorless Oil
IR(Neat) cm⁻¹:2976,1680,1539,1504,1187,750
¹HNMR(CDCl3) δ:7.50–7.15(2H,m),6.95(2H,d,J=7.7), 3.48(2H,q,J=7.0),3.44(4H,t,J=6.6),2.78(3H,s), 1.82(2H,quint,J=6.6),1.62(6H,s),1.22(3H,t,J=7.0)

MS: 300(M+)
38:Colorless Oil
IR(Neat) cm⁻¹: 3414,2976,2938,2868,1611,1557,1504, 1433,1112,750
¹HNMR(CDCl3) δ:7.6–6.8(4H,m),4.42(2H,s),3.65–3.2 (6H,m),2.77(3H,s)1.9–1.5(4H,m),1.20(2H,t,J=6.9)
MS: 286(M+)
39:White Crystal
mp:112°–115° C.
IR(KBr) cm⁻¹:2930,1555,1512,1429,1313,1116,855
¹HNMR(CDCl3) δ:7.40(1H,dd,J=8.8,5.5),6.70(2H,m), 4.46(2H,s),3.44(4H,t,J=6.2),3.36(3H,s),2.76(3H,s), 1.84 (2H,quint,J=6.0)
MS: 276(M+)
40:White Crystal
mp:140°–142° C.
IR(KBr) cm⁻¹:2928,1557,1506,1193,1116,849,
¹HNMR(CDCl3) δ:7.21(1H,d,J=9.0),6.89(2H,m),4.38 (2H,s), 3.44(4H,m),3.35(3H,s),2.77(3H,s),1.89(2H,quint,J= 6.4)
MS: 276(M+)
41:Colorless Oil
IR(Neat) cm⁻¹:2930,1553,1504,1429,1118,750
¹HNMR(CDCl3) δ:7.46(1H,d,J=7.6),7.22(1H,d,J=8.2), 6.90(2H,m),4.85(1H,q,J=6.8),3.40(4H,m),3.33(3H,s), 2.78 (3H,s),1.88(2H,quint,J=6.2),1.27(3H,d,J=6.8)
MS: 272(M+)

Example 42

4,5-dihydro-1-methyl-5-[3-[4-(diphenylmethyl) piperazin-1-yl]ethyl][1,2,4]triazolo[4,3-a]quinoxaline (42)

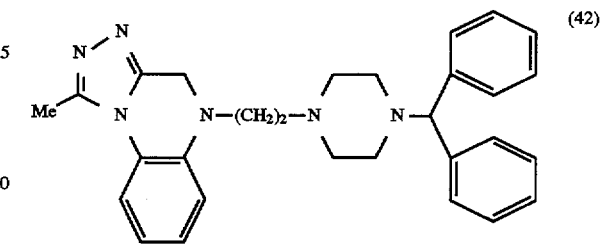

To 0.13 g of the compound of Example 13 and 0.40 g of [4-(diphenylmethyl)piperazin-1-yl]ethylchloride hydrochloric acid salt, 4 ml of dimethylformamide is added and then 60% sodium hydride and 35% potassium hydride are added at room temperature. The resulting mixture is stirred at 60° C. for 3 hours and the disappearance of the compound of Example 13 is confirmed. Water is added to the mixture and the resultant is subjected to extraction with ethyl acetate. The organic layer is washed with water and dried. The solvent is evaporated under reduced pressure and the residue is purified by silica gel column chromatography (ethyl acetate:methanol=6:1) to obtain 0.19 g of oil.
IR(KBr) cm⁻¹:2814,1504,1009,748,708
¹HNMR(CDCl3) δ:7.45(1H,dd,J=8.3,1.5),7.41(4H,AB, J=7.3), 7.27(4H,t,J=7.3),7.21(1H,m),7.17(2H,t,J=7.3), 6.92–6.88(2H,m),4.51(2H,s),4.22(1H,s),3.47(2H,t,J=6.8), 2.76(3H,s),2.66(2H,t,J=6.8),2.55(4H,brs),2.42(4H,brs)
MS: 464(M+)

Example 43

4,5-dihydro-1-methyl-5-[3-[4-(diphenylmethyl)piperazin-1-yl]ethyl][1,2,4]triazolo [4,3-a]quinoxaline fumaric acid salt (43)

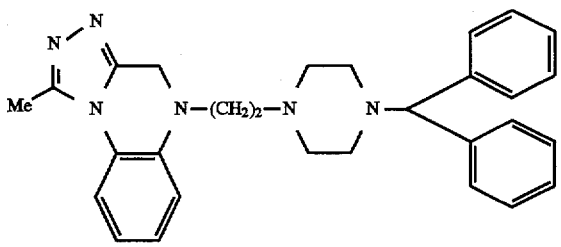

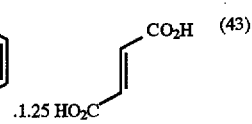
(43)

In ethanol, 0.18 g of the compound of Example 42 is dissolved and 0.093 g of fumaric acid in ethanol is added to the resulting solution. The mixture is condensed and the residue is recrystallized from isopropanol to obtain 0.25 g of the captioned compound in the form of pale flesh color crystals.

mp:171°–172° C.

Elementary Analysis:as C29H32N6.1.25C4H4O4 Calcd.:C;66.98,H;6.12,N;13.78 Found :C;66.88,H;6.17, N;13.51

IR(KBr) cm$^{-1}$:1702,1502,1276,984,752,648

Example 44

4,5-dihydro-1-methyl-5-[3-[4-(diphenylmethyl)piperazin-1-yl]propyl][1,2,4]triazolo[4,3-a]quinoxaline (44)

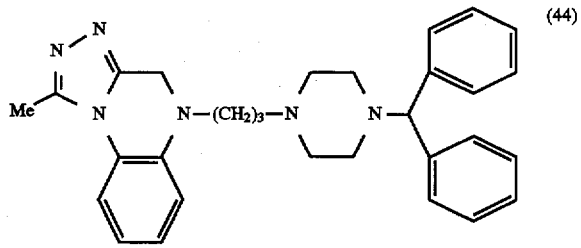
(44)

In 20 ml of anhydrous tetrahydrofuran, 1.12 g of the compound of Example 5 is dissolved and 10 ml of 0.5M aluminum hydride in tetrahydrofuran is added thereto, followed by stirring for 3 hours. After water and ethyl acetate are added to the resulting mixture, the mixture is subjected to filtration using Celite to separate organic layer. After condensing the obtained organic layer, the resultant is subjected to column chromatography to obtain 0.21 g of the captioned compound.

mp:175°–185° C.

Elementary Analysis:as C30H34N6 Calcd.:C,75.28;H, 7.16;N,17.56 Found :C,75.01;H,7.14;N,17.36

IR(KBr) cm$^{-1}$:2808,1508,1011,746,704

$^1$HNMR(CDCl3) δ:7.46–7.41(5H,m),7.27(4H,t,J=7.3), 7.17(3H,td,J=7.6,1.4),6.94(1H,d,J=8.3),6.89(1H,t,J=7.8), 4.42(2H,s),4.22(1H,s),3.37(2H,t,J=7.3),2.77(3H,s), 2.47 (8H,brs),2.41(2H,t,J=7.3),1.82(2H,quint,J=7.3)

MS: 478(M+)

Example 45

4,5-dihydro-1-methyl-5-[3-[4-[bis(4-fluorophenyl)methyl] piperazin-1-yl]propyl][1,2,4]triazolo[4,3-a]quinoxaline (45)

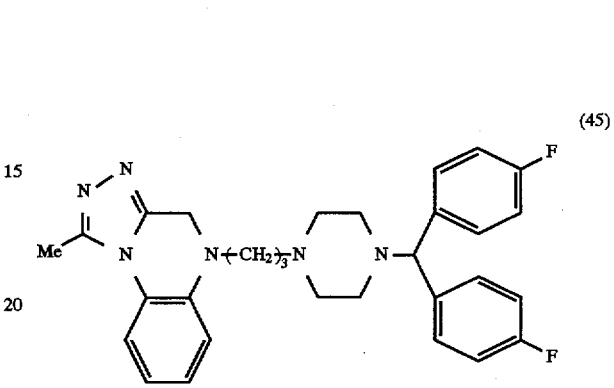
(45)

Five milliliters of 2-butanone is added to 0.50 g of the compound of Example 19, 0.52 g of 1-[bis(4-fluorophenyl) methyl]piperazine and 0.27 g of sodium carbonate, and the resulting mixture is heated to reflux for 5.5 hours. After evaporating solvent, water is added and the resultant is subjected to extraction with dichloromethane. The organic layer is washed with water and dried, and the residue is purified by silica gel column chromatography (ethyl acetate:methanol=6:1). The product is recrystallized from ethyl acetate to obtain 0.49 g of the captioned compound in the form of pale flesh color crystals.

mp:144°–146° C.

Elementary Analysis:as C30H32N6F2 Calcd.:C,70.02;H, 6.27;N,16.33 Found :C,69.63;H,6.31;N,16.36

IR(KBr) cm$^{-1}$:1506,1202,826,746

$^1$HNMR(CDCl3) δ:7.45(1H,dd,J=7.9,1.2),7.34(4H,m), 7.19(1H,td,J=7.9,1.2),6.96(4H,t,J=8.9),6.94(1H,m), 6.89 (1H,t,J=7.9),4.42(2H,s),4.22(1H,s),3.37(2H,t,J=7.0), 2.77 (3H,s),2.46(8H,brs),2.40(2H,t,J=7.0), 1.82(2H,quint,J=7.0)

MS: 514(M+)

Example 46

4,5-dihydro-1-methyl-5-[3-[4-(diphenylmethylene) piperidin-1-yl]propyl][1,2,4]triazolo[4,3-a]quinoxaline (46)

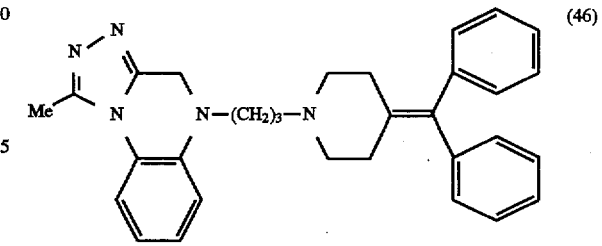
(46)

To 1.0 g of the compound of Example 18, 15 ml of 47% hydrobromic acid is added and the resulting mixture is heated at 110° C. for 1.5 hours. The solvent is evaporated under reduced pressure and the residue is dried. To the residue, 15 ml of dimethylformamide, 0.78 g of sodium carbonate and 0.92 g of 4-(diphenylmethylene)piperidine are added and the mixture is stirred at 90° C. for 1.5 hours. The solvent is evaporated under reduced pressure and dichloromethane and water are added to conduct extraction. The organic layer is washed with water and dried. The solvent is evaporated and the residue is purified by silica gel chromatography (ethyl acetate:methanol=3:2). The product is recrystallized from n-butanol to obtain 1.4 g of the captioned compound in the form of colorless crystals.

mp:204°–205° C.

Elementary Analysis:as C31H33N5 Calcd.:C,78.28;H, 6.99;N,14.73 Found :C,78.14;H,7.10;N,14.65

IR(KBr) cm$^{-1}$:2892,1508,1429,1348,745,704

$^1$HNMR(CDCl3) δ:7.45(1H,dd,J=8.1,1.1),7.28(4H,t,J= 7.0), 7.21(3H,q,J=7.3),7.12(4H,d,J=7.0),6.98(1H,d,J=8.4), 6.90(1H,t,J=7.9),4.44(2H,s),3.41(2H,t,J=7.3),2.77(3H,s), 2.53(4H,brs),2.44(6H,m),1.90(2H,quint,J=7.0)

MS: 475(M+)

Example 47

4,5-dihydro-1-methyl-5-[3-[4-(diphenylmethylene) piperidin-1-yl]propyl][1,2,4]triazolo[4,3-a]quinoxaline tartaric acid salt (47)

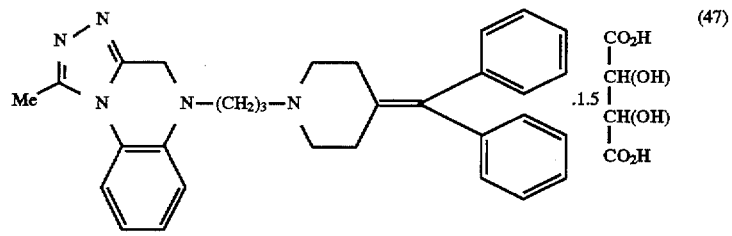

In 150 ml of hot ethanol, 4.78 g of the compound of Example 46 is dissolved and 2.26 g of L-tartaric acid in ethanol is added thereto. After cooling the mixture, precipitated crystals are filtered to obtain 5.93 g of the captioned compound in the form of colorless crystals.

mp:135°–139° C.

Elementary Analysis:as C31H33N5.1.5C4H6O6.1H2O Calcd.:C,61.83;H,6.17;N,9.74 Found :C,61.92;H,6.20;N, 9.68

IR(KBr) cm$^{-1}$:3322,1738,1562,1504,1309,1267,1216, 1137,681

Example 48

4,5-dihydro-1-methyl-5-[3-[4-(diphenylmethylene) piperidin-1-yl]propyl][1,2,4]triazolo[4,3-a]quinoxaline malic acid salt (48)

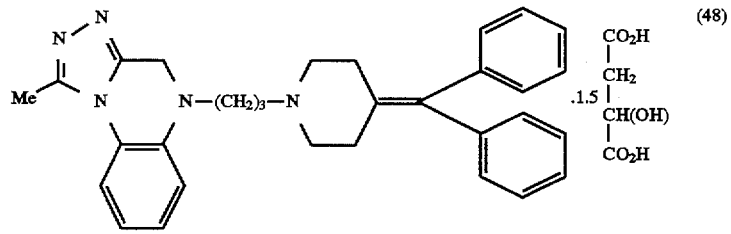

In 50 ml of hot ethanol, 4.45 g of the compound of Example 46 is added and 1.90 g of L-malic acid in ethanol is added thereto. After cooling the mixture, precipitated crystals are filtered to obtain 3.88 g of the captioned compound in the form of colorless crystals.

mp:130°–133° C.

Elementary Analysis:as C31H33N5.1.5C4H6O5.0.5H2O Calcd.:C,64.80;H,6.32;N,10.21 Found :C,64.51;H,6.50;N, 10.38

IR(KBr) cm$^{-1}$:3420,1719,1562,1504,1433,1284,706

Example 49

4,5-dihydro-1-methyl-5-[3-[4-(3-indolyl) piperidine-1-yl] propyl][1,2,4]triazolo[4,3-a]quinoxaline (49)

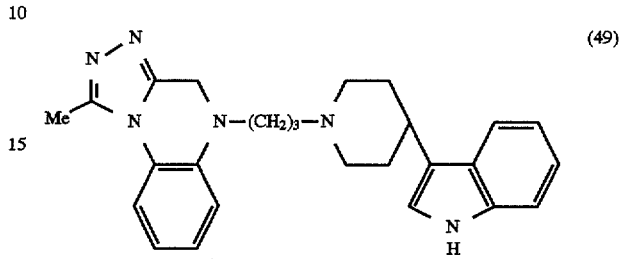

The same procedure as in Example 46 is repeated except that 4-(3-indolyl)piperidine is used in place of 4-(diphenylmethylene)piperidine to obtain the captioned compound in the form of white crystals.

mp:193°–196° C.

Elementary Analysis:as C26H30N6 Calcd.:C,73.21;H, 7.09;N,19.70 Found :C,72.83;H,7.05;N,19.50

IR(KBr) cm$^{-1}$:3400,3178,2924,1562,1504,1425,1352, 745

$^1$HNMR(CDCl3) δ:8.09(1H,s),7.65(1H,AB,J=8.3), 7.46 (1H,d,J=6.8),7.36(1H,AB,J=8.3),7.25–7.16(2H,m),7.10 (1H,t,J=7.8),7.00–6.99(2H,m),6.90(1H,t,J=8.3),4.46(2H,s), 3.43(2H,t,J=7.3), 3.04(2H,d,J=11.7),2.85(1H,tt,J=11.7,3.7), 2.78(3H,s), 2.46(2H,t,J=7.3),2.18–2.07(4H,m),1.94–1.77 (4H,m)

MS: 426(M+)

Example 50

4,5-dihydro-1-methyl-5-[3-[4-(3-indolyl) piperidin-1-yl] propyl][1,2,4]triazolo[4,3-a]quinoxaline fumaric acid salt (50)

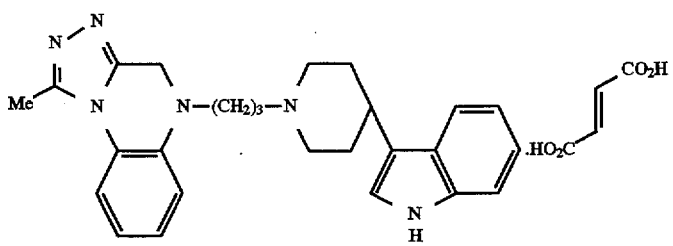
(50)

In 20 ml of ethanol/chloroform (1:1), 3.50 g of the compound of Example 49 is dissolved, and 0.96 g of fumaric acid in 5 ml of ethanol is added thereto. The solvent is evaporated and the product is crystallized to obtain 4.45 g of the captioned compound in the form of white crystals.

mp:145°–147° C.

Elementary Analysis:as $C_{26}H_{30}N_6 \cdot C_4H_4O_4$ Calcd.:C, 66.40;H,6.32;N,15.49 Found :C,66.38;H,6.21;N,15.46

IR(KBr) $cm^{-1}$:3410,1678,1562,1433,1342,1228,982,748, 648

Examples 51–68

The same procedure as in Example 49 is repeated except that 38 is used in place of 18 to obtain compound 51; that 35 is used in place of 18 to obtain compound 52; that 36 is used in place of 18 to obtain compound 53; that 4-(5-methoxy-3-indolyl)piperidine is used in place of 4-(3-indolyl) piperidine to obtain compound 54; that 4-(5-chloro-3-indolyl)piperidine is used in place of 4-(3-indolyl)piperidine to obtain compound 55; that 4-(5-bromo-3-indolyl) piperidine is used in place of 4-(3-indolyl)piperidine to obtain compound 56; that 4-(5-fluoro-3-indolyl)piperidine is used in place of 4-(3-indolyl)piperidine to obtain compound 57; that 4-(5-methyl-3-indolyl)piperidine is used in place of 4-(3-indolyl)piperidine to obtain compound 58; that 4-(6-methoxy-3-indolyl)piperidine is used in place of 4-(3-indolyl)piperidine to obtain compound 59; that 4-(6-methyl-3-indolyl)piperidine is used in place of 4-(3-indolyl) piperidine to obtain compound 60; that 4-(6-fluoro-3-indolyl)piperidine is used in place of 4-(3-indolyl)piperidine to obtain compound 61; that 4-(2-methyl-3-indolyl) piperidine is used in place of 4-(3-indolyl)piperidine to obtain compound 62; that 4-[1,2,3,6-tetrahydro-4-(3-indolyl)pyridine is used in place of 4-(3-indolyl)piperidine to obtain compound 63; that 4-(1-ethyl-3-indolyl)piperidine is used in place of 4-(3-indolyl)piperidine to obtain compound 64; that 34 is used in place of 18 to obtain compound 65; that 39 is used in place of 18 to obtain compound 66; that 40 is used in place of 18 to obtain compound 67; or that 41 is used in place of 18 to obtain compound 68.

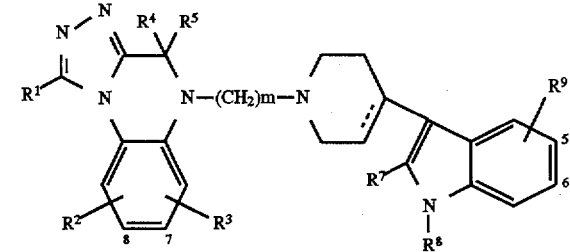

| Compound | $R^1$ | $R^2$ | $R^3$ | $R^4$ | $R^5$ | m | $R^7$ | $R^8$ | $R^9$ |
|---|---|---|---|---|---|---|---|---|---|
| 51 | Me | H | H | H | H | 4 | — | H | H H |
| 52 | Et | H | H | H | H | 3 | — | H | H H |
| 53 | Pr | H | H | H | H | 3 | — | H | H H |
| 54 | Me | H | H | H | H | 3 | — | H | H 5-MeO |
| 55 | Me | H | H | H | H | 3 | — | H | H 5-Cl |
| 56 | Me | H | H | H | H | 3 | — | H | H 5-Br |
| 57 | Me | H | H | H | H | 3 | — | H | H 5-F |
| 58 | Me | H | H | H | H | 3 | — | H | H 5-Me |
| 59 | Me | H | H | H | H | 3 | — | H | H 6-MeO |
| 60 | Me | H | H | H | H | 3 | — | H | H 6-Me |
| 61 | Me | H | H | H | H | 3 | — | H | H 6-F |
| 62 | Me | H | H | H | H | 3 | — | Me | H H |
| 63 | Me | H | H | H | H | 3 | — | H | H H |
| 64 | Me | H | H | H | H | 3 | — | H | Et H |
| 65 | Me | 7-Cl | H | H | H | 3 | — | H | H H |
| 66 | Me | 7-F | H | H | H | 3 | — | H | H H |
| 67 | Me | 8-F | H | H | H | 3 | — | H | H H |
| 68 | Me | H | Me | H | H | 3 | — | H | H H |

51: 4,5-dihydro-1-methyl-5-[3-[4-(3-indolyl) piperidin-1-yl]butyl][1,2,4]triazolo[4,3-a]quinoxaline
52: 1-ethyl-4,5-dihydro-5-[3-[4-(3-indolyl) piperidin-1-yl]propyl][1,2,4]triazolo[4,3-a]quinoxaline
53: 4,5-dihydro-1-propyl-5-[3-[4-(3-indolyl) piperidin-1-yl]propyl][1,2,4]triazolo[4,3-a]quinoxaline
54: 4,5-dihydro-1-methyl-5-[3-[4-(5-methoxy-3-indolyl) piperidin-1-yl]propyl][1,2,4]triazolo[4,3-a]quinoxaline
55: 4,5-dihydro-1-methyl-5-[3-[4-(5-chloro-3-indolyl) piperidin-1-yl]propyl][1,2,4]triazolo[4,3-a]quinoxaline
56: 4,5-dihydro-1-methyl-5-[3-[4-(5-bromo-3-indolyl) piperidin-1-yl]propyl][1,2,4]triazolo[4,3-a]quinoxaline
57: 4,5-dihydro-1-methyl-5-[3-[4-(5-fluoro-3-indolyl) piperidin-1-yl]propyl][1,2,4]triazolo[4,3-a]quinoxaline
58: 4,5-dihydro-1-methyl-5-[3-[4-(5-methyl-3-indolyl) piperidin-1-yl]propyl][1,2,4]triazolo[4,3-a]quinoxaline
59: 4,5-dihydro-1-methyl-5-[3-[4-(6-methoxy-3-indolyl) piperidin-1-yl]propyl][1,2,4]triazolo[4,3-a]quinoxaline
60: 4,5-dihydro-1-methyl-5-[3-[4-(6-methyl-3-indolyl) piperidin-1-yl]propyl][1,2,4]triazolo[4,3-a]quinoxaline
61: 4,5-dihydro-1-methyl-5-[3-[4-(6-fluoro-3-indolyl) piperidin-1-yl]propyl][1,2,4]triazolo[4,3-a]quinoxaline
62: 4,5-dihydro-1-methyl-5-[3-[4-(2-methyl-3-indolyl) piperidin-1-yl]propyl][1,2,4]triazolo[4,3-a]quinoxaline
63: 4,5-dihydro-1-methyl-5-[3-[1,2,3,6-tetrahydro-4-(3-indolyl)pyridin-1-yl]propyl][1,2,4]triazolo[4,3-a] quinoxaline 64: 4,5-dihydro-1-methyl-5-[3-[4-(1-ethyl-3-indolyl) piperidin-1-yl]propyl][1,2,4]triazolo[4,3-a]quinoxaline fumaric acid salt 65: 7-chloro-4,5-dihydro-1-methyl-5-[3-[4-(3-indolyl) piperidin-1-yl]propyl][1,2,4]triazolo[4,3-a]quinoxaline 66: 7-fluoro-4,5-dihydro-1-methyl-5-[3-[4-(3-indolyl) piperidin-1-yl]propyl][1,2,4]triazolo[4,3-a]quinoxaline 67: 8-fluoro-4,5-dihydro-1-methyl-5-[3-[4-(3-indolyl) piperidin-1-yl]propyl][1,2,4]triazolo[4,3-a]quinoxaline fumaric acid salt 68: 4,5-dihydro-1,4-dimethyl-5-[3-[4-(3-indolyl) piperidin-1-yl]propyl][1,2,4]triazolo[4,3-a]quinoxaline The physical properties of the above-described compounds are as follows:

Compound Spectrum Data

51: White Crystal
mp: 228°–237° C.
Elementary Analysis: as C27H32N6 Calcd.:C,73.60;H,7.32;N,19.70 Found :C,73.38;H,7.57;N,20.03
IR(KBr) cm$^{-1}$:3430,2934,1502,1460,1431,1383,746
$^1$HNMR(CD3OD) δ:10.8(1H,brs),8.21(1H,dd,J=7.0,1.1), 7.78(1H,d,J=7.7),7.63(1H,m),7.48(1H,d,J=7.1).7.46(1H,m), 7.31(1H,dd,J=6.2,1.1),7.12–6.93(3H,m),4.82(2H,s), 4.43 (2H,t,J=7.7),3.09(2H,m),3.08(3H,s),2.85(1H,m), 2.51(2H,m),2.21(2H,m),2.05(2H,m),1.9–1.8(4H,m),1.75(2H,m)
MS: 440(M+)

52: Pale Yellow Crystal
mp: 202°–205° C.
Elementary Analysis: as C27H32N6.1/4H2O Calcd.:C,72.95;H,7.37;N,18.90 Found :C,72.87;H,7.27;N,18.67
IR(KBr) cm$^{-1}$:3420,3168,2930,1562,1502,1460,1437,741
$^1$HNMR(CDCl3) δ:8.03(1H,brs),7.65(1H,d,J=8.3), 7.45 (1H,dd,J=6.8,1.2),7.37(1H,d,J=7.8),7.25–7.16(2H,m),7.10 (1H,t,J=6.8),7.00–6.99(2H,m),6.90(1H,t,J=7.3),4.46(2H,s), 3.42,(2H,t,J=7.3), 3.12(2H,q,J=7.3),3.05(2H,d,J=11.7), 2.86 (1H,tt,J=11.7,3.4),2.47(2H,t,J=7.3), 2.18–2.06(4H,m), 1.94–1.74(4H,m),1.51(3H,t,J=7.3)
MS: 440(M+)

53: Pale Yellow Crystal
mp: 186°–188° C.
Elementary Analysis: as C28H34N6 Calcd.:C,73.98;H,7.54;N,18.49 Found :C,74.12;H,7.68;N,18.36
IR(KBr) cm$^{-1}$:3420,3182,2934,1562,1502,1460,1433,1342,739
$^1$HNMR(CDCl3) δ:8.22(1H,s),7.65(1H,d,J=7.8), 7.44 (1H,dd,J=6.8,1.0),7.36(1H,d,J=7.8),7.26–7.16(2H,m),7.10 (1H,t,J=6.8),7.00–6.99(2H,m), 6.91(1H,td,J=7.3,1.0),4.44 (2H,s),3.41(2H,t,J=7.3), 3.08–3.03(4H,m),2.85(1H,t,t,J=11.7,3.4),2.47(2H,t,J=6.8), 2.18–2.03(4H,m),2.00–1.78(6H,m),1.09(3H,t,J=7.3)
MS: 454(M+)

54: Pale Yellow Crystal
mp: 147°–151° C.
Elementary Analysis: as C27H32N6O Calcd.:C,71.30;H,7.06;N,18.40 Found :C,71.53;H,7.17;N,18,63
IR(KBr) cm$^{-1}$:3238,2938,1671,1502,1475,1431,1212,1174,750
$^1$HNMR(CDCl3) δ:7.93(1H,brs),7.46(1H,dd,J=8.1,1.5), 7.27–7.21(2H,m),7.06(1H,d,J=2.2),6.98(2H,m), 6.91(1H,t,J=7.7),6.85(1H,dd,J=8.8,2.2),4.46(2H,s), 3.87(3H,s),3.43 (2H,t,J=7.3),3.06(2H,d,J=11.3), 2.81(1H,m),2.78(3H,s), 2.49(2H,t,J=7.1), 2.18(2H,t-like),2.08(2H,d-like),2.0–1.7 (4H,m)
MS: 457(M+H)+

55: Yellow Crystal
mp: 176°–180° C.
Elementary Analysis: as C26H29N6Cl Calcd.:C,67.74;H,6.34;N,18.23;Cl,7.69 Found :C,67,93;H,6.27;N,18.41;Cl,7.49
IR(KBr) cm$^{-1}$: 2926,1560,1506,1460,1435,1352,1288,895,791,748
$^1$HNMR(CDCl3) δ:8.33(1H,brs),7.57(1H,d,J=2.1), 7.47 (1H,dd,J=7.9,1.2),7.29(1H,J=8.6),7.25(1H,m), 7.12(1H,dd, J=8.7,2.0),7.03(1H,d,J=2.1),6.99(1H,d,J=8.2), 6.93(1H,t,J= 7.0),4.45(2H,s),3.44(2H,t,J=7.0), 3.16(2H,d,J=10.7),2.83 (1H,m),2.79(3H,s),2.60(2H,t-like), 2.30(2H,m),2.10–1.86 (6H,m)
MS: 460(M+)

56: Pale Yellow Crystal
mp: 152°–154° C.
Elementary Analysis: as C26H29N6Br Calcd.:C,61.78;H,5.78;N,16.63;Br,15.81 Found :C,61.97;H,5.89;N,16.74;Br,15.57
IR(KBr) cm$^{-1}$:3218,2938,1562,1504,1454,1433,750
$^1$HNMR(CDCl3) δ:8.38(1H,brs),7.72(1H,s), 7.47(1H,dd, J=8.1,1.4),7.28–7.24(3H,m),7.01–6.99(2H,m),6.94(1H,t,J= 7.8),4.44(2H,s), 3.45(2H,t,J=7.0),3.21(2H,d-like),2.85(1H,m),2.79(3H,s), 2.65(2H,t-like),2.37(2H,m),2.1–1.9(6H,m)
MS: 504(M+)

57: Pale Yellow Crystal
mp: 158°–164° C.
Elementary Analysis: as C26H29N6F Calcd.:C,70.25;H,6.58;N,18.90;F,4.27 Found :C,70.37;H,6.39;N,18.64;F,4.11
IR(KBr) cm$^{-1}$: 3176,2926,1562,1504,1475,1429,1352,1168,936,743
$^1$HNMR(CDCl3) δ:8.29(1H,brs),7.47(1H,dd,J=8.1,1.4), 7.29(1H,dd,J=8.8,4.4),7.25–7.21(2H,m),7.06(1H,d,J=2.1), 7.00(1H,d,J=8.6),6.96(1H,d,J=9.2),6.93(1H,m),4.43(2H,s), 3.46(2H,t,J=6.9),3.28(2H,m),2.87(1H,m),2.79(3H,s), 2.72 (2H,m),2.45(2H,m),2.2–2.0(6H,m)
MS: 444(M+)

58: Pale Yellow Crystal
mp: 207°–212° C.
Elementary Analysis: as C27H32N6 Calcd.:C,73.60;H,7.32;N,19.07 Found :C,73.89;H,7,56;N,19.32
IR(KBr) cm$^{-1}$:3232,1562,1502,1468,1454,1433,750
$^1$HNMR(CDCl3) δ:7.85(1H,s),7.64(1H,d,J=7.9),7.36 (1H,s), 7.31(1H,t,J=7.2),7.20(1H,d,J=8.2),7.11(1H,d,J=8.2), 6.96(1H,s)6.98(1H,t-like),6.90(1H,t,J=8.2), 4.45(2H,s),3.47 (2H,t,J=7.2),3.09(2H,d,J=11.9), 2.83(1H,m),2.77(3H,s), 2.54(2H,t,J=7.6),2.40(3H,s), 2.25(2H,t-like),2.04(2H,m), 1.96(2H,m),1.86(2H,m)
MS: 440(M+)

59: Pale Yellow Crystal
mp: 184°–187° C.
Elementary Analysis: as C27H32N6O Calcd.:C,71.03;H,7.06;N,18.41 Found :C,70.86;H,6.93;N,18.56
IR(KBr) cm$^{-1}$:1562,1504,1460,1425,1162,745
$^1$HNMR(CDCl3) δ:7.88(1H,brs),7.51(1H,d,J=8.8), 7.46 (1H,dd,J=7.8,1.2),7.23(1H,td,J=7.8,1.2), 7.00(1H,d,J=7.8), 6.91(1H,td,J=7.3,1.0),6.88(1H,d,J=1.0), 6.86(1H,d,J=1.4), 6.78(1H,dd,J=8.3,2.2),4.46(2H,s), 3.84(3H,s),3.43(2H,d,J= 7.1),3.05(2H,d-like),2.81(1H,m), 2.78(3H,s),2.48(2H,t,J= 7.1),2.16(2H,t,J=11.5), 2.06(2H,d-like),1.76–1.95(4H,m),
MS: 456(M+)

60: White Crystal
mp: 203°–208° C.
Elementary Analysis: as C27H32N6 Calcd.:C,73.60;H,7.32;N,19.07 Found :C,73.77;H,7.14;N,19.31
IR(KBr) cm$^{-1}$: 3224,2926,1560,1504,1473,1460,1423,1350,799,745
$^1$HNMR(CDCl3) δ:7.86(1H,brs),7.46(1H,dd,J=8.3,1.2), 7.46(1H,dd,J=8.0,1.2),7.23(1H,td,J=8.1,1.2),7.16(1H,s), 7.00(1H,d,J=7.3),6.88–6.95(3H,m),4.46(2H,s), 3.43(2H,t,J=7.3),3.04(2H,d,J=11.2),2.82(1H,m),2.78(3H,s), 2.44–2.48 (5H,m),2.14(2H,t-like),2.07(2H,d-like), 1.76–1.94(4H,m)

MS: 440(M+)

61:Pale Orange Crystal
mp:194°–198° C.

Elementary Analysis:as C26H29N6F Calcd.:C,70.25;H, 6.58;N,18.90;F,4.27 Found :C,70.03;H,6.39;N,18.69;F,4.19

IR(KBr) cm⁻¹: 3204,2938,1560,1502,1460,1435,1350, 1145,797,752

¹HNMR(CDCl3) δ:7.99(1H,brs),7.54(1H,dd,J=8.8,5.4), 7.47(1H,dd,J=8.3,1.5),7.23(1H,td,J=7.8,1.2), 7.04(1H,dd,J=9.8,2.4),6.99(1H,d,J=8.3),6.97(1H,d,J=1.5), 6.84–6.93(2H, m),4.47(2H,s),3.43(2H,t,J=7.1), 3.05(2H,d,J=11.2),2.81 (1H,m),2.79(3H,s),2.47(2H,t,J=7.1), 2.15(2H,t,J=11.7),2.06 (2H,d-like),1.75–1.93(4H,m)

MS: 444(M+)

62:Yellow Crystal
mp:176°–182° C.

Elementary Analysis:as C27H32N6 Calcd.:C,73.60;H, 7.32;N,19.07 Found :C,73.47;H,7.12;N,19.24

IR(KBr) cm⁻¹:1560,1502,1460,1433,745

¹HNMR(CD3OD) δ:7.76(1H,dd,J=8.0,1.2),7.60(1H,d,J=7.8), 7.34(1H,d,J=7.3),7.21(1H,d,J=7.8),7.14(1H,d,J=7.3), 7.02(1H,d,J=7.3),6.97(1H,d,J=7.1),6.90(1H,t,J=7.1), 4.46 (2H,s),3.51(2H,t,J=7.0),3.33(2H,m),2.93(1H,m), 2.83(2H, m),2.77(3H,s),2.57(2H,m),2.37(3H,s),2.35(2H,m), 2.07(2H, m),1.82(2H,m)

MS: 440(M+)

63:Pale Yellow Crystal
mp:161°–168° C.

Elementary Analysis:as C26H28N6 Calcd.:C,73.56;H, 6.65;N,19.80 Found :C,73.44;H,6.73;N,19.93

IR(KBr) cm⁻¹:1504,1431,741

¹HNMR(CDCl3) δ:8.16(1H,brs),7.91(1H,d,J=7.8), 7.47 (1H,dd,J=7.8,1.5),7.38(1H,d,J=8.3),7.3–7.1(4H,m),7.01 (1H,d,J=7.3),6.91(1H,td,J=7.8,1.0), 6.22(1H,brs),4.47(2H, s),3.46(2H,t,J=7.3), 3.24(2H,d,J=2.9),2.79(3H,s),2.76(2H,t, J=5.6), 2.65(2H,brs),2.57(2H,t,J=6.8),1.96(2H,m)

MS: 424(M+)

64:White Crystal
mp:142°–152° C.

Elementary Analysis:as C28H34N6.C4H4O4 Calcd.:C, 67.35;H,6.71;N,14.73 Found :C,67.57;H,6.58;N,14.89

IR(KBr) cm⁻¹: 678,1611,1560,1504,1473,1433,1352, 984,746,646 cm

¹HNMR(CDCl3) δ:7.57(1H,d,J=7.8),7.43(1H,d,J=7.8), 7.30(1H,d, J=8.3),7.25(1H,m),7.19(1H,t,J=7.1),7.08(1H,t, J=7.8),7.0–6.9(2H,m),6.87(1H,s),4.41(2H,s),4.11(2H,q,J=7.3), 3.54(2H,d-like),3.44(2H,t,J=7.0),3.0–2.9(3H,m),2.77 (3H,s),2.62(2H,m),2.4–2.0(6H,m), 1.42(3H,t,J=7.3)

MS: 454(M-C4H4O4)+

65:Pale Flesh Crystal
mp:203°–209 ° C. (Decomposed)

Elementary Analysis:as C26H29N6Cl.0.9H2O Calcd.:C, 65.44;H,6.50;N,17.61 Found :C,65.75;H,6.30;N,17.35

IR(KBr) cm⁻¹:2926,1555,1508,1441,1166,733

¹HNMR(CDCl3) δ:8.07(1H,brs),7.64(1H,d,J=8.0),7.36 (2H,d,J=8.5), 7.18(1H,t,J=7.0),7.10(1H,t,J=7.0),7.00(2H,s), 6.86(1H,dd,J=8.5,2.4),4.49(2H,s),3.43(2H,t,J=7.0),3.0 8(2H,d,J=11.6),2.87(1H,m),2.76(3H,s),2.49(2H,t,J=6.7), 2.21(2H,t,J=11.3),2.09(2H,d,J=12.8),1.92(4H,quint,J=7.0)

MS: 460(M+)

66:White Crystal
mp:181°–184 ° C.

Elementary Analysis:as C26H29N6F.0.8H2O Calcd.:C, 68.04;H,6.72;N,18.31;F,4.14 Found :C,68.32;H,6.54;N, 17.95;F,4.17

IR(KBr) cm⁻¹:2928,1560,1512,1352,1311,1011,745

¹HNMR(CDCl3) δ:8.08(1H,s),7.64(1H,d,J=7.3),7.40 (1H,dd,J=9.2,5.5), 7.36(1H,d,J=7.5),7.18(1H,td,J=7.3,1.2), 7.10(1H,t,J=7.9), 7.01(1H,d,J=2.4),6.79(1H,dd,J=11.0,2.4), 6.59(1H,td,J=8.5, 2.4),4.49(2H,s),3.43(2H,t,J=6.7),3.19(2H, d,J=11.6), 2.88(1H,m),2.76(3H,s),2.51(2H,t,J=6.7),2.24 (2H,t,J=11.6), 2.10(2H,d,J=12.9),1.94(4H,m)

MS: 444(M+)

67:Pale Brown Amorphous

Elementary Analysis:as C26H29N6F.C4H4O4 Calcd.:C, 64.27;H,5.93;N,14.99;F,3.39 Found :C,64.15;H,6.08;N, 14.85;F,3.57

IR(KBr) cm⁻¹:2928,1562,1419,1193,743

¹HNMR(CDCl3) δ:8.10(1H,s),7.74(1H,m),7.62(1H,dd, J=7.9, 3.7),7.37(1H,d,J=9.2),7.23(1H,dd,J=7.6,2.4),7.18 (1H,t, J=7.9),7.10(1H,t,J=7.6),7.00(1H,dd,J=11.0,3.7),6.98 (1H, dd,J=7.3,2.4),4.40(2H,s),3.41(2H,t,J=7.3),3.21(2H, brs), 2.78(3H,s),2.39(2H,brs),2.13(2H,d,J=13.5),1.71(6H, m)

MS: 444(M+)

68:Pale Brown Amorphous

Elementary Analysis:as C27H32N6 Calcd.:C,73.60;H, 7.32;N,19.07 Found :C,73.38;H,7.56;N,18.86

IR(KBr) cm⁻¹:2930,1555,1502,1431,1350,1247,745

¹HNMR(CDCl3) δ:8.14(1H,s),7.63(1H,d,J=8.1),7.47 (1H,dd, J=8.1,1.5),7.36(1H,d,J=8.1),7.24(1H,td,J=8.1,1.5), 7.17 (1H,td,J=8.1,1.1),7.09(1H,td,J=7.4,1.1),6.99(1H,m), 6.96 (1H,d,J=8.0),6.91(1H,td,J=7.4,1.1),4.89(1H,q,J=6.6), 3.59 (1H,quint,J=6.6),3.23(1H,quint,J=7.0),3.05(2H,t,J=9.8), 2.88(1H,m),2.78(3H,s),2.47(2H,m),2.17(2H,m),2.07 (2H,d, J=13.1),1.89(4H,m),1.28(3H,d,J=6.6)

MS: 440(M+)

Examples 69–94

The same procedure as in Example 49 is repeated except that in place of 4-(3-indolyl)piperidine, the following compounds are used. That is, 1-[(4-chlorophenyl)phenylmethyl] piperazine is used to obtain compound 69; 1-(4-chlorobenzyl)piperazine is used to obtain compound 70; 1-[1-(1-ethoxyethyl)benzimidazol-2-yl]piperazine is used to obtain compound 71; 1-[1-(1-ethoxyethyl)benzimidazol-2-yl]homopiperazine is used to obtain compound 72; 4-[1-(4-fluorobenzyl)benzimidazol-2-ylamino]piperidine is used to obtain compound 73; 4-(hydroxydiphenylmethyl)piperidine is used to obtain compound 74; 4-[hydroxybis(4-fluorophenyl)methyl]piperidine is used to obtain compound 75; 4-(diphenylmethoxy)piperidine is used to obtain compound 76; 4-[bis(4-fluorophenyl)methylene]piperidine is used to obtain compound 77; 4-(5H-dibenzo[a,d] cyclohepten-5-ylidene)piperidine is used to obtain compound 78; 4-(diphenylmethyl)piperidine is used to obtain compound 79; 4-(1,2-benzisoxazol-3-yl)piperidine is used to obtain compound 80; 4-(2-keto-1-benzimidazolynyl) piperidine is used to obtain compound 81; 4-(1H-pyrrolo[2, 3-b]pyridin-3-yl)piperidine is used to obtain compound 82; 4-(1H-pyrrolo[3,2-c]pyridin-3-yl)piperidine is used to obtain compound 83; 4-(1H-pyrrolo[3,2-b]pyridin-3-yl) piperidine is used to obtain compound 84; 3-(diphenylmethylene)pyrrolidine is used to obtain compound 85; 4-(2-methoxyphenyl)piperazine is used to obtain compound 86; 4-(10,11-dihydro-5H-dibenzo[a,d] cyclohepten-5-ylidene)piperidine is used to obtain compound 87; 4-(6,11-dihydrodibenzo[b.e]oxepin-11-ylidene) piperidine is used to obtain compound 88; or 4-(2-chlorothioxanthen-9-ylidene)piperidine is used to obtain compound 89.

The same procedure as in Example 49 is repeated except that 41 is used in place of 18 and 4-[hydroxybis(4- fluorophenyl)methyl]piperidine is used in place of 4-(3-indolyl)piperidine to obtain compound 90; that 41 is used in place of 18 and 4-[bis(4-fluorophenyl)methylene]piperidine is used in place of 4-(3-indolyl)piperidine to obtain compound 91; that 35 is used in place of 18 and 4-(diphenylmethylene)piperidine is used in place of 4-(3-indolyl)piperidine to obtain compound 92; that 41 is used in place of 18 and 4-(diphenylmethylene)piperidine is used in place of 4-(3-indolyl)piperidine to obtain compound 93; or that 37 is used in place of 18 and 4-(diphenylmethylene) piperidine is used in place of 4-(3-indolyl)piperidine to obtain compound 94.

| Compound | Structural Formula | |
| --- | --- | --- |
| 69 | | (69) |
| 70 | | (70) |
| 71 | | (71) |
| 72 | | (72) |
| 73 | | (73) |

-continued

| Compound | Structural Formula | |
|---|---|---|
| 74 | (structure) | (74) |
| 75 | (structure) | (75) |
| 76 | (structure) | (76) |
| 77 | (structure) | (77) |
| 78 | (structure) | (78) |
| 79 | (structure) | (79) |

-continued

| Compound | Structural Formula | |
|---|---|---|
| 80 | [structure] | (80) |
| 81 | [structure] | (81) |
| 82 | [structure] | (82) |
| 83 | [structure] | (83) |
| 84 | [structure] | (84) |
| 85 | [structure] | (85) |

-continued
| Compound | Structural Formula | |
|---|---|---|
| 86 | 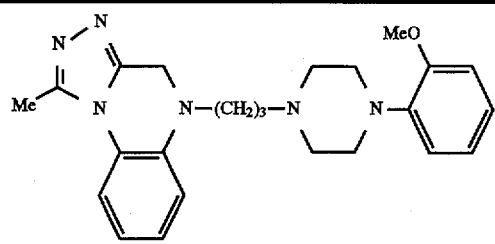 | (86) |
| 87 | 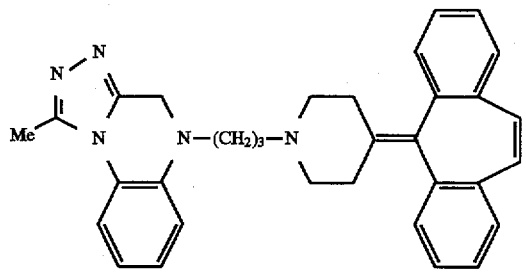 | (87) |
| 88 | 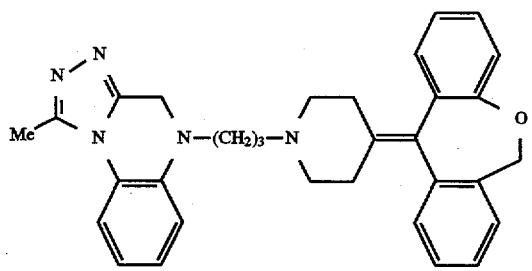 | (88) |
| 89 | 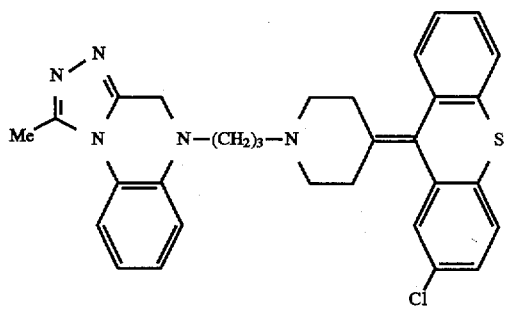 | (89) |
| 90 | 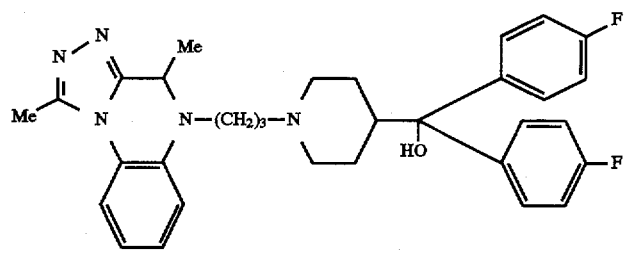 | (90) |
| 91 | 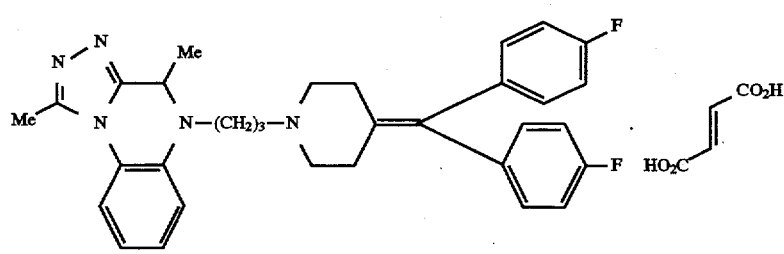 | (91) |

| Compound | Structural Formula |
|---|---|
| 92 | (92) |
| 93 | (93) |
| 94 | (94) |

69: 4,5-dihydro-1-methyl-5-[3-[4-[(4-chlorophenyl) phenylmethyl]piperazin-1-yl]propyl][1,2,4]triazolo[4,3-a]quinoxaline 70: 4,5-dihydro-1-methyl-5-[3-[4-(4-chlorobenzyl) piperazin-1-yl]propyl][1,2,4]triazolo[4,3-a]quinoxaline fumaric acid salt 71: 4,5-dihydro-1-methyl-5-[3-[4-[1-(1-ethoxyethyl) benzimidazol-2-yl]piperazin-1-yl]propyl][1,2,4]triazolo [4,3-a]quinoxaline fumaric acid salt 72: 4,5-dihydro-1-methyl-5-[3-[4-[1-(1-ethoxyethyl) benzimidazol-2-yl]homopiperazin-1-yl]propyl][1,2,4] triazolo[4,3-a]quinoxaline tartaric acid salt 73: 4,5-dihydro-1-methyl-5-[3-[4-[1-(4-fluorobenzyl) benzimidazol-2-ylamino]-piperidin-1-yl]propyl][1,2,4] triazolo[4,3-a]quinoxaline 74: 4,5-dihydro-1-methyl-5-[3-[4-(hydroxydiphenylmethyl) piperidin-1-yl]propyl][1,2,4]triazolo[4,3-a]quinoxaline tartaric acid salt 75: 4,5-dihydro-1-methyl-5-[3-[4-[hydroxybis(4-fluorophenyl)methyl]piperidin-1-yl]propyl][1,2,4] triazolo[4,3-a]quinoxaline tartaric acid salt 76: 4,5-dihydro-1-methyl-5-[3-[4-(diphenylmethoxy) piperidin-1-yl]propyl][1,2,4]triazolo[4,3-a]quinoxaline tartaric acid salt 77: 4,5-dihydro-1-methyl-5-[3-[4-[bis(4-fluorophenyl) methylene]piperidin-1-yl]propyl][1,2,4]triazolo[4,3-a] quinoxaline 78: 4,5-dihydro-1-methyl-5-[3-[4-(5H-dibenzo[a,d] cyclohepten-5-ylidene) piperidin-1-yl]propyl][1,2,4] triazolo[4,3-a]quinoxaline 79: 4,5-dihydro-1-methyl-5-[3-[4-(diphenylmethyl) piperidin-1-yl]propyl][1,2,4]triazolo[4,3-a]quinoxaline 80: 4,5-dihydro-1-methyl-5-[3-[4-(1,2-benzisoxazol-3-yl) piperidin-1-yl]propyl][1,2,4]triazolo[4,3-a]quinoxaline 81: 4,5-dihydro-1-methyl-5-[3-[4-(2-keto-1-benzimidazolynyl) piperidin-1-yl]propyl][1,2,4]triazolo [4,3-a]quinoxaline 82: 4,5-dihydro-1-methyl-5-[3-[4-(1H-pyrrolo[2,3-b] pyridine-3-yl) piperidin-1-yl]propyl][1,2,4]triazolo[4,3-a]quinoxaline fumaric acid salt 83: 4,5-dihydro-1-methyl-5-[3-[4-(1H-pyrrolo[3,2-c] pyridin-3-yl) piperidin-1-yl]propyl][1,2,4]triazolo[4,3-a] quinoxaline 84: 4,5-dihydro-1-methyl-5-[3-[4-(1H-pyrrolo[3,2-b] pyridin-3-yl) piperidin-1-yl]propyl][1,2,4]triazolo[4,3-a] quinoxaline 85: 4,5-dihydro-1-methyl-5-[3-[3-(diphenylmethylene) pyrrolidin-1-yl]propyl][1,2,4]triazolo[4,3-a]quinoxaline 86: 4,5-dihydro-1-methyl-5-[3-[4-(2-methoxyphenyl) piperazin-1-yl]propyl][1,2,4]triazolo[4,3-a]quinoxaline 87: 4,5-dihydro-1-methyl-5-[3-[4-(10,11-dihydro-5H-dibenzo[a,d]cyclohepten-5-ylidene) piperidin-1-yl] propyl][1,2,4]triazolo[4,3-a]quinoxaline 88: 4,5-dihydro-1-methyl-5-[3-[4-(6,11-dihydrodibenzo [b.e]oxepin-11-ylidene) piperidin-1-yl]propyl][1,2,4] triazolo[4,3-a]quinoxaline 89: 4,5-dihydro-1-methyl-5-[3-[4-(2-chlorothioxanthen-9-ylidene) piperidin-1-yl]propyl][1,2,4]triazolo[4,3-a] quinoxaline 90: 4,5-dihydro-1,4-dimethyl-5-[3-[4-[hydroxybis(4-fluorophenyl)methyl]piperidin-1-yl]propyl][1,2,4] triazolo[4,3-a]quinoxaline 91: 4,5-dihydro-1,4-dimethyl-5-[3-[4-[bis(4-fluorophenyl) methylene]piperidin-1-yl]propyl][1,2,4]triazolo[4,3-a] quinoxaline fumaric acid salt 92: 1-ethyl-4,5-dihydro-5-[3-[4-(diphenylmethylene) piperidin-1-yl]propyl][1,2,4]triazolo[4,3-a]quinoxaline 93: 4,5-dihydro-1,4-dimethyl-5-[3-[4-(diphenylmethylene) piperidin-1-yl]propyl][1,2,4]triazolo[4,3-a]quinoxaline 94: 4,5-dihydro-1,4,4-trimethyl-5-[3-[4-(diphenylmethylene) piperidin-1-yl]propyl][1,2,4]triazolo[4,3-a]quinoxaline The above-described compounds have the following physical properties:

Compound Spectrum Data

69: White Crystal
mp:176°–178° C. (Decomposed)
Elementary Analysis: as C30H33N6Cl Calcd.:C,70.23;H, 6.48;N,16.38;Cl,6.91 Found:C,70.37;H,6.43;N,16.39;Cl,6.93
IR(KBr) cm$^{-1}$:2814,1504,1143,1089,1011,756
$^1$HNMR(CDCl3) δ:7.44(1H,dd,J=7.8,1.5),7.38–7.35(3H,m),7.37(2H,AB,J=8.3),7.34–7.27(1H,m),7.24(2H,AB,J=8.3),7.19(2H,m), 6.93(1H,dd,J=7.8,1.0),6.89(1H,td,J=7.8,1.0),4.42(2H,s), 4.21(1H,s),3.37(2H,t,J=7.3),2.77(3H,s), 2.47(8H,brs), 2.41(2H,t,J=6.8),1.82(2H,quint,J=7.1)
MS: 512(M+)

70: Pale Brown Crystal
mp:140°–142° C.
Elementary Analysis: as C24H29N6Cl.2C4H4O4 Calcd.:C,57.44;H,5.57;N,12.56;Cl,5.30 Found:C; 57.69;H, 5.83;N,12.77;Cl,5.58
IR(KBr) cm$^{-1}$:2942,2814,1504,1431,1350,1156,1013, 748
$^1$HNMR(CDCl3) δ:7.46(1H,AB,J=7.8),7.29–7.20(5H,m), 6.95(1H,AB,J=8.3),6.90(1H,t,J=7.8),4.44(2H,s), 3.47(2H,s),3.39(2H,t,J=7.3),2.78(3H,s),2.47(8H,brs), 2.40(2H,t,J=7.3) 1.83(2H,m)
MS: 436(M+)

71: Colorless Amorphous
Elementary Analysis: as C28H36N8O.2C4H4O4 Calcd.:C,59.01;H,6.05;N,15.29 Found:C,58.78;H,6.26;N,15.53
IR(KBr) cm$^{-1}$:2934,2854,1522,1504,1466,1122,748
$^1$HNMR(CDCl3) δ:7.62(1H,m),7.47(1H,dd,J=8.3,1.5), 7.31(1H, m),7.25(1H,m),7.18(2H,m),7.01(1H,d,J=7.8),6.92 (1H,t, J=7.3),4.46(2H,s),4.20(2H,t,J=5.9),3.83(2H,t,J=5.9), 3.48 (2H,t,J=6.8),3.46(2H,q,J=6.8),3.41(4H,t,J=4.6),2.79 (3H, s),2.65(4H,brs),2.50(2H,t,J=6.8),1.89(2H,quint,J=6.8), 1.15(3H,t,J=6.8)
MS: 501(M+H)+

72: White Crystal
mp:92°–95° C.
Elementary Analysis: as C29H38N8O.2(C4H6O6) Calcd.:C,54.54;H,6.19;N,13.75 Found:C,54.90;H,6.20;N,13.48
IR(KBr) cm$^{-1}$:3406,2974,2880,1729,1611,1504,1125, 752

73: White Crystal
mp:139°–146° C. (Decomposed)
Elementary Analysis: as C32H35N8F.1.5(C4H6O6.H2O) Calcd.:C,58.08;H,5.90;N,14.26 Found:C,58.47;H,6.20;N,13.98
IR(KBr) cm$^{-1}$:3320,1562,1504,1309,1267,748,681,487

74: Pale Yellow Crystal
mp:139°–142° C.
Elementary Analysis: as C31H35N5O.C4H6O6.H2O Calcd.:C,63.53;H,6.55;N,10.58 Found:C,63.82;H,6.54;N,10.16
IR(KBr) cm$^{-1}$: 3324,1562,1502,1433,1307,1265,1069, 752,704,681

75: White Crystal
mp:141°–144° C. (Decomposed)
Elementary Analysis: as C31H33N5OF2.C4H6O6.H2O Calcd.:C,60.25;H,5.92;N,10.04 Found:C,60.49;H,5.86;N, 9.91

IR(KBr) cm$^{-1}$: 3322,1603,1506,1307,1265,1220,837, 752,681,571

76: White Crystal
mp:191°–192° C.
Elementary Analysis: as C31H35N5O.C4H6O6-H2O Calcd.:C,63.53;H,6.55;N,10.58 Found:C,63.76;H,6.17;N, 10.48
IR(KBr) cm$^{-1}$:3322,1678,1427,1307,1265,1067,681,485

77: White Crystal
mp:130°–132° C.
Elementary Analysis: as C31H31N5F2 Calcd.:C,72.78;H, 6.11;N,13.69 Found:C,72.50;H,6.19;N,13.65
IR(KBr) cm$^{-1}$:1508,1224,835,745,559
$^1$HNMR(CDCl3) δ:7.46(1H,dd,J=7.8,1.5),7.22(1H,td,J= 7.3, 1.5),7.07–7.04(4H,m),7.00–6.95(5H,m),6.91(1H,td,J= 7.3, 1.5),4.44(2H,s),3.41(2H,t,J=7.1),2.78(3H,s),2.50(4H,t, J=5.4),2.44(2H,t,J=7.1),2.39(4H,t,J=5.4),1.87(2H,quint, J=7.1)
MS: 511(M+)

78: Pale Yellow Crystal
mp:168°–174.5° C.
Elementary Analysis: as C33H33N5 Calcd.:C,79.32;H, 6.66;N,14.02 Found:C,78.92;H,6.74;N,13.86
IR(KBr) cm$^{-1}$:1504,1433,803,756
$^1$HNMR(CDCl3) δ:7.44(1H,dd,J=7.8,1.5),7.34–7.30(4H, m),7.25–7.18(5H,m),6.94(1H,dd,J=7.3,1.0),6.91(2H,s),6.88 (1H,dd, J=7.3,1.0),4.42(2H,s),3.37(2H,t,J=7.1),2.77(3H,s), 2.57 (2H,m),2.36(4H,m),2.16(4H,m),1.81(2H,quint,J=7.1)
MS: 500(M+H)+

79: White Crystal
mp:182°–184° C.
Elementary Analysis: as C31H35N5 Calcd.:C,77.95;H, 7.39;N,14.66 Found:C,78.16;H,7.54;N,14.38
IR(KBr) cm$^{-1}$:3446,1657,1562,1510,1460,582
$^1$HNMR(CDCl3) δ:7.44(1H,dd,J=7.8,1.5),7.29–7.13 (11H,m), 6.95–6.88(2H,m),4.41(2H,s),3.51(1H,d,J=11.2), 3.37(2H,t, J=6.8),2.90(2H,d,J=10.7),2.77(3H,s),2.41(2H,t, J=6.8), 2.16–1.85(5H,m),1.58(2H,d,J=13.2),1.30–1.24(2H, m)
MS: 478(M+H)+

80: Pale Yellow Crystal
mp:138°–141° C.
Elementary Analysis: as C25H28N6O Calcd.:C,70.07;H, 6.59;N,19.61 Found:C,69.86;H,6.72;N,19.53
IR(KBr) cm$^{-1}$:2948,1611,1555,1508,1433,1352,1236, 743
$^1$HNMR(CDCl3) δ:7.76(1H,d,J=7.8),7.59–7.52(2H,m), 7.47(1H, dd,J=7.8,1.2),7.30 (1H,td,J=7.1,1.5),7.24(1H,m), 7.01(1H, dd,J=8.3,1.0),6.92(1H,td,J=7.8,1.2),4.46(2H,s), 3.44(2H,t, J=7.1),3.17–3.03(3H,m),2.79(3H,s),2.48(2H,t,J= 6.8),2–25–2.10(6H,m),1.90(2H,m)
MS: 428(M+)

81: White Crystal
mp:190°–195° C.
Elementary Analysis: as C25H29N7O Calcd.:C,67.70;H, 6.59;N,22.11 Found:C,67.44;H,6.48;N,21.89
IR(KBr) cm$^{-1}$:1694,1506,1487,1429,1379,1350,1282, 752
$^1$HNMR(CDCl3) δ:7.65(1H,dd,J=8.1,1.2),7.36–7.30(2H, m), 7.13(1H,d,J=8.3),7.08–7.03(3H,m),6.99(1H,td,J=7.8, 1.0), 4.46(2H,s),4.31(1H,m),3.48(2H,t,J=7.1),3.14(2H,d,J= 11.7),2.77(3H,s),2.59–2.48(4H,m),2.21(2H,t-like),1.94(2H, m), 1.80–1.76(2H,m)
MS: 443(M+)

82: White Crystal
mp:103°–108° C.
Elementary Analysis: as C25H29N7.C4H4O4 Calcd.:C, 64.07;H,6.12;N,18.04 Found:C,64.28;H,6.37;N,18.38

IR(KBr) cm⁻¹:1560,1504,1475,1429,754,741

¹HNMR(CDCl3) δ:8.99(1H,brs),8.29(1H,dd,J=4.9,1.5), 7.97(1H, dd,J=7.8,1.5),7.47(1H,dd,J=7.8,1.2),7.23(1H,td,J=7.6, 1.5),7.10(1H,brs),7.06(1H,dd,J=8.3,4.4),6.99(1H,d,J=8.3), 6.91(1H,td,J=7.3,1.2),4.47(2H,s),3.43(2H,t,J=6.8), 3.04 (2H,d-like),2.81(1H,m),2.79(3H,s),2.46(2H,t,J=6.7), 2.14(2H,t-like),2.10-2.00(2H,m),1.95-1.70(4H,m)

MS: 427(M+)

83:White Amorphous

Elementary Analysis:as C25H29N7 Calcd.:C,70.23;H, 6.84;N,22.93 Found:C,70.11;H,6.98;N,23.16

IR(KBr) cm⁻¹:2940,1678,1613,1562,1504,1473,1433, 750

¹HNMR(CDCl3) δ:8.86(1H,s),8.17(1H,d,J=6.6),7.48 (1H,d, J=7.7),7.35-7.25(2H,m),7.06(1H,s),7.00(1H,m),6.94 (1H,t, J=7.7),4.46(2H,s),3.42(2H,t,J=7.3),3.2-3.0(2H,d-like), 2.90(1H,m),2.78(3H,s),2.49(2H,t,J=7.3),2.22-1.77 (8H,m)

MS: 427(M+)

84:White Amorphous

Elementary Analysis:as C25H29N7 Calcd.:C,70.23;H, 6.84;N,22.93 Found:C,70.45;H,7.04;N,22.79

IR(KBr) cm⁻¹:2938,1673,1504,1433,781,750

¹HNMR(CDCl3) δ:8.38(1H,dd,J=4.7,1.7),7.67(1H,dd,J=8.1, 1.3),7.47(1H,dd,J=8.1,1.7),7.27-7.23(2H,m),7.10(1H, m), 6.98(1H,d,J=8.1),6.93(1H,t,J=8.1),4.46(2H,s),3.41(2H, t, J=7.3),3.12(1H,m),3.1-3.0(2H,d-like),2.78(3H,s),2.48 (2H, t,J=6.8),2.25-2.10(6H,m),1.92(1H,m),1.8-1.7(1H,m)

MS: 427(M+)

85:Pale Yellow Amorphous

Elementary Analysis:as C30H31N5 Calcd.:C,78.06;H, 6.77;N,15.17 Found:C,77.91;H,6.81;N,15.31

IR(KBr) cm⁻¹:2942,2802,1611,1557,1504,1475,1431, 1350,754

¹HNMR(CDCl3) δ:7.58-7.03(12H,m),6.98-6.75(2H,m), 4.42(2H, s),3.57-3.20(4H,m),2.77(3H,s),2.75-2.40(6H,m), 2.02-1.80 (2H,m)

MS: 462(M+H)+

86:Pale Brown Crystal mp:111°-112° C.

Elementary Analysis:as C24H30N6O Calcd.:C,68.87;H, 7.23;N,20.08 Found:C,68.72;H,7.20;N,19.84

IR(KBr) cm⁻¹:2946,2818,1504,1243,746

¹HNMR(CDCl3) δ:7.46(1H,d,J=7.8),7.23(1H,t,J=7.8), 7.03-6.86(6H,m),4.46(2H,s),3.86(3H,s),3.43(2H,t,J=7.3), 3.12 (4H,s),2.78(3H,s),2.67(4H,s),2.49(2H,t,J=7.3),1.89 (2H, quint,J=7.3)

MS: 418(M+)

87:Yellow Crystal mp:160°-161.5° C.

Elementary Analysis:as C33H35N5 Calcd.:C,79.01;H, 7.03;N,13.96 Found:C,78.93;H,7.15;N,13.80

IR(KBr) cm⁻¹:2900,1504,1431,1350,745

¹HNMR(CDCl3) δ:7.45(1H,dd,J=7.8,1.2),7.21(1H,t,J=7.3), 7.12-7.06(8H,m),6.97(1H,d,J=8.3),6.90(1H,t,J=7.3), 4.44 (2H,s),3.45-3.36(2H,m),3.40(2H,t,J=7.3),2.82(2H,m), 2.77 (3H,s),2.67(2H,m),2.41(6H,m),2.19(2H,m),1.85(2H, quint, J=7.3)

MS: 501(M+)

88:White Crystal mp:148°-150° C.

Elementary Analysis : C32H33N5O.1/2H2O Calcd.:C, 74.97;H,6.69;N,13.66 Found:C,74.84;H,6.68;N,13.31

IR(KBr) cm⁻¹:2952,1504,1481,752

¹HNMR(CDCl3) δ:7.46(1H,dd,J=7.8,1.5),7.36(1H,ABd, J=6.8, 1.5),7.31(1H,td,J=7.3,1.5),7.28-7.20(2H,m),7.15 (1H,ABd, J=7.3,1.5),7.09(1H,td-like,J=7.8,1.5),7.01(1H,dd, J=7.3, 1.5),6.97(1H,d,J=7.3),6.90(1H,td,J=7.3,1.5),6.81(1H, td, J=7.3,1.0),6.76(1H,dd,J=8.3,1.0),5.72(1H,AB,J=12.2), 4.78 (1H,AB,J=12.2),4.45(2H,s),3.41(2H,t,J=6.8),2.77(3H, s), 2.75-2.57(4H,m),2.40(4H,m),2.26(1H,m),2.10(1H,m), 1.85 (2H,quint,J=6.8)

MS: 503(M+)

89:Yellow Amorphous

Elementary Analysis:as C31H30N5SCl Calcd.:C, 68.94;H,5.60;N,12.97; S,5.94;Cl,6.56 Found:C,69.13;H, 5.77;N,13.11; S,6.25;Cl,6.83

IR(KBr) cm⁻¹:2932,1560,1504,1433,1096,754

¹HNMR(CDCl3) δ:7.48-7.45(2H,m),7.40(1H,AB,J=8.3), 7.31-7.19(5H,m),7.16(1H,dd,J=8.3,2.0),6.97(1H,d,J=8.3), 6.91 (1H,t,J=7.3),4.44(2H,s),3.41(2H,t,J=7.3),2.78(3H+2H, s+m), 2.71(4H,m),2.41(2H,t,J=6.8),2.13(2H,m),1.87(2H, quint, J=6.8)

MS: 539(M+)

90:Colorless Amorphous

Elementary Analysis:as C32H35N5OF2 Calcd.:C, 70.70;H,6.49;N,12.88; F,6.99 Found:C,70.93;H,6.28;N, 13.03; F,7.18

IR(KBr) cm⁻¹:3328,1504,1224,1160,833,748,571

¹HNMR(CDCl3) δ:7.42(5H,m),7.21(1H,td,J=7.3,1-9), 6.97(4H, m),6.90(2H,m),4.90(1H,q,J=6.6),3.56(1H,quint,J= 6.2),3.15(1H,quint,J=7.3),2.92(2H,t,J=12.8),2.75(3H,s), 2.42(1H,m), 2.34(4H,m),1.96(4H,m),1.82(2H,m),1.24(3H, d,J=6.6)

MS: 544(M+H)+

91:Colorless Amorphous

Elementary Analysis:as C32H33N5F2.C4H4O4 Calcd.:C,67.88;H,5.81;N,10.91; F,5.92 Found:C,67.56;H, 5.68;N,11.14; F,5.84

IR(KBr) cm⁻¹:2958,1506,1222,835,748,559

¹HNMR(CDCl3) δ:7.47(1H,dd,J=7.8,1.5),7.23(1H,td,J= 7.5, 1.5),7.07-7.02(4H,m),6.99-6.89(6H,m),4.89(1H,q,J= 6.8), 3.57(1H,quint,J=6.8),3.21(1H,quint,J=6.8),2.78(3H,s), 2.38(10H,s),1.83(2H,quint,J=6.8),1.27(3H,d,J=6.8)

MS: 526(M+H)+

92:White Amorphous

Elementary Analysis:as C32H35N5 Calcd.:C,78.49;H, 7.20;N,14.30 Found:C,78.19;H,7.03;N,14.58

IR(Neat) cm⁻¹:2946,2810,1557,1502,1473,1009,702

¹HNMR(CDCl3) δ:7.43(1H,d,J=7.8),7.29-7.12(11H,m), 6.97(1H, d,J=7.8),6.89(1H,t,J=7.8),4.43(2H,s),3.40(2H,t,J= 7.8), 3.10(2H,q,J=6.8),2.50-2.17(10H,m),1.86(2H,quint,J= 6.8), 1.49(3H,t,J=6.8)

MS: 490(M+H)+

93: Colorless Amorphous

Elementary Analysis: as C32H35N5 Calcd.: C,78.49;H, 7.20;N,14.30 Found: C,78.69;H,7.37;N,14.01

IR(KBr) cm⁻¹: 2930,1553,1502,1468,1429,1350,750,704

¹HNMR(CDCl3) δ: 7.46(1H,d,J=7.8),7.29-7.25(4H,m), 7.22-7.16(4H,m),7.12-7.10(3H,m),6.93(1H,d,J=7.8),6.90 (1H,t,J=7.3), 4.88(1H,q,J=6.9),3.57(1H,quint,J=6.8),3.21 (1H,quint, J=6.8),2.78(3H,s),2.47-2.40(10H,m),1.84(2H, quint,J=6.8), 1.27(3H,d,J=6.9)

MS: 490(M+H)+

94: Colorless Amorphous

Elementary Analysis: as C33H37N5 Calcd.: C,78.49;H, 7.40;N,13.90 Found: C,78.58;H,7.13;N,14.27

IR(KBr) cm⁻¹: 2934,1537,1502,1466,1427,748,702

¹HNMR(CDCl3) δ: 7.45(1H,d,J=8.3),7.30-7.24(4H,m), 7.24-7.14(4H,m),7.14-7.11(3H,m),6.97(1H,d,J=8.3),6.90 (1H,t, J=7.8),3.41(2H,t,J=7.3),2.77(3H,s),2.54-2.37(10H, m),1.77(2H,quint,J=7.3),1.62(6H,s)

MS: 504(M+H)+

Example 95

1-(3-chloropropyl)-4-benzoylpiperidine (95)

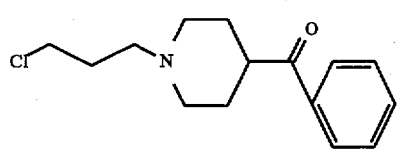

To a mixed solvent consisting of 200 ml of toluene and 64 ml of 25% aqueous sodium hydroxide solution, 50.0 g of 4-benzoylpiperidine hydrochloric acid salt, 69.5 g of 1-bromo-3-chloropropane and 1.36 g of tetrabutylammonium hydrogen sulfate are added and the resulting mixture is stirred at room temperature for 30 hours. To the reaction mixture, 200 ml of water is added and the resultant is subjected to extraction with ethyl acetate. The organic layer is condensed and then purified by column chromatography to obtain 39.6 g of the captioned compound in the form of colorless crystals.

mp: 72°–73° C. (Decomposed)

IR(KBr)cm$^{-1}$: 2942,2816,1649,1562,1456,1292,984,700

$^1$HNMR(CDCl3) δ: 8.00–7.82(2H,m),7.65–7.22(3H,m), 3.61(2H,t, J=6.4),3.42–2.81(3H,m),2.58(2H,t,J=7.0), 2.32–1.61(8H,m)

MS: 265(M+)

Example 96

1-(3-chloropropyl)-4-[hydroxy(4-dimethylaminophenyl) phenylmethyl]piperidine (96)

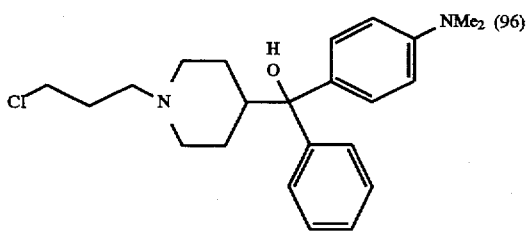

In 30 ml of anhydrous tetrahydrofuran, 5.0 g of the compound of Example 95 is dissolved. After cooling the solution to 0° C., 30 ml of 1M p-dimethylaminophenyl magnesium bromide solution in tetrahydrofuran is added dropwise. The resulting mixture is stirred at room temperature for 1 hour and saturated aqueous ammonium chloride solution is added, followed by extraction with ethyl acetate. The organic layer is condensed and purified by column chromatography to obtain 5.5 g of the captioned compound in the form of pale yellow amorphous.

IR(neat)cm$^{-1}$: 3302,2940,1611,1524,1439,948,818,727, 700

$^1$HNMR(CDCl3) δ: 7.51–7.12(7H,m),6.78–6.57(2H,m), 3.56(2H,t, J=6.7),3.08–2.81(8H,m),2.57–2.32(2H,m), 2.16–1.31(9H,m)

MS: 386(M+)

Example 97

1-(3-chloropropyl)-4-ethoxycarbonylpiperidine (97)

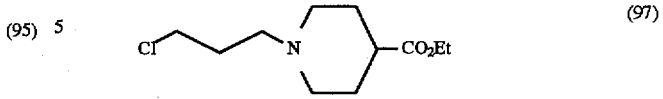

In 250 ml of 2-butanone, 26.1 g of ethyl isonipecotate, 52.5 g of 1-bromo-3-chloropropane and 34.4 g of potassium carbonate are added and the resulting mixture is heated to reflux for 5 hours. After filtering off inorganic materials, the filtrate is condensed and distilled under reduced pressure (120° C./0.2 mmHg) to obtain 18.0 g of the captioned compound in the form of colorless oil.

IR(neat)cm$^{-1}$: 2954,2812,1734,1450,1379,1296,1261, 1181,1050

$^1$HNMR(CDCl3) δ: 4.13(2H,q,J=7.3),3.58(2H,t,J=6.6), 3.00–2.72(2H,m),2.58–1.61(11H,m),1.25(3H,t,J=7.0)

Example 98

1-(3-chloropropyl)-4-[hydroxybis(4-dimethylaminophenyl) methyl]piperidine (98)

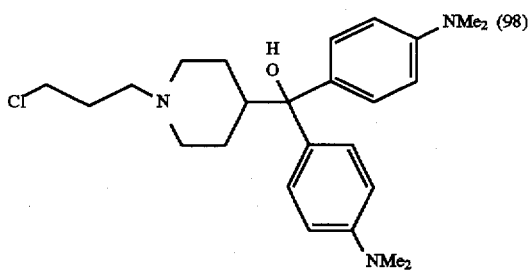

In 20 ml of anhydrous tetrahydrofuran, 2.5 g of the compound of Example 97 is dissolved. After cooling the solution to 0° C., 30 ml of 1M p-dimethylaminophenyl magnesium bromide solution in tetrahydrofuran is added dropwise. The resulting mixture is stirred at room temperature for 1 hour and saturated aqueous ammonium chloride solution is added, followed by extraction with ethyl acetate. The organic layer is condensed and purified by column chromatography to obtain 3.5 g of the captioned compound in the form of colorless amorphous.

IR(KBr)cm$^{-1}$: 3336,2794,1611,1516,1444,1325,1131, 1064,944, 814

$^1$HNMR(CDCl3) δ: 7.38–7.16(4H,m),6.78–6.56(4H,m), 3.57(2H,t, J=6.7),3.05–2.80(14H,m),2.52–2.28(2H,m), 2.16–1.31(9H,m)

MS: 429(M+)

Examples 99–105

The same procedure as in Example 96 is repeated except that m-tolyl magnesium bromide is used in place of p-dimethylaminophenyl magnesium bromide to obtain compound 99; that m-methoxyphenyl magnesium bromide is used in place of p-dimethylaminophenyl magnesium bromide to obtain compound 100; that 3,4-dimethoxyphenyl magnesium bromide is used in place of p-dimethylaminophenyl magnesium bromide to obtain compound 101.

The same procedure as in Example 98 is repeated except that o-tolyl magnesium bromide is used in place of p-dimethylaminophenyl magnesium bromide to obtain compound 102; that o-methoxyphenyl magnesium bromide is used in place of p-dimethylaminophenyl magnesium bromide to obtain compound 103; that 3,4-dimethoxyphenyl magnesium bromide is used in place of p-dimethylaminophenyl magnesium bromide to obtain compound 104; or that 2-furyl lithium is used in place of p-dimethylaminophenyl magnesium bromide to obtain compound 105.

| Compound | Ar1 | Ar2 |
|---|---|---|
| 99 | 3-Tolyl | Ph |
| 100 | 3-MeO—Ph | Ph |
| 101 | 3,4-(MeO)2Ph | Ph |
| 102 | 2-Tolyl | 2-Tolyl |
| 103 | 2-MeO—Ph | 2-MeO—Ph |
| 104 | 3,4-(MeO)2Ph | 3,4-(MeO)2Ph |
| 105 | 2-Furyl | 2-Furyl |

99: 1-(3-chloropropyl)-4-[hydroxyphenyl(3-tolyl)methyl]piperidine

100: 1-(3-chloropropyl)-4-[hydroxy(3-methoxyphenyl)phenylmethyl]piperidine

101: 1-(3-chloropropyl)-4-[hydroxy(3,4-dimethoxyphenyl)phenylmethyl]piperidine

102: 1-(3-chloropropyl)-4-[hydroxybis(2-tolyl)methyl]piperidine

103: 1-(3-chloropropyl)-4-[hydroxybis(2-methoxyphenyl)methyl]piperidine

104: 1-(3-chloropropyl)-4-[hydroxybis(3,4-dimethoxyphenyl)methyl]piperidine

105: 1-(3-chloropropyl)-4-[hydroxybis(2-furyl)methyl]piperidine

The above-described compounds have the following physical properties:

99: Colorless Amorphous
IR(KBr)cm$^{-1}$: 3400,2950,2812,1738,1603,1491,1448, 1257, 1143,739,708
$^1$HNMR(CDCl3) δ: 7.56–6.90(9H,m),3.57(2H,t,J=6.8), 3.07–2.81(2H,m),2.56–2.32(5H,m),2.13–1.38(9H,m)
MS: 357(M+)

100: Colorless Oil
IR(Neat)cm$^{-1}$: 3500,2950,2814,1736,1601,1489,1448, 1251, 1050,739,706
$^1$HNMR(CDCl3) δ: 7.56–6.92(8H,m),6.76–6.67(1H,m), 3.77(3H, s),3.57(2H,t,J=6.7),3.06–2.83(2H,m),2.59–2.31 (2H,m),2.18–1.42(9H,m)
MS: 373(M+)

101: Pale Green Amorphous
IR(KBr)cm$^{-1}$: 3370,2950,1516,1448,1259,1137,1027, 737,700
$^1$HNMR(CDCl3) δ: 7.58–6.72(8H,m),3.83(6H,s),3.56 (2H,t, J=6.8),3.05–2.80(2H,m),2.58–2.30(2H,m),2.21–1.41 (9H,m)
MS: 403(M+)

102: White Amorphous
IR(KBr)cm$^{-1}$: 3380,2952,2774,1487,1460,1379,745,656, 634
$^1$HNMR(CDCl3) δ: 8.30–7.52(2H,br.),7.15–7.11(4H,m), 7.04–6.95 (2H,m),3.59(2H,t,J=6.35),3.10(2H,d,J=7.32), 2.04(6H, s),2.70–2.40(3H,br.),2.30–1.40(9H,m)

MS: 371(M+)

103: White Crystal
mp: 141.5°–142.5° C.
IR(KBr)cm$^{-1}$: 3492,2936,2810,1487,1468,1437,1381, 1286, 1243,1058,1023,750
$^1$HNMR(CDCl3) δ: 7.61(2H,d,J=7.6),7.16(2H,dt,J=7.6, 0.9), 6.97(2H,dt,J=7.6,1.2),6.75(2H,dd,J=7.6,0.9),5.22(1H, br.), 3.58(2H,t,J=6.6),3.49(6H,s),2.97(2H,d,J=11.0),2.82 (1H,m), 2.51(2H,t,J=7.0),2.20–2.02(2H,m),1.99(2H,quint., J=6.7), 1.75(2H,q,J=11.3),1.60–1.30(2H,br.)
MS: 403(M+)

104: Colorless Amorphous
IR(KBr)cm$^{-1}$: 3410,2942,1512,1462,1412,1259,1139, 1025,762
$^1$HNMR(CDCl3) δ: 7.20–6.72(6H,m),3.84(12H,s),3.58 (2H,t, J=6.8),3.14–2.88(2H,m),2.62–2.31(2H,m),2.16–1.41 (9H,m)
MS: 463(M+)

105: Pale Yellow Crystal
mp: 74°–74.5° C.
IR(KBr)cm$^{-1}$: 3076,2952,2786,1154,1042,1013,1002, 984,959, 806,735,600
$^1$HNMR(CDCl3) δ: 7.40(2H,s),6.35–6.30(4H,m),3.57 (2H,m),3.02(2H,br.),2.82(1H,br.),2.53(2H,br.),2.31(1H,br.), 2.04(4H, br.),1.55(4H,br.)
MS: 323(M+)

Example 106

1-(3-chloropropyl)-4-[phenyl(4-tolyl)methylene]piperidine (106)

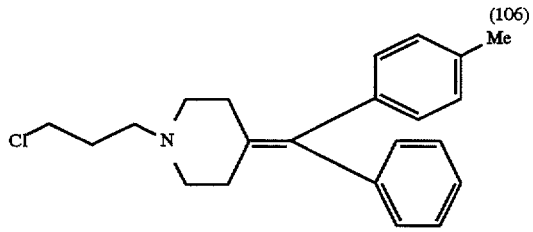

Sixty milliliters of 2-butanone is added to 5.3 g of 4-[phenyl(4-tolyl)methylene]piperidine, 3 ml of 1-bromo-3-chloropropane and 5.3 g of potassium carbonate, and the resulting mixture is heated to reflux for 5 hours. The resultant is subjected to the same post treatment as in Example 32, and the resultant is purified by silica gel column chromatography (hexane:ethyl acetate=1:3) to obtain 5.3 g of the captioned compound in the form of colorless oil.

IR(Neat)cm$^{-1}$: 2924,2808,1512,1441,1375,1299,1129, 816,758, 700

$^1$HNMR(CDCl3) δ: 7.19–6.85(9H,m),3.61(2H,t,J=6.4) .2.60–2.31(13H,m),1.98(2H,quint,J=6.8)

MS: 339(M+)

Example 107

1-(3-chloropropyl)-4-[bis(4-tolyl)methylene]piperidine (107)

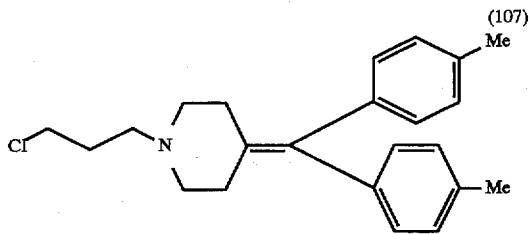

(107)

To 4-[bis(4-tolyl)methylene]piperidine and 6.37 g of 1-bromo-3-chloropropane, 20 ml of toluene, 10 ml of 25% sodium hydroxide solution and 0.27 g of tetrabutylammonium hydrogen sulfate are added and the resulting mixture is stirred for 10 hours at room temperature. The resultant is subjected to extraction with ethyl acetate and the organic layer is washed with water and dried. The solvent is evaporated and the residue is purified by silica gel column chromatography (dichloromethane-dichloromethane:ethyl acetate=1:1) to obtain 3.53 g of the captioned compound in the form of colorless oil.

IR(KBr)cm$^{-1}$: 2940,2906,1602,1511,1440,1002,818,774

$^1$HNMR(CDCl3) δ: 7.21–7.02(4H,m),7.00–6.83(4H,m), 3.60(2H,t, J=6.8),2.61–2.29(10H,m),2.30(6H,s),1.98(2H, quint,J=6.8)

MS: 353(M+)

Example 108

1-(3-chloropropyl)-4-[phenyl(3-tolyl)methylene]piperidine (108)

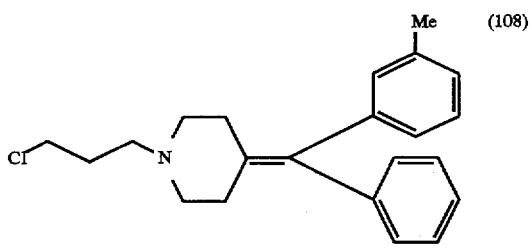

(108)

In 10 ml of ethanol, 2.35 g of the compound of Example 99 is dissolved and 10 ml of concentrated hydrochloric acid is added to the solution. The resulting mixture is stirred at 100° C. for 1 hour and the mixture is cooled. The resulting mixture is neutralized by adding thereto water and sodium hydroxide and the resulting mixture is subjected to extraction with ethyl acetate. The organic layer is condensed and purified by column chromatography to obtain 1.89 g of the captioned compound in the form of colorless oil.

IR(KBr)cm$^{-1}$: 2931,2802,1501,1438,1371,1301,1127, 756,704

$^1$HNMR(CDCl3) δ: 7.56–6.90(9H,m),3.58(2H,t,J=6.4), 2.61–2.22(13H,m),1.96(2H,quint,J=6.8)

MS: 339(M+)

Examples 109–125

The same procedure as in Example 106 is repeated except that 4-[(4-methoxyphenyl)phenylmethylene]piperidine is used in place of 4-[phenyl(4-tolyl)methylene]piperidine to obtain compound 114; that 4-[(4-chlorophenyl)phenylmethylene]piperidine is used in place of 4-[phenyl(4-tolylmethylene]piperidine to obtain compound 115; that 4-[phenyl(4-trifluoromethyl)phenylmethylene]piperidine is used in place of 4-[phenyl(4-tolyl)methylene]piperidine to obtain compound 116; that 4-[bis[(4-trifluoromethyl)phenyl]methylene]piperidine is used in place of 4-[phenyl (4-tolyl)methylene]piperidine to obtain compound 117; or that 4-[(4-fluorophenyl)phenylmethylene]piperidine is used in place of 4-[phenyl(4-tolyl)methylene]piperidine to obtain compound 118.

The same procedure as in Example 107 is repeated except that 4-[(3-chlorophenyl)phenylmethylene]piperidine is used in place of 4-[bis(4-tolyl)methylene]piperidine to obtain compound 119; that 4-[bis(3-chlorophenyl)methylene] piperidine is used in place of 4-[bis(4-tolyl)methylene] piperidine to obtain compound 120; that 4-[phenyl(2-pyridyl)methylene]piperidine is used in place of 4-[bis(4-tolyl)methylene]piperidine to obtain compound 124; or that 4-[naphthylphenylmethylene]piperidine is used in place of 4-[bis(4-tolyl)methylene]piperidine to obtain compound 125.

The same procedure as in Example 108 is repeated except that 100 is used in place of 99 to obtain compound 109; that 101 is used in place of 99 to obtain compound 110; that 102 is used in place of 99 to obtain compound 111; that 103 is used in place of 99 to obtain compound 112; that 104 is used in place of 99 to obtain compound 113; that 96 is used in place of 99 to obtain compound 121; that 98 is used in place of 99 to obtain compound 122; or that 105 is used in place of 99 to obtain compound 123.

| Compound | Ar1 | Ar2 |
|---|---|---|
| 109 | 3-MeO—Ph | Ph |
| 110 | 3,4-(MeO)2-Ph | Ph |
| 111 | 2-Tolyl | 2-Tolyl |
| 112 | 2-MeO—Ph | 2-MeO—Ph |
| 113 | 3,4-(MeO)2-Ph | 3,4-(MeO)2-Ph |
| 114 | 4-MeO—Ph | Ph |
| 115 | 4-Cl—Ph | Ph |
| 116 | 4-CF3-Ph | Ph |
| 117 | 4-CF3-Ph | 4-CF3-Ph |
| 118 | 4-F—Ph | Ph |
| 119 | 3-Cl—Ph | Ph |
| 120 | 3-Cl—Ph | 3-Cl—Ph |
| 121 | 4-NMe2-Ph | Ph |
| 122 | 4-NMe2-Ph | 4-NMe2-Ph |
| 123 | 2-Furyl | 2-Furyl |
| 124 | 2-Pyridyl | Ph |
| 125 | 2-Naphthyl | Ph |

109: 1-(3-chloropropyl)-4-[(3-methoxyphenyl) phenylmethylene]piperidine

110: 1-(3-chloropropyl)-4-[(3,4-dimethoxyphenyl) phenylmethylene]piperidine

111: 1-(3-chloropropyl)-4-[bis(2-tolyl)methylene]piperidine

112: 1-(3-chloropropyl)-4-[bis(2-methoxyphenyl) methylene]piperidine

113: 1-(3-chloropropyl)-4-[bis(3,4-dimethoxyphenyl) methylene]piperidine

114: 1-(3-chloropropyl)-4-[(4-methoxyphenyl) phenylmethylene]piperidine

115: 1-(3-chloropropyl)-4-[(4-chlorophenyl) phenylmethylene]piperidine

116: 1-(3-chloropropyl)-4-[[4-(trifluoromethyl)phenyl] phenylmethylene]piperidine 117: 1-(3-chloropropyl)-4-[bis[(4-(trifluoromethyl)phenyl] methylene]piperidine 118: 1-(3-chloropropyl)-4-[(4-fluorophenyl) phenylmethylene]piperidine 119: 1-(3-chloropropyl)-4-[(3-chlorophenyl) phenylmethylene]piperidine
120: 1-(3-chloropropyl)-4-[bis(3-chlorophenyl)methylene]piperidine
121: 1-(3-chloropropyl)-4-[(4-dimethylaminophenyl)phenylmethylene]piperidine
122: 1-(3-chloropropyl)-4-[bis(4-dimethylaminophenyl)methylene]piperidine
123: 1-(3-chloropropyl)-4-[bis(2-furyl)methylene]piperidine
124: 1-(3-chloropropyl)-4-[phenyl(2-pyridyl)methylene]piperidine
125: 1-(3-chloropropyl)-4-[(2-naphthyl)phenylmethylene]piperidine The above-described compounds have the following physical properties:

Compound Spectrum Data

109: Colorless Oil
IR(Neat)cm$^{-1}$: 2958,2808,1597,1576,1431,1299,1251, 1145, 1051,756,704
$^1$HNMR(CDCl3) δ: 7.38–7.06(6H,m),6.83–6.62(3H,m), 3.76(3H, s),3.60(2H,t,J=6.4),2.60–2.25(10H,m),1.94(2H, quint,J=6.8)
MS: 355(M+)

110: Pale Yellow Oil
IR(Neat)cm$^{-1}$: 2962,2812,1591,1565,1433,1275,1127, 762,700
$^1$HNMR(CDCl3) δ: 7.58–6.72(8H,m),3.80(6H,s),3.59 (2H,t, J=6.3),2.62–2.28(10H,m),1.93(2H,quint,J=6.7)
MS: 385(M+)

111: Pale Yellow Oil
IR(neat)cm$^{-1}$: 2956,2808,1458,1377,1299,1243,1131, 754,729
$^1$HNMR(CDCl3) δ: 7.17–6.94(8H,m),3.60(2H,t,J=6.4), 2.76–2.10 (10H,m),2.34(3H,s),2.19(3H,s),1.97(2H,t,J=6.4)
MS: 353(M+)

112: White Crystal
mp: 47°–48° C.
IR(KBr)cm$^{-1}$: 2940,2834,1491,1462,1435,1294,1267, 1245, 1116,1054,1029,754,418
$^1$HNMR(CDCl3) δ: 7.23–6.98(4H,m),3.88–6.69(4H,m), 3.88–3.63(6H,br.),3.60(2H,t,J=6.7),2.75–2.05(10H,m),1.97 (2H,t, J=6.7)
MS: 385(M+)

113: Pale Yellow Oil
IR(Neat)cm$^{-1}$: 2954,2825,1597,1572,1421,1263,1132, 752,700
$^1$HNMR(CDCl3) δ: 7.21–6.70(6H,m),3.84(12H,s),3.60 (2H,t, J=6.4),2.61–2.27(10H,m),1.95(2H,quint,J=6.7)
MS: 445(M+)

114: Pale Yellow Amorphous
IR(KBr)cm$^{-1}$: 2956,2808,1607,1510,1301,1245,1176, 1038, 830,756,700
$^1$HNMR(CDCl3) δ: 7.18–6.72(9H,m),3.78(3H,s),3.60 (2H,t, J=6.4),2.62–2.26(10H,m),1.95(2H,quint,J=6.8)
MS: 355(M+)

115: Colorless Amorphous
IR(KBr)cm$^{-1}$: 2926,2774,1510,1444,1375,1299,1131, 787,760, 700
$^1$HNMR(CDCl3) δ: 7.41–6.95(9H,m),3.60(2H,t,J=6.4), 2.62–2.30(10H,m),1.98(2H,quint,J=6.8)
MS: 359(M+)

116: Yellow Oil
IR(Neat)cm$^{-1}$: 2960,2810,1615,1326,1166,1125,1067, 835,758
$^1$HNMR(CDCl3) δ: 7.62–7.50(2H,m),7.38–7.02(7H,m), 3.60(2H,t, J=6.4),2.62–2.31(10H,m),1.97(2H,quint,J=6.8)
MS: 393(M+)

117: Colorless Amorphous
IR(KBr)cm$^{-1}$: 2962,2810,1615,1325,1166,1127,1067, 1019, 835,760
$^1$HNMR(CDCl3) δ: 7.63–7.49(4H,m),7.41–7.02(4H,m), 3.60(2H,t, J=6.4),2.63–2.30(10H,m),1.94(2H,quint,J=6.8)
MS: 461(M+)

118: Colorless Oil
IR(Neat)cm$^{-1}$: 2960,2808,1603,1508,1224,832,758,700
$^1$HNMR(CDCl3) δ: 7.31–6.76(9H,m),3.50(2H,t,J=6.4), 2.58–2.17(10H,m),1.96(2H,quint,J=6.8)
MS: 343(M+)

119: Pale Yellow Oil
IR(Neat)cm$^{-1}$: 2960,2808,1593,1564,1444,1299,1131, 1079, 785,739,702
$^1$HNMR(CDCl3) δ: 7.45–6.92(9H,m),3.61(2H,t,J=6.4), 2.63–2.25(10H,m),2.00(2H,quint,J=6.8)
MS: 359(M+)

120: Pale Yellow Oil
IR(Neat)cm$^{-1}$: 2960,2810,1593,1564,1470,1299,1079, 789,758, 714
$^1$HNMR(CDCl3) δ: 7.52–6.92(8H,m),3.60(2H,t,J=6.4), 2.61–2.18(10H,m),1.98(2H,quint,J=6.8)
MS: 393(M+)

121: Pale Yellow Oil
IR(Neat)cm$^{-1}$: 2950,2894,2804,1609,1520,1444,1352, 1195, 1021,818,768,702
$^1$HNMR(CDCl3) δ: 7.36–6.92(7H,m),6.72–6.57(2H,m), 3.61(2H,t, J=6.4),3.13(6H,s),2.62–2.31(10H,m),1.93(2H, quint,J=6.8)
MS: 368(M+)

122: White Crystal
IR(KBr)cm$^{-1}$: 2890,2770,1611,1522,1350,1220,1191, 1131, 948,816,754
$^1$HNMR(CDCl3) δ: 7.00–6.96(4H,m),6.64–6.60(4H,m), 3.60(2H,t, J=6.7),2.92(12H,s),2.60–2.35(10H,m),1.96(2H, quint,J=6.8)
MS: 411(M+)

123: Pale Yellow Oil
IR(neat)cm$^{-1}$: 2954,2810,1375,1154,1015,808,737
$^1$HNMR(CDCl3) δ: 7.40(2H,dd,J=2.0,1.0),6.40(2H,dd,J= 3.4, 2.0),6.15(2H,dd,J=3.4,1.0),3.63(2H,t,J=6.4),2.71–2.67 (10H,m),2.07(2H,br)
MS: 305(M+)

124: Pale Yellow Oil
IR(Neat)cm$^{-1}$: 2954,2808,1584,1468,1429,1301,1129, 994,748, 702
$^1$HNMR(CDCl3) δ: 8.65–8.56(1H,m),7.72–7.49(1H,m), 7.21–7.00(7H,m),3.60(2H,t,J=6.4),2.61–2.30(10H,m),1.91 (2H,quint, J=6.8)
MS: 326(M+)

125: Yellow Oil
IR(Neat)cm$^{-1}$: 3056,2960,2808,1599,1504,1468,1441, 1375, 1125,820,752,702
$^1$HNMR(CDCl3) δ: 7.88–7.12(12H,m),3.60(2H,t,J=6.6), 2.62–2.14(10H,m),1.99(2H,quint,J=6.8)
MS: 375(M+)

Example 126

4,5-dihydro-1-methyl-5-[3-(4-ethoxycarbonylpiperidin-1-yl)propyl][1,2,4]triazolo[4,3-a]quinoxaline (126)

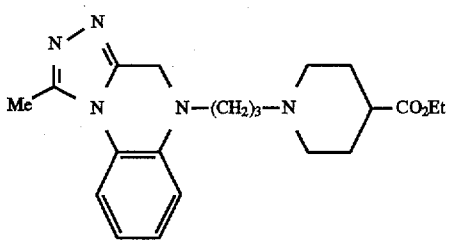

In 18 ml of anhydrous N,N-dimethylformamide, 1.36 g of the compound of Example 13 and 1.86 g of the compound of Example 97 are dissolved and the solution is cooled to −10° C. To the mixture, 10 ml of 1M solution of t-BuOK in tetrahydrofuran is added dropwise and the resulting mixture is stirred at room temperature for 3 hours. After cooling the mixture again, saturated aqueous ammonium chloride solution is added and the resultant is subjected to extraction with chloroform. The organic layer is condensed and purified by column chromatography to obtain 2.01 g of the captioned compound in the form of pale yellow crystals.

mp: 60.5°–61.5° C.

IR(KBr)cm$^{-1}$: 2950,1727,1555,1510,1427,1282,1261, 1238, 1048,746

$^{1}$HNMR(CDCl3) δ: 7.62–6.85(4H,m),4.52(2H,s),4.23 (2H,q, J=7.3),3.49(2H,t,J=7.5),3.00(2H,d,J=6.6),2.86(3H,s), 2.43(2H,d,J=6.6),2.30–1.70(9H,m),1.35(3H,t,J=7.3)

MS: 383(M+)

Example 127

4,5-dihydro-1-methyl-5-[3-[4-hydroxybis(2-thienyl) methyl]piperidin-1-yl]propyl][1,2,4]triazolo[4,3-a] quinoxaline (127)

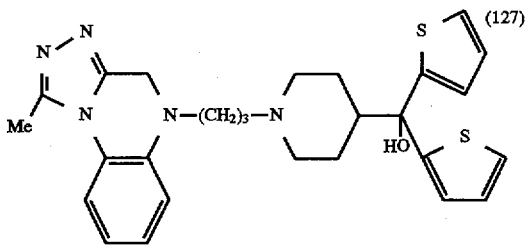

In 20 ml of anhydrous tetrahydrofuran, 1.89 g of the compound of Example 126 is dissolved and the solution is cooled to 0° C. To the solution, 11 ml of 1M solution of 2-thienyl lithium in tetrahydrofuran is added dropwise, and the resulting mixture is stirred at room temperature for 2 hours. To the resulting mixture, saturated aqueous ammonium chloride solution is added and the resultant is subjected to extraction with chloroform. The organic layer is condensed and purified by column chromatography to obtain 1.74 g of the captioned compound in the form of yellow amorphous.

Elementary Analysis: C27H31N5OS2 Calcd.: C,64.13;H, 6.18;N,13.85;S,12.68 Found: C,63.96;H,6.36;N,13.98;S, 12.83

IR(KBr)cm$^{-1}$: 3354,2948,1502,1433,753,700

$^{1}$HNMR(CDCl3) δ: 7.44(1H,dd,J=7.8,1.2),7.21(2H,dd,J= 3.7, 1.2),7.18(1H,t,J=7.3),7.03(2H,dd,J=3.7,1.2),6.96–6.93 (3H,m),6.88(1H,t,J=7.3),4.41(2H,s),3.35(2H,t,J=7.3), 2.93 (2H,d,J=11.0),2.75(3H,s),2.45–2.34(3H,m),2.08–1.92(2H, m),1.79(2H,quint,J=6.8),1.54–1.46(4H,m)

MS: 505(M+)

Example 128

4,5-dihydro-1-methyl-5-[3-(4-benzoylpiperidin-1-yl) propyl][1,2,4]triazolo[4,3-a]quinoxaline (128)

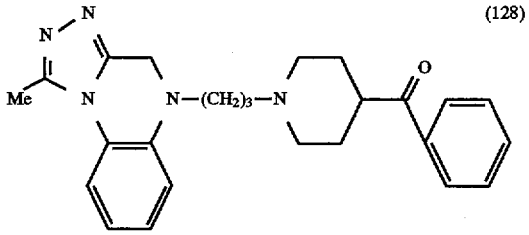

In 15 ml of anhydrous N,N-dimethylformamide, 1.05 g of the compound of Example 13 and 1.50 g of the compound of Example 95 are dissolved and the solution is cooled to 0° C. To the mixture, 6.8 ml of 1M solution of t-BuOK in tetrahydrofuran is added dropwise and the resulting mixture is stirred at room temperature for 1.5 hours. The mixture is again cooled to 0° C. and saturated aqueous ammonium chloride solution is added, followed by extraction with ethyl acetate. The organic layer is condensed and purified by column chromatography to obtain 1.71 g of the captioned compound in the form of colorless amorphous.

mp: 72°–73° C.

Elementary Analysis: C25H29N5O Calcd.: C,72.26;H, 7.03;N,16.85 Found: C,72.41;H,7.17;N,17.04

IR(KBr)cm$^{-1}$: 3451(br.),2928,1710,1686,1560,1504, 1433, 1267,984,748,700

$^{1}$HNMR(CDCl3) δ: 7.95–7.92(2H,m),7.58–7.54(1H,m), 7.47(3H,t, J=7.8),7.35–7.22(1H,m),6.99(1H,d,J=8.3),6.90 (1H,t,J=7.3), 4.44(2H,s),3.41(2H,t,J=7.3),3.30–3.29(1H,m), 2.99(2H,d, J=11.7),2.77(3H,s),2.43(2H,t,J=6.8),2.13(2H,dt, J=10.7, 3.4),1.90–1.82(6H,m)

MS: 415(M+)

Example 129

4,5-dihydro-1-methyl-5-[3-[4-hydroxyphenyl(2-thienyl) methyl]piperidin-1-yl]propyl][1,2,4]triazolo[4,3-a] quinoxaline (129)

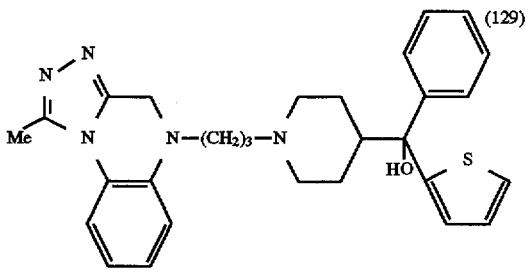

In 20 ml of anhydrous tetrahydrofuran, 2.00 g of the compound of Example 128 is dissolved and the solution is cooled to 0° C. To the mixture, 5.5 ml of 1M solution of 2-thienyl lithium in tetrahydrofuran is added dropwise, and the resulting mixture is stirred at room temperature for 2 hours. Saturated aqueous ammonium chloride solution is added and the resultant is subjected to extraction with chloroform. The organic layer is condensed and purified by column chromatography to obtain 1.44 g of the captioned compound in the form of yellow amorphous.

Elementary Analysis: C29H33N5OS Calcd.: C,69.71;H, 6.65;N,14.02;S,6.42 Found: C,69.45;H,6.84;N,14.13;S,6,65

IR(KBr)cm⁻¹: 3390,2948,1502,1433,748,700

¹HNMR(CDCl3) δ: 7.53(2H,d,J=7.3),7.44(1H,dd,J=7.8, 1.5), 7.32(2H,t,J=7.8),7.22–7.18(3H,m),7.00–6.90(3H,m), 6.89(1H,t,J=7.8),4.41(2H,s),3.36(2H,t,J=7.3),3.02(1H,d, J=11.2),2.93(2H,d,J=11.7),2.75(3H,s),2.45–2.34(3H,m), 2.08–1.92(2H,m),1.79(2H,quint,J=6.8),1.54–1.46(4H,m)

MS: 499(M)+

Example 130

4,5-dihydro-1-methyl-5-[3-[4-[hydroxy(3,4-dimethoxyphenyl)phenylmethyl]piperidin-1-yl]propyl][1,2,4]triazolo[4,3-a]quinoxaline (130)

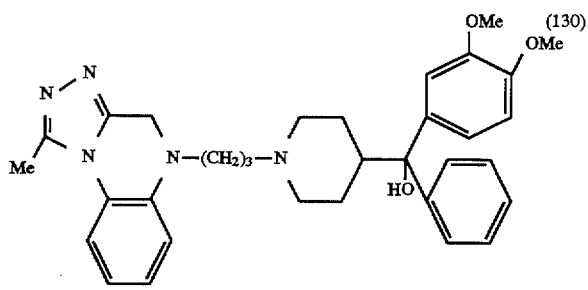

In 15 ml of N,N-dimethylformamide, 0.92 g of the compound of Example 13 and 2.00 g of the compound of Example 101 are dissolved and the solution is cooled to 0° C. To the solution, 9 ml of 1M solution of t-BuOK in tetrahydrofuran is added dropwise and the resulting mixture is stirred at room temperature for 1.5 hours. After cooling the mixture again to 0° C., saturated aqueous ammonium chloride solution is added and the resultant is subjected to extraction with ethyl acetate. The organic layer is condensed and purified by column chromatography to obtain 1.08 g of the captioned compound in the form of colorless amorphous.

Elementary Analysis: C33H39N5O3 Calcd.: C,71.58;H, 7.10;N,12.65 Found: C,71.86;H,7.25;N,12.73

IR(KBr)cm⁻¹: 3370,2946,1504,1433,1259,1141,1027, 745

¹HNMR(CDCl3) δ: 7.49–7.42(3H,m),7.31–7.27(2H,m), 7.21–7.16 (2H,m),7.07(1H,d,J=4.4),6.99–6.86(3H,m),6.79 (1H, d,J=8.8),4.42(2H,s),3.83(6H,d,J=2.9),3.36(2H,t,J=7.3), 2.93(2H,m),2.75(3H,s),2.45–2.30(3H,m),2.08–1.92(2H,m), 1.85–1.80(2H,m),1.54–1.46(4H,m)

MS: 553(M+)

Examples 131–139

The same procedure as in Example 127 is repeated except that 3-tolyl magnesium bromide is used in place of 2-thienyl lithium to obtain compound 134; or that 3-methoxyphenyl magnesium bromide is used in place of 2-thienyl lithium to obtain compound 135.

The same procedure as in Example 130 is repeated except that 96 is used in place of 101 to obtain compound 131; that 99 is used in place of 101 to obtain compound 132; that 100 is used in place of 101 to obtain compound 133; that 102 is used in place of 101 to obtain compound 136; that 103 is used in place of 101 to obtain compound 137; that 104 is used in place of 101 to obtain compound 138; or that 105 is used in place of 101 to obtain compound 139.

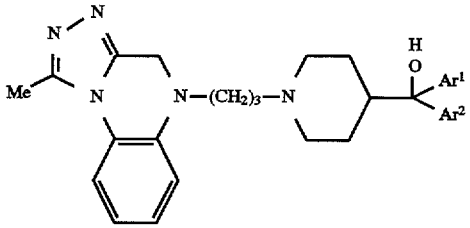

| Compound | Ar1 | Ar2 |
|---|---|---|
| 131 | 4-NMe2-Ph | Ph |
| 132 | 3-Tolyl | Ph |
| 133 | 3-MeO—Ph | Ph |
| 134 | 3-Tolyl | 3-Tolyl |
| 135 | 3-MeO—Ph | 3-MeO—Ph |
| 136 | 2-Tolyl | 2-Tolyl |
| 137 | 2-MeO—Ph | 2-MeO—Ph |
| 138 | 3,4-(MeO)2-Ph | 3,4-(MeO)2-Ph |
| 139 | 2-Furyl | 2-Furyl |

131: 4,5-dihydro-1-methyl-5-[3-[4-[hydroxy(4-dimethylaminophenyl)phenylmethyl]piperidin-1-yl]propyl][1,2,4]triazolo[4,3-a]quinoxaline 132: 4,5-dihydro-1-methyl-5-[3-[4-[hydroxyphenyl(3-tolyl)methyl]piperidin-1-yl]propyl][1,2,4]triazolo[4,3-a]quinoxaline 133: 4,5-dihydro-1-methyl-5-[3-[4-[hydroxy(3-methoxyphenyl)phenylmethyl]piperidin-1-yl]propyl][1,2,4]triazolo[4,3-a]quinoxaline 134: 4,5-dihydro-1-methyl-5-[3-[4-[hydroxybis(3-tolyl)methyl]piperidin-1-yl]propyl][1,2,4]triazolo[4,3-a]quinoxaline 135: 4,5-dihydro-1-methyl-5-[3-[4-[hydroxybis(3-methoxyphenyl)methyl]piperidin-1-yl]propyl][1,2,4]triazolo[4,3-a]quinoxaline 136: 4,5-dihydro-1-methyl-5-[3-[4-[hydroxybis(2-tolyl)methyl]piperidin-1-yl]propyl][1,2,4]triazolo[4,3-a]quinoxaline 137: 4,5-dihydro-1-methyl-5-[3-[4-[hydroxybis(2-methoxyphenyl)methyl]piperidin-1-yl]propyl][1,2,4]triazolo[4,3-a]quinoxaline 138: 4,5-dihydro-1-methyl-5-[3-[4-[hydroxybis(3,4-dimethoxyphenyl)methyl]piperidin-1-yl]propyl][1,2,4]triazolo[4,3-a]quinoxaline 139: 4,5-dihydro-1-methyl-5-[3-[4-[hydroxybis(2-furyl)methyl]piperidin-1-yl]propyl][1,2,4]triazolo[4,3-a]quinoxaline 131: Pale Yellow Amorphous Elementary Analysis: as C33H40N6O Calcd.: C,73.85;H, 7.51;N,15.66 Found: C,73.66;H,7.88;N,15.84

IR(KBr)cm⁻¹: 3370,2942,2794,1611,1560,1506,1431, 1352, 1160,748

¹HNMR(CDCl3) δ: 7.46–7.42(3H,m),7.33–7.25(4H,m), 7.21–7.13(2H,m),6.93(1H,d,J=7.3),6.88(1H,t,J=7.8),6.66 (2H,d, J=9.3),4.42(2H,s),3.36(2H,t,J=6.7),2.92–2.90(8H,m) ,2.76(3H,s),2.42–2.34(3H,m),2.01–1.93(2H,m),1.81(2H, quint, J=6.8),1.49–1.46(4H,m)

MS: 536(M+)

132: Yellow Amorphous

Elementary Analysis: as C32H37N5O Calcd.:C,75.71;H, 7.35;N,13.80 Found: C,75.54;H,7.22;N,13.66

IR(KBr)cm⁻¹: 3330,2948,2814,1557,1506,1433,1352, 911,731

¹HNMR(CDCl3) δ: 7.51(2H,dd,J=8.5,1.2),7.41(1H,dd,J= 7.9, 1.2),7.32–7.25(4H,m),7.21–7.13(3H,m),7.02–6.85(3H, m), 4.42(2H,s),3.36(2H,t,J=6.7),2.91(2H,d,J=10.4),2.75

(3H,s), 2.41-2.34(3H,m),2.31(3H,s),2.01-1.92(2H,m),1.81 (2H,quint, J=6.8),1.51-1.45(4H,m)

MS: 508(M+H)+

133: Colorless Amorphous

Elementary Analysis: as C32H37N5O2 Calcd.: C,73.39;H,7.12;N,13.37 Found: C,73.15;H,7.05;N,13.11

IR(KBr)cm⁻¹: 3302,2948,2812,1601,1557,1504,1433, 1253,787

¹HNMR(CDCl3) δ: 7.50(2H,dd,J=8.5,1.2),7.41(1H,dd,J= 7.9, 1.2),7.27(2H,t,J=7.3),7.20-7.05(5H,m),6.91(1H,d,J= 7.4), 6.86(1H,t,J=7.3),6.69(1H,dd,J=7.3,1.8),4.38(2H,s), 3.75(3H,s),3.33(2H,t,J=6.7),2.91(2H,d,J=10.3),2.72(3H,s), 2.41-2.34(3H,m),1.98-1.92(2H,m),1.79(2H,quint,J=6.8), 1.52-1.49(4H,m)

MS: 523(M+)

134: White Crystal mp: 198°-200.5° C.

Elementary Analysis: as C33H39N5O.0.25(H2O) Calcd.: C,75.32;H,7.57;N,13.31 Found: C,75.33;H,7.53;N,13.28

IR(KBr)cm⁻¹: 3408,2948,1504,750

¹HNMR(CDCl3) δ: 7.41(1H,dd,J=7.8,1.5),7.31(2H,m), 7.26(2H,d, J=7.8),7.20(1H,m),7.18(2H,t,J=7.8),6.98(2H,d, J=7.8),6.93(1H,d,J=8.3),6.88(1H,t,J=7.3),4.42(2H,s),3.36 (2H,t, J=7.3),2.93(2H,d,J=11.7),2.76(3H,s),2.41-2.37(3H, m),2.32(6H,s),2.01-1.92(2H,m),1.81(2H,quint,J=6.8), 1.52-1.43(4H,m)

MS: 521(M+)

135: Pale Yellow Amorphous

Elementary Analysis: as C33H39N5O3 Calcd.: C,71.58;H,7.10;N,12.65 Found: C,71.22;H,7.25;N,12.89

IR(KBr)cm⁻¹: 3408,2944,1601,1502,1433,1249,1046, 772,756

¹HNMR(CDCl3) δ: 7.44(1H,dd,J=7.8,1.2),7.21(2H,t,J= 7.8),7.20 (1H,t,J=7.3),7.09(2H,t,J=2.0),7.06(2H,d,J=7.8), 6.93(1H,d, J=8.3),6.89(1H,t,J=7.3),6.71(2H,dd,J=7.3,2.0), 4.43(2H,s), 3.78(6H,s),3.36(2H,t,J=6.8),2.93(2H,d,J=11.7), 2.76(3H,s), 2.41-2.34(3H,m),1.98-1.92(2H,m),1.79(2H, quint,J=6.8), 1.52-1.26(4H,m)

MS: 554(M+H)

136: Colorless Amorphous

Elementary Analysis: as C33H39N5O Calcd.: C,75.97;H, 7.53;N,13.42 Found: C,76.13;H,7.38;N,13.22

IR(KBr)cm⁻¹: 3320,2930,1504,1475,1460,1433,1379, 1352, 1253,748

¹HNMR(CDCl3) δ: 7.45(1H,dd,J=7.8,1.5),7.22(1H,t,J= 8.3), 7.48-7.15(6H,m),7.12-6.98(2H,m),6.96(1H,d,J=8.3), 6.92(1H, t,J=7.8),4.40(2H,s),3.40(2H,t,J=6.8),3.15(2H,br), 2.76(3H, s),2.58(2H,br.),1.98(6H,br.),2.40-1.50(10H,br)

MS: 521(M+)

137: Pale Yellow Amorphous

Elementary Analysis: as C33H39N5O3 Calcd.: C,71.58;H,7.10;N,12.65 Found: C,71.33;H,7.01;N,12.88

IR(KBr)cm⁻¹: 3496,2944,1504,1487,1468,1433,1288, 1241, 1027,754

¹HNMR(CDCl3) δ: 7.62(2H,d,J=7.9),7.43(1H,dd,J=7.9, 1.8), 7.21(1H,dt,J=7.3,1.8),7.16(2H,dt,J=7.9,1.2),7.05-6.92 (3H,m),6.88(1H,dt,J=7.3,1.2),6.75(2H,dt,J=7.9,1.2), 5.23 (1H,br.),4.41(2H,s),3.50(6H,s),3.39(2H,t,J=6.7),2.97(2H, br.),2.88(1H,s),2.77(3H,s),2.39(2H,br.),1.96(2H,br.), 1.84 (2H,br.),1.77(2H,br.),1.46(2H,br.)

MS: 553(M+)

138: Pale Yellow Amorphous

Elementary Analysis: as C35H43N5O5 Calcd.: C,68.49;H,7.06;N,11.41 Found: C,68.86;H,7.27;N,11.67

IR(KBr)cm⁻¹: 3381,2871,1510,1472,1259,1139,1027, 745

¹HNMR(CDCl3) δ: 7.44(1H,dd,J=7.8,1.5),7.19(1H,t,J= 7.3),7.05(2H,d,J=2.0),6.98-6.87(4H,m),6.79(2H,d,J=8.8), 4.44(2H,s), 3.85(12H,s),3.36(2H,t,J=7.3),2.76(3H,s), 2.45-2.32(3H,m), 2.02-1.90(4H,m),1.79(2H,quint,J=6.8), 1.54-1.46(4H,m)

MS: 613(M+)

139: Yellow Amorphous

Elementary Analysis: as C27H31N5O3 Calcd.: C,68.48;H,6.60;N,14.79 Found: C,68.11;H,6.38;N,14.55

IR(KBr)cm⁻¹: 3360,2948,1562,1504,1475,1433,1352, 1147, 1009,745

¹HNMR(CDCl3) δ: 7.44(1H,dd,J=7.8,1.5),7.39-7.38(2H, m),7.22 (1H,t,J=7.8),6.95(1H,d,J=7.8),6.91(1H,t,J=7.8), 6.37-6.24(4H,m),4.40(2H,s),3.38(2H,t,J=7.3),3.09(2H,br), 2.76(3H,s),2.53(2H,br),2.34(1H,m),2.14(2H,m),1.95(2H,m) ,1.67(2H,m),1.55(2H,br)

MS: 473(M+)

Example 140

4,5-dihydro-1-methyl-5-[3-[4-[(3-methoxyphenyl) phenylmethylene]piperidin-1-yl]propyl][1,2,4]triazolo[4,3, a]quinoxaline (140)

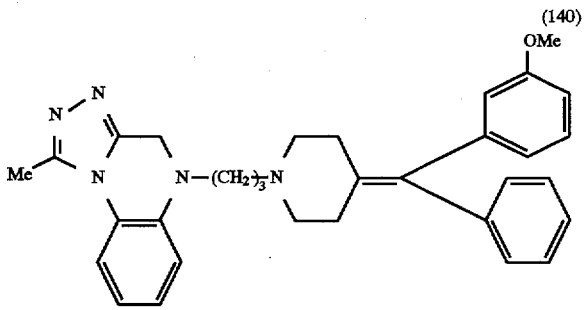

(140)

In 5 ml of ethanol, 1.35 g of the compound of Example 133 is dissolved and 5 ml of concentrated hydrochloric acid is added. The resulting mixture is stirred at 100° C. for 1 hour and cooled. The resultant is neutralized with aqueous sodium carbonate solution and subjected to extraction with chloroform. The organic layer is condensed and the product is recrystallized from isopropanol to obtain 0.89 g of the captioned compound in the form of pale yellow crystals.

mp: 130°-132° C.

Elementary Analysis: as C32H35N5O.0.5(H2O) Calcd.: C,74.68;H,7.05;N,13.61 Found: C,74.61;H,6.76;N,13.86

IR(KBr)cm⁻¹: 2954,2834,1605,1578,1506,1483,1286, 1050,745,702

¹HNMR(CDCl3) δ: 7.45(1H,dd,J=7.9,1.2),7.29-7.12(7H, m),6.96 (1H,d,J=7.9),6.90(1H,t,J=7.3),6.76-6.67(3H,m), 4.46(2H,s), 3.76(3H,s),3.41(2H,t,J=7.3),2.77(3H,s), 2.49-2.04(10H,m),1.87(2H,quint,J=6.8)

MS: 506(M+H)+

Example 141

4,5-dihydro-1-methyl-5-[3-[4-[(4-methoxyphenyl) phenylmethylene]piperidin-1-yl]propyl][1,2,4]triazolo[4,3, a]quinoxaline (141)

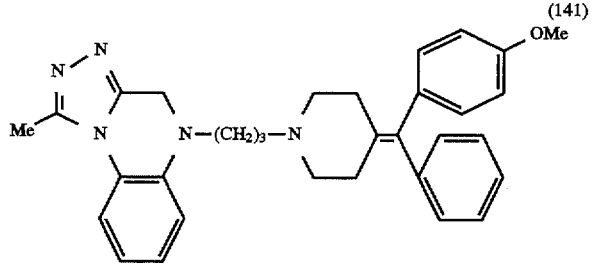

(141)

The same procedure as in Example 130 is repeated except that the compound of Example 114 is used in place of the compound of Example 101 to obtain the captioned compound in the form of white crystals.

mp: 178°–180° C.

Elementary Analysis: as C32H35N5O.0.25(H2O) Calcd.: C,75.34;H,7.01;N,13.73 Found: C,75.37;H,6.90;N,13.92

IR(KBr)cm⁻¹: 2951,2892,1607,1555,1510,1421,1247, 746,702

¹HNMR(CDCl3) δ: 7.45(1H,dd,J=7.8,1.0),7.29–6.80 (12H,m), 4.44(2H,s),3.79(3H,s),3.41(2H,t,J=7.3),2.77(3H, s),2.55–2.38(10H,m),1.87(2H,quint,J=6.8)

MS: 505(M+)

Examples 142–165

The same procedure as in Example 140 is repeated except that 135 is used in place of 133 to obtain compound 143; that 134 is used in place of 133 to obtain compound 147; that 129 is used in place of 133 to obtain compound 164; or that 127 is used in place of 133 to obtain compound 165.

The same procedure as in Example 141 is repeated except that 110 is used in place of 114 to obtain compound 142; that 111 is used in place of 114 to obtain compound 144; that 112 is used in place of 114 to obtain compound 145; that 113 is used in place of 114 to obtain compound 146; that 115 is used in place of 114 to obtain compound 149; that 116 is used in place of 114 to obtain compound 151; that 117 is used in place of 114 to obtain compound 117; that 118 is used in place of 114 to obtain compound 153; that 119 is used in place of 114 to obtain compound 154; that 120 is used in place of 114 to obtain compound 155; that 121 is used in place of 114 to obtain compound 156; that 122 is used in place of 114 to obtain compound 157; that 106 is used in place of 114 to obtain compound 158; that 107 is used in place of 114 to obtain compound 159; that 108 is used in place of 114 to obtain compound 160; that 123 is used in place of 114 to obtain compound 161; that 124 is used in place of 114 to obtain compound 162; or that 125 is used in place of 114 to obtain compound 163.

The same procedure as in Example 46 is repeated except that 4-[bis(3-tolyl)methylene]piperidine is used in place of 4-(diphenylmethylene)piperidine to obtain compound 147; or that 4-[bis(4-methoxyphenyl)methylene]piperidine is used in place of 4-(diphenylmethylene)piperidine to obtain compound 148.

| Compound | Ar¹ | Ar² |
|---|---|---|
| 142 | 3,4-(MeO)2-Ph | Ph |
| 143 | 3-MeO—Ph | 3-MeO—Ph |
| 144 | 2-Tolyl | 2-Tolyl |
| 145 | 2-MeO—Ph | 2-MeO—Ph |
| 146 | 3,4-(MeO)2-Ph | 3,4-(MeO)2-Ph |
| 147 | 3-Tolyl | 3-Tolyl |
| 148 | 4-MeO—Ph | 4-MeO—Ph |
| 149 | 4-Cl—Ph | Ph |
| 150 | 4-Cl—Ph | 4-Cl—Ph |
| 151 | 4-CF3-Ph | Ph |
| 152 | 4-CF3-Ph | 4-CF3—Ph |
| 153 | 4-F—Ph | Ph |
| 154 | 3-Cl—Ph | Ph |
| 155 | 3-Cl—Ph | 3-Cl—Ph |
| 156 | 4-NMe2-Ph | Ph |
| 157 | 4-NMe2-Ph | 4-NMe2-Ph |
| 158 | 4-Tolyl | Ph |
| 159 | 4-Tolyl | 4-Tolyl |
| 160 | 3-Tolyl | Ph |
| 161 | 2-Furyl | 2-Furyl |
| 162 | 2-Pyridyl | Ph |
| 163 | 2-Naphthyl | Ph |
| 164 | 2-Thienyl | Ph |
| 165 | 2-Thienyl | 2-Thienyl |

142: 4,5-dihydro-1-methyl-5-[3-[4-[(3,4-dimethoxyphenyl) phenylmethylene]piperidin-1-yl]propyl][1,2,4]triazolo[4, 3,a]quinoxaline 143: 4,5-dihydro-1-methyl-5-[3-[4-[bis(3-methoxyphenyl) methylene]piperidin-1-yl]propyl][1,2,4]triazolo[4,3,a] quinoxaline 144: 4,5-dihydro-1-methyl-5-[3-[4-[bis(2-tolyl)methylene] piperidin-1-yl]propyl][1,2,4]triazolo[4,3,a]quinoxaline 145: 4,5-dihydro-1-methyl-5-[3-[4-[bis(2-methoxyphenyl) methylene]piperidin-1-yl]propyl][1,2,4]triazolo[4,3,a] quinoxaline 146: 4,5-dihydro-1-methyl-5-[3-[4-[bis(3,4-dimethoxyphenyl)methylene]piperidin-1-yl]propyl][1,2, 4]triazolo[4,3,a]quinoxaline 147: 4,5-dihydro-1-methyl-5-[3-[4-[bis(3-tolyl)methylene] piperidin-1-yl]propyl][1,2,4]triazolo[4,3,a]quinoxaline 148: 4,5-dihydro-1-methyl-5-[3-[4-[bis(4-methoxyphenyl) methylene]piperidin-1-yl]propyl][1,2,4]triazolo[4,3,a] quinoxaline 149: 4,5-dihydro-1-methyl-5-[3-[4-[(4-chlorophenyl) phenylmethylene]piperidin-1-yl]propyl][1,2,4]triazolo[4, 3,a]quinoxaline 150: 4,5-dihydro-1-methyl-5-[3-[4-[bis(4-chlorophenyl) methylene]piperidin-1-yl]propyl][1,2,4]triazolo[4,3,a] quinoxaline 151: 4,5-dihydro-1-methyl-5-[3-[4-[[4-(trifluoromethyl) phenyl]phenylmethylene]piperidin-1-yl]propyl][1,2,4] triazolo[4,3,a]quinoxaline 152: 4,5-dihydro-1-methyl-5-[3-[4-[bis[4-(trifluoromethyl) phenyl]methylene]piperidin-1-yl]propyl][1,2,4]triazolo [4,3,a]quinoxaline 153: 4,5-dihydro-1-methyl-5-[3-[4-[(4-fluorophenyl) phenylmethylene]piperidin-1-yl]propyl][1,2,4]triazolo[4, 3,a]quinoxaline 154: 4,5-dihydro-1-methyl-5-[3-[4-[(3-chlorophenyl)phenylmethylene]piperidin-1-yl]propyl][1,2,4]triazolo[4,3,a]quinoxaline 155: 4,5-dihydro-1-methyl-5-[3-[4-[bis(3-chlorophenyl)methylene]piperidin-1-yl]propyl][1,2,4]triazolo[4,3,a]quinoxaline 156: 4,5-dihydro-1-methyl-5-[3-[4-[(4-dimethylaminophenyl)phenylmethylene]piperidin-1-yl]propyl][1,2,4]triazolo[4,3,a]quinoxaline 157: 4,5-dihydro-1-methyl-5-[3-[4-[bis(4-dimethylaminophenyl)methylene]piperidin-1-yl]propyl][1,2,4]triazolo[4,3,a]quinoxaline 158: 4,5-dihydro-1-methyl-5-[3-[4-[phenyl(4-tolyl)methylene]piperidin-1-yl]propyl][1,2,4]triazolo[4,3,a]quinoxaline 159: 4,5-dihydro-1-methyl-5-[3-[4-[bis(4-tolyl)methylene]piperidin-1-yl]propyl][1,2,4]triazolo[4,3,a]quinoxaline 160: 4,5-dihydro-1-methyl-5-[3-[4-[phenyl(3-tolyl)methylene]piperidin-1-yl]propyl][1,2,4]triazolo[4,3,a]quinoxaline 161: 4,5-dihydro-1-methyl-5-[3-[4-[bis(2-furyl)methylene]piperidin-1-yl]propyl][1,2,4]triazolo[4,3,a]quinoxaline 162: 4,5-dihydro-1-methyl-5-[3-[4-[phenyl(2-pyridyl)methylene]piperidin-1-yl]propyl][1,2,4]triazolo[4,3,a]quinoxaline 163: 4,5-dihydro-1-methyl-5-[3-[4-[(2-naphthyl)phenylmethylene]piperidin-1-yl]propyl][1,2,4]triazolo[4,3,a]quinoxaline 164: 4,5-dihydro-1-methyl-5-[3-[4-[phenyl(2-thienyl)methylene]piperidin-1-yl]propyl][1,2,4]triazolo[4,3,a]quinoxaline 165: 4,5-dihydro-1-methyl-5-[3-[4-[bis(2-thienyl)methylene]piperidin-1-yl]propyl][1,2,4]triazolo[4,3,a]quinoxaline The above-described compounds have the following physical properties:

Compound Spectrum Data

142: Colorless Amorphous
Elementary Analysis: as $C_{33}H_{37}N_5O_2$ Calcd.: C,73.99;H,6.96;N,13.07 Found: C,73.68;H,6.88;N,12.98
IR(KBr)cm$^{-1}$: 2902,2772,1506,1461,1433,1253,1139,1027,750,702
$^1$HNMR(CDCl3) δ: 7.45(1H,dd,J=7.8,1.0),7.30–7.12(6H,m), 6.97(1H,dd,J=8.3,7.3),6.90(1H,t,J=6.8),6.79(1H,d,J=8.3), 6.70–6.62(2H,m),4.44(2H,s),3.86(3H,s),3.80(3H,s), 3.41(2H,t,J=7.3),2.77(3H,s),2.51–2.39(10H,m),1.86(2H, quint, J=6.8)
MS: 535(M+)

143: Pale Yellow Crystal
mp: 125.5°–126.5° C.
Elementary Analysis: as $C_{33}H_{37}N_5O_2$ Calcd.: C,73.99;H,6.96;N,13.07 Found: C,73.92;H,7.12;N,12.97
IR(KBr)cm$^{-1}$: 2952,1578,1504,1431,1286,1048,777,746
$^1$HNMR(CDCl3) δ: 7.45(1H,d,J=7.3),7.21(1H,m),7.19 (2H,t, J=7.9),6.97(1H,d,J=7.9),6.90(1H,t,J=7.9),6.76(1H,d, J=2.4),6.73(3H,d,J=7.3),6.68(2H,t,J=2.4),4.44(2H,s),3.76 (6H,s),3.41(2H,t,J=7.3),2.77(3H,s),2.48–2.04(10H,m),1.87 (2H,quint,J=6.8)
MS: 536(M+H)+

144: Colorless Amorphous
Elementary Analysis: as $C_{33}H_{37}N_5$ Calcd.: C,78.69;H,7.40;N,13.90 Found: C,78.47;H,7.20;N,14.27
IR(KBr)cm$^{-1}$: 2950,2806,1557,1502,1475,1429,1377,1346, 1247,743,
$^1$HNMR(CDCl3) δ: 7.44(1H,dd,J=7.8,1.5),7.21(1H,t,J=7.8), 7.18–7.00(8H,m),6.96(1H,d,J=7.8),6.91(1H,t,J=7.8), 4.40 (2H,s),3.41(2H,t,J=6.8),2.76(3H,s),2.55(2H,m),2.31 (3H,s), 2.17(3H,s),2.45–2.10(8H,m),1.97(2H,br)
MS: 503(M+)

145: Colorless Amorphous
Elementary Analysis: as $C_{33}H_{37}N_5O_2$ Calcd.: C,73.99;H,6.96;N,13.07 Found: C,74.15;H,7.12;N,13.35
IR(KBr)cm$^{-1}$: 2954,1504,1491,1466,1433,1245,1118, 1050, 1027,752
$^1$HNMR(CDCl3) δ: 7.44(1H,dd,J=7.9,1.2),7.24–7.05(6H, m),6.98 (1H,d,J=7.9),6.94–6.82(4H,m),4.43(2H,s), 3.88–3.69(6H,br.),3.41(2H,t,J=7.3),2.77(3H,s),2.60–2.10 (10H,m),1.87(2H,br.)
MS: 535(M+)

146: Colorless Amorphous
Elementary Analysis: as $C_{35}H_{41}N_5O_4$ Calcd.: C,70.56;H,6.94;N,11.76 Found: C,70.44;H,6.88;N,11.92
IR(KBr)cm$^{-1}$: 2890,2806,1512,1461,1249,1139,1027, 750
$^1$HNMR(CDCl3) δ: 7.46(1H,dd,J=8.3,1.5),7.20(1H,t,J= 6.8), 6.98(1H,dd,J=8.3,1.0),6.92(1H,t,J=1.0),6.80(2H,d,J= 8.3), 6.69(2H,dd,J=7.8,2.0),6.62(2H,d,J=1.5),4.45(2H,s), 3.87(6H,s),3.81(6H,s),3.41(2H,t,J=7.3),2.78(3H,s), 2.50–2.41(10H,m),1.87(2H,quint,J=6.8)
MS: 595(M+)

147: White Crystal
mp: 151°–152° C.
Elementary Analysis: as $C_{33}H_{37}N_5$ Calcd.: C,78.69;H, 7.40;N,13.90 Found: C,78.43;H,7.38;N,13.69
IR(KBr)cm$^{-1}$: 2954,1508,777,748
$^1$HNMR(CDCl3) δ: 7.45(1H,dd,J=7.8,1.2),7.21(1H,t,J= 7.3), 7.17(2H,t,J=7.8),7.02–6.88(8H,m),4.44(2H,s),3.41 (2H,t, J=7.3),2.77(3H,s),2.52–2.33(10H,m),2.30(6H,s),1.87 (2H, quint,J=6.8)
MS: 503(M+)

148: Pale Yellow Crystal
mp: 132°–135° C.
Elementary Analysis: as $C_{33}H_{37}N_5O_2$ Calcd.: C,73.99;H,6.96;N,13.07 Found: C,74.12;H,7.03;N,12.85
IR(KBr)cm$^{-1}$: 2952,2838,1607,1510,1245,1176,1035, 835
$^1$HNMR(CDCl3) δ: 7.45(1H,dd,J=7.9,1.2),7.21(1H,t,J= 7.3), 7.04–7.01(4H,m),6.98(1H,d,J=8.5),6.90(1H,t,J=7.9), 6.83–6.80(4H,m),4.44(2H,s),3.81(6H,s),3.43(2H,t,J=7.3), 2.77(3H,s),2.48–2.40(10H,m),1.86(2H,quint,J=6.8),
MS: 535(M+)

149: Pale Yellow Crystal
mp: 165°–167° C.
Elementary Analysis: as $C_{31}H_{32}N_5Cl.0.25(H_2O)$ Calcd.: C,72.36;H,6.37;N,13.61; Cl,6.89 Found: C,72.30;H,6.32;N, 13.51; Cl,6.85
IR(KBr)cm$^{-1}$: 2960,1684,1611,1557,1504,1487,1431, 756
$^1$HNMR(CDCl3) δ: 7.46(1H,dd,J=7.8,6.8),7.31–7.20(7H, m), 7.10–7.04(3H,m),6.97(1H,d,J=8.3),6.91(1H,t,J=8.3), 4.44(2H,s),3.41(2H,t,J=6.8),2.77(3H,s),2.55–2.38(10H,m), 1.87(2H,quint,J=6.8)
MS: 509(M+)

150: Pale Yellow Amorphous
Elementary Analysis: as $C_{31}H_{31}N_5Cl_2$ Calcd.: C,68.38;H,5.74;N,12.86;Cl,13.02 Found: C,68.19;H, 5.62;N,12.55;Cl,12.85
IR(KBr)cm$^{-1}$: 2938,2806,1555,1504,1431,1091,818,756
$^1$HNMR(CDCl3) δ: 7.46(1H,dd,J=8.1,1.5),7.27–7.21(6H, m), 7.04–7.01(3H,m),6.96(1H,d,J=7.3),6.90(1H,t,J=7.3), 4.44(2H,s),3.41(2H,t,J=6.8),2.77(3H,s),2.48–2.37(10H,m), 1.87(2H,quint,J=6.8)
MS: 544(M+H)+

151: Pale Yellow Amorphous
Elementary Analysis: as $C_{32}H_{32}N_5F_3.0.5(H_2O)$ Calcd.: C,69.55;H,6.02;N,12.67;F,10.31 Found: C,69.81;H,5.86;N, 12.71;F,10.51

IR(KBr)cm$^{-1}$: 2951,2810,1613,1555,1504,1431,1325, 1067, 742,702

$^1$HNMR(CDCl3) δ: 7.53(2H,d,J=8.3),7.45(1H,dd,J=7.8, 1.0), 7.38–7.20(6H,m),7.11(2H,d,J=7.3),6.97(1H,d,J=8.3), 6.90(1H,t,J=7.8),4.44(2H,s),3.41(2H,t,J=7.2),2.77(3H,s), 2.57–2.37(10H,m),1.86(2H,quint,J=6.8)

MS: 543(M+)

152: White Crystal
mp: 141°–143° C.

Elementary Analysis: as C33H31N5F6 Calcd.: C,64.80;H,5.11;N,11.45;F,18.64 Found: C,64.67;H,5.08;N, 11.17;F,18.33

IR(KBr)cm$^{-1}$: 2954,1615,1506,1325,1168,1125,1067, 1019,833, 746

$^1$HNMR(CDCl3) δ: 7.56(4H,d,J=7.8),7.46(1H,dd,J=7.8, 1.0), 7.25–7.20(5H,m),6.97–6.89(2H,m),4.45(2H,s),3.41 (2H,t, J=6.8),2.78(3H,s),2.51–2.04(10H,m),1.87(2H,quint, J=6.8)

MS: 611(M+)

153: White Crystal
mp: 178°–180° C.

Elementary Analysis: as C31H32N5F.0.25(H2O) Calcd.: C,74.75;H,6.58;N,14.06;F,3.81 Found: C,74.62;H,6.49;N, 14.22;F,3.83

IR(KBr)cm$^{-1}$: 2886,2821,1603,1555,1506,1431,1350, 1222,745, 702

$^1$HNMR(CDCl3) δ: 7.46(1H,dd,J=8.3,1.5),7.31–7.19(4H, m),7.11–7.06(4H,m),6.99–6.88(4H,m),4.44(2H,s),3.41(2H, t,J=7.3), 2.77(3H,s),2.56–2.32(10H,m),1.86(2H,quint,J= 6.8)

MS: 493(M+)

154: Pale Yellow Crystal
mp: 140°–142° C.

Elementary Analysis: as C31H32N5Cl.0.5(H2O) Calcd.: C,71.72;H,6.41;N,13.49; Cl,6.82 Found: C,71.89;H,6.43;N, 13.71;Cl,6.60

IR(KBr)cm$^{-1}$: 2952,2790,1555,1504,1473,1429,1348, 1286, 1131,745,704

1HNMR(CDCl3) δ: 7.44(1H,dd,J=7.9,1.2),7.30–7.26 (3H,m), 7.23–7.17(4H,m),7.10(2H,d,J=6.7),7.02–6.96(2H, m),6.90(1H,t,J=7.3)4.44(2H,s),3.41(2H, t,J=6.7),2.77(3H,s) ,2.55–2.24(10H,m),1.87(2H,quint,J=6.8)

MS: 509(M+)

155: Colorless Amorphous

Elementary Analysis: as C31H31N5Cl2.H2O Calcd.: C,66.19;H,5.91;N,12.45;Cl,12.60 Found: C,66.35;H, 5.89;N,12.82;Cl,12.51

IR(KBr)cm$^{-1}$: 2954,2774,1591,1562,1502,1473,1429, 1350,748, 714

$^1$HNMR(CDCl3) δ: 7.45(1H,dd,J=8.3,1.5),7.25–7.18(5H, m), 7.10–7.09(2H,m),7.03–6.96(4H,m),4.44(2H,s),3.41(2H, t, J=7.3),2.77(3H,s),2.51–2.36(10H,m),1.86(2H,quint,J= 6.8)

MS: 543(M+)

156: White Crystal
mp: 185°–186° C.

Elementary Analysis: as C33H38N6.0.25(H2O) Calcd.: C,75.75;H,7.42;N,16.06 Found: C,75.56;H,7.31;N,15.81

IR(KBr)cm$^{-1}$: 2892,2806,1609,1522,1510,1352,1129, 818,756, 708

$^1$HNMR(CDCl3) δ: 7.45(1H,dd,J=7.8,1.0),7.28–7.15(5H, m),7.12(2H,d,J=1.5),7.01–6.97(2H,m),6.90(1H,t,J=7.8), 6.66–6.63(2H,m),4.44(2H,s),3.41(2H,t,J=6.7),2.93(6H,s), 2.77(3H,s),2.49–2.39(10H,m),1.86(2H,quint J=6.8)

MS: 518(M+)

157: White Crystal
mp: 189°–191° C.

Elementary Analysis: as C35H43N7.0.25(H2O) Calcd.: C,74.23;H,7.74;N,17.31 Found: C,74.22;H,7.73;N,17.30

IR(KBr)cm$^{-1}$: 2886,2798,1611,1520,1508,1348,1224, 1129,824, 746

$^1$HNMR(CDCl3) δ: 7.45(1H,dd,J=7.9,1.2),7.23(1H,td,J= 8.2, 1.2),7.00–6.89(6H,m),6.64(4H,d,J=8.8),4.43(2H,s), 3.42(2H, t,J=7.3),2.93(12H,s),2.77(3H,s),2.62–2.39(10H, m),1.86(2H,quint,J=6.8)

MS: 561(M+)

158: White Crystal
mp: 187°–189° C.

Elementary Analysis: as C32H35N5.0.25(H2O) Calcd.: C,77.77;H,7.24;N,14.17 Found: C,77.77;H,7.21;N,14.10

IR(KBr)cm$^{-1}$: 2930,2811,1580,1504,1410,1321,764

$^1$HNMR(CDCl3) δ: 7.45(1H,dd,J=8.3,1.5),7.29–6.88 (12H,m), 4.44(2H,s),3.41(2H,t,J=7.3),2.77(3H,s),2.56–2.39 (10H,m),2.32(3H,s),1.87(2H,quint,J=6.8)

MS: 489(M+)

159: White Crystal
mp: 160°–162° C.

Elementary Analysis: as C33H37N5 Calcd.: C,78.69;H, 7.40;N,13.90 Found: C,78.61;H,7.15;N,13.85

IR(KBr) cm$^{-1}$: 2952,2798,1611,1551,1510,1468,1429, 1350, 1282,820,745

$^1$HNMR(CDCl3) δ: 7.45(1H,dd,J=8.3,1.5),7.21(1H,t,J= 8.3),7.08(4H,d,J=7.8),7.01–6.97(5H,m),6.90(1H,t,J=8.3), 4.44(2H,s), 3.43(2H,t,J=7.3),2.77(3H,s),2.48–2.40(10H,m), 2.32(6H,s),1.86(2H,quint,J=6.8)

MS: 504(M+H)+

160: Pale Yellow Crystal
mp: 169°–171° C.

Elementary Analysis: as C32H35N5.0.25(H2O) Calcd.: C,77.77;H,7.24;N,14.17 Found: C,77.47;H,7.13;N,14.26

IR(KBr)cm$^{-1}$: 2952,2892,2792,1611,1555,1504,1470, 1348,745, 708

$^1$HNMR(CDCl3) δ: 7.45(1H,dd,J=7.8,1.5),7.30–7.11(7H, m),7.03–6.88(5H,m),4.44(2H,s),3.41(2H,t,J=7.3),2.77(3H, s),2.52–2.33(10H,m),2.30(3H,s),1.87(2H,quint,J=6.8)

MS: 490(M+H)+

161: Pale Yellow Amorphous

Elementary Analysis: as C27H29N5O2 Calcd.: C,71.19;H,6.42;N,15.37 Found: C,71.08;H,6.22;N,15.17

IR(KBr)cm$^{-1}$: 2952,2902,1555,1508,1429,1348,1288, 1152, 1013,748

$^1$HNMR(CDCl3) δ: 7.47(1H,dd,J=7.82,0.98),7.40(2H,d, J=1.96), 7.24(1H,d,J=8.30),6.99(1H,dd,J=8.30,0.98),6.94 (1H,t, J=7.82),6.40(2H,dd,J=3.42,1.96),6.15(2H,d,J=3.42), 4.42(2H,s),3.45(2H,t,J=6.84),2.78(3H,s),3.10–2.52(10H, m), 2.05(2H,br.)

MS: 455(M+)

162: Pale Yellow Crystal
mp: 183°–185° C.

Elementary Analysis: as C30H32N6.0.25(H2O) Calcd.: C,74.89;H,6.81;N,17.47 Found: C,74.81;H,6.75;N,17.70

IR(KBr)cm$^{-1}$: 2907,2894,1584,1557,1508,1451,1429, 1348,748, 702

$^1$HNMR(CDCl3) δ: 8.60(1H,dd,J=5.5,1.8),7.60(1H,td, 7.9,1.8), 7.45(1H,dd,J=7.9,1.8),7.32–7.10(8H,m),6.98(1H, d,J=7.3), 6.89(1H,t,J=6.7),4.44(2H,s),3.41(2H,t,J=6.7),2.77 (3H,s), 2.57–2.41(10H,m),1.87(2H,quint,J=6.8)

MS: 476(M+)

163: Pale Yellow Amorphous

Elementary Analysis: as C35H35N5.0.25(H2O) Calcd.: C,79.29;H,6.75;N,13.21 Found: C,79.09;H,6.51;N,13.45

IR(KBr)cm$^{-1}$: 2948,2810,1686,1555,1504,1473,1431, 1350,746, 702

$^1$HNMR(CDCl3) δ: 7.80–7.73(3H,m),7.60–7.58(1H,m), 7.47–7.40 (3H,m),7.31–7.16(7H,m),6.98(1H,d,J=7.3),6.90

(1H,t,J=7.9), 4.44(2H,s),3.42(2H,t,J=7.3),2.77(3H,s), 2.62–2.43(10H,m),1.87(2H,quint,J=6.8)

MS: 526(M+H)+

164: Yellow Crystal
mp: 185°–187° C.

Elementary Analysis: as C29H31N5S.0.25(H2O) Calcd.: C,71.65;H,6.53;N,14.41 Found: C,71.62;H,6.60;N,14.20

IR(KBr)cm⁻¹: 2952,1504,1429,750,702

¹HNMR(CDCl3) δ: 7.46(1H,dd,J=7.8,1.5),7.33(2H,t,J= 1.5), 7.25–7.20(3H,m),7.17(2H,d,J=6.8),6.97–6.95(2H,m), 6.90(1H,t,J=7.8),6.79(1H,d,J=3.4), 4.44(2H,s),3.41(2H,t,J=6.7),2.77(3H,s),2.59–2.32(10H,m),1.86(2H,quint,J=6.8)

MS: 481(M+)

165: Yellow Crystal
mp: 175.5°–178° C.

Elementary Analysis: as C27H29N5S2 Calcd.: C,66.50;H,5.99;N,14.36 Found: C,66.13;H,6.07;N,14.07

IR(KBr)cm⁻¹: 2952,2806,1506,1429,750,704

¹HNMR(CDCl3) δ: 7.46(1H,dd,J=8.3,1.5),7.25(2H,dd,J= 5.4, 1.2),7.21(2H,d,J=7.3),6.99–6.95(3H,m),6.90(1H,t,J= 7.8), 6.85(1H,d,J=3.4),4.44(2H,s),3.41(2H,t,J=6.7),2.77 (3H,s), 2.59–2.32(10H,m),1.86(2H,quint,J=6.8)

MS: 487(M+)

Example 166

2-(3-methoxypropylamino)nitrobenzene (166)

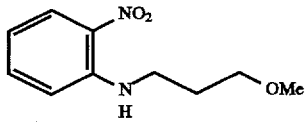

Two hundred ninety five grams of o-chloronitrobenzene and 417 g of 3-methoxypropylamine are stirred at 130° C. for 4.5 hours. To the mixture, ethyl acetate and water are added to carry out extraction. The organic layer is washed with water and dried. The residue is distilled under reduced pressure {132.5°–134.5° C. (0.35 mmHg)} to obtain 356 g of the captioned compound in the form of red oil.

IR(Neat)cm⁻¹: 3384,2928,2874,1622,1574,1516,1421, 1352, 1038,745

¹HNMR(CDCl3) δ: 8.16(2H,dd,J=8.6,1.5),7.42(1H,dt,J= 7.0, 1.5),6.86(1H,d,J=8.8),6.61(1H,td,J=7.0,1.5),3.53(2H,t, J=5.7),3.37(5H,m).1.98(2H,quint,J=6.1)

MS: 210(M)+

Example 167

2-(3-methoxypropylamino)-4-(trifluoromethyl)nitrobenzene (167)

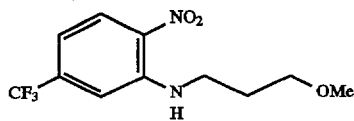

The same procedure as in Example 166 is repeated except that 2-chloro-4-(trifluoromethyl)nitrobenzene is used in place of o-chloronitrobenzene to obtain compound 167 in the form of yellow oil.

bp: 135.5° C.(0.66 mmHg)

IR(Neat)cm⁻¹: 3380,3320,2932,2880,1638,1576,1541, 1439, 1330,1272,1238,1156,1120,1083

¹HNMR(CDCl3) δ: 8.60(1H,brs),8.46(1H,d,J=2.2),7.56 (1H,dd, J=9.5,2.2),6.95(1H,d,J=9.2),3.56(4H,m),3.39(3H, s), 1.56(2H,quint,J=7.2)

MS: 278(M)+

Example 168

2-(3-methoxypropylamino)-4-methyl-nitrobenzene (168)

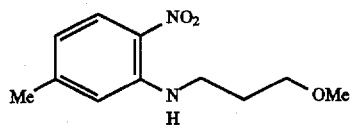

The same procedure as in Example 166 is repeated except that 2-chloro-4-methylnitrobenzene is used in place of o-chloronitrobenzene to obtain compound 168 in the form of yellow oil.

bp: 149°–150° C.(0.7 mmHg)

IR(Neat)cm⁻¹: 3384,2926,2874,1634,1570,1526,1408, 1350, 1270,1236,1189,1158,1122,922

¹HNMR(CDCl3) δ: 8.10(1H,brs),7.96(1H,m),7.26(1H, dd,J=6.4, 2.2),6.79(1H,d,J=8.8),3.60–3.35(7H,m),2.26(3H, s), 1.96(2H,quint,J=6.3)

MS: 224(M)+

Example 169

4-chloro-2-(3-methoxypropylamino)nitrobenzene (169)

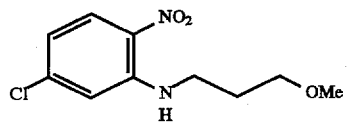

The same procedure as in Example 166 is repeated except that 2,4-dichloronitrobenzene is used in place of o-chloronitrobenzene to obtain compound (169) in the form of yellow oil.

bp: 141° C.(0.12 mmHg)

IR(Neat)cm⁻¹: 3376,3324,2928,2876,1615,1568,1524, 1495, 1473,1415,1338,1311,1265,1220,1154,1122,1067, 839,750

¹HNMR(CDCl3) δ: 8.33(1H,brs),8.11(1H,d,J=9.0),6.87 (1H,d, J=2.2),6.66(1H,dd,J=9.0,2.2),3.60–3.30(7H,m),1.98 (2H, quint,J=5.4)

MS: 244(M)+

Example 170

2-(3-methoxypropylamino)aniline (170)

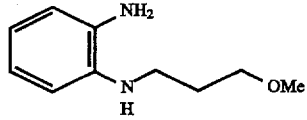

In 500 ml of ethanol and 550 ml of 10% aqueous sodium hydroxide solution, 68 g of the compound of Example 166 is dissolved, and 129 g of zinc powder is added in several times to the mixture at 90° C. under stirring. The resulting mixture is further stirred for 30 minutes. The residue is filtered off and the filtrate is condensed and subjected to extraction with ethyl acetate. The organic layer is washed with water and dried, followed by distillation under reduced pressure {140° C. (1.2 mm Hg)} to obtain 51 g of the captioned compound in the form of colorless oil.

IR(Neat)cm⁻¹: 3390,3342,2928,2874,1626,1601,1512, 1456, 1272,1116,741

¹HNMR(CDCl3) δ: 6.95–6.80(4H,m),3.53(2H,t,J=5.9), 3.35(3H, s),3.22(2H,t,J=6.6),1.93(2H,quint,J=6.1)

Example 171

2-(3-methoxypropylamino)-4-(trifluoromethyl)aniline (171)

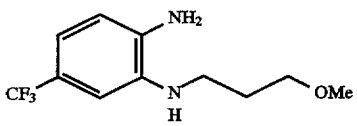

The same procedure as in Example 170 is repeated except that (167) is used in place of (166) to obtain (171) in the form of colorless crystals.

mp: 69°–70° C.

IR(KBr)cm⁻¹: 3374,3258,2950,2874,1638,1611,1541, 1444, 1334,1226,1114,880,737,617

¹HNMR(CDCl3) δ: 7.07(1H,m),6.92(1H,m),6.61(1H,d, J=8.1), 3.55(2H,t,J=5.6),3.37(3H,s),3.27(2H,t,J=6.6), 1.95 (2H,quint,J=6.1)

MS: 248(M)+

Example 172

2-(3-methoxypropylamino)-4-methylaniline (172)

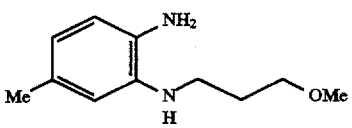

The same procedure as in Example 170 is repeated except that (168) is used in place of (166) to obtain (172) in the form of colorless crystals.

mp: 69°–72° C.

IR(KBr)cm⁻¹: 3374,3308,3226,2864,2840,1589,1518, 1294, 1230,1118,791,770

¹HNMR(CDCl3) δ: 6.56(3H,m),3.59–3.11(10H,m),2.21 (3H,s), 1.92(2H,quint,J=6.3)

MS: 194(M)+

Example 173

4-chloro-2-(3-methoxypropylamino)aniline (173)

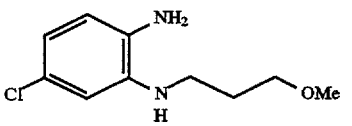

The same procedure as in Example 170 is repeated except that (169) is used in place of (166) to obtain (173) in the form of colorless crystals.

IR(Neat)cm⁻¹: 3400,3346,2930,2876,1623,1599,1512, 1274, 1118,650

¹HNMR(CDCl3) δ: 6.59(3H,s),3.53(2H,t,J=5.8),3.36(3H, s), 3.19(4H,t,J=6.0),1.92(2H,quint,J=6.1)

MS: 214(M)+

Example 174

2-hydroxy-1-(3-methoxypropyl)benzimidazole (174)

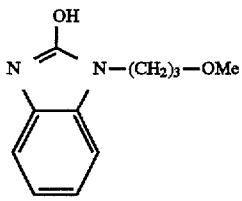

Fifty one grams of the compound of Example 170 and 36 g of urea are stirred at 150° C. for 5 hours. To the mixture, ethyl acetate and water are added and extraction is carried out. The organic layer is washed with 1N hydrochloric acid and brine, and dried. The solvent is evaporated and the product is recrystallized from ethyl acetate to obtain 49 g of the captioned compound in the form of colorless crystals.

mp: 102.5° C.

Elementary Analysis as C11H14N2O2 Calcd.: C;64.06, H;6.84, N;13.58 Found: C;64.02,H;6.82,N;13.71

IR(KBr)cm⁻¹: 3150,1709,1671,1626,1493,1390,1145, 1118,739

¹HNMR(CDCl3) δ: 10.15(1H,brs),7.20–7.00(4H,m),4.00 (2H,t, J=6.8),3.42(2H,t,J=5.7),3.34(3H,s),2.04(2H,quint,J= 6.5)

MS: 206(M)+

Example 175

2-hydroxy-1-(3-methoxypropyl)-6-(trifluoromethyl) benzimidazole (175)

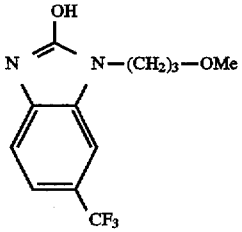

The same procedure as in Example 174 is repeated except that (171) is used in place of (170) to obtain (175) in the form of colorless crystals.

mp: 83°–84° C.

IR(KBr)cm⁻¹: 3200,2928,2884,1715,1678,1491,1334, 1243, 1149,1135,1118

¹HNMR(CDCl3) δ: 7.40–7.08(3H,m),4.04(2H,t,J=6.9), 3.41(2H,t,J=5.7),3.34(3H,s),2.04(2H,quint,J=6.0)

MS: 274(M)+

Example 176

2-hydroxy-1-(3-methoxypropyl)-6-methylbenzimidazole (176)

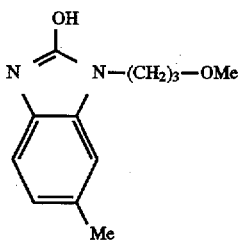

(176)

The same procedure as in Example 174 is repeated except that (172) is used in place of (170) to obtain (176) in the form of colorless crystals.

mp: 118.5°–120° C.

IR(KBr)cm$^{-1}$: 3160,2964,1702,1665,1512,1481,1396, 1346, 1118,803

$^1$HNMR(CDCl3) δ: 9.98(1H,brs),6.91(3H,m),3.97(2H,t, J=6.9), 3.41(2H,t,J=5.9),3.34(3H,s),2.37(3H,s), 2.02(2H, quint,J=6.5)

Example 177

6-chloro-2-hydroxy-1-(3-methoxypropyl)benzimidazole (177)

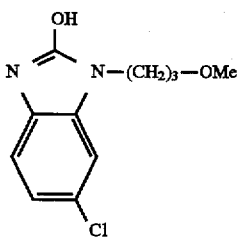

(177)

The same procedure as in Example 174 is repeated except that (173) is used in place of (170) to obtain (177) in the form of colorless crystals.

IR(KBr)cm$^{-1}$: 3158,3058,2988,2896,2836,1688,1630, 1605, 1491,1400,1388,1375,1114,886,801,677,555

Example 178

2-chloro-1-(3-methoxypropyl)benzimidazole (178)

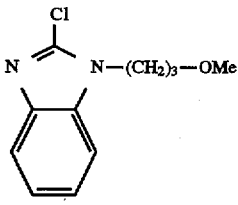

(178)

To 49 g of the compound of Example 174, 100 ml of phosphorus oxychloride is added and the mixture is heated to reflux for 30 minutes. After cooling the mixture, the mixture is poured into iced water and converted to basic condition with 40% aqueous sodium hydroxide solution. The resultant is subjected to extraction with ethyl acetate. The organic layer is washed with water and dried, followed by distillation under reduced pressure {127.5° C. (0.07 mmHg)} to obtain 33 g of the captioned compound in the form of colorless oil.

IR(Neat)cm$^{-1}$: 3060,2930,2876,1618,1473,1452,1379, 1122, 926,745

$^1$HNMR(CDCl3) δ: 7.80–7.05(4H,m),4.31(2H,t,J=6.8), 3.33(5H,m),2.07(2H,quint,J=5.7)

MS: 224(M)+

Example 179

2-chloro-1-(3-methoxypropyl)-6-(trifuluoromethyl) benzimidazole (179)

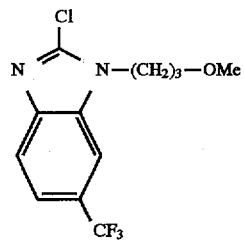

(179)

The same procedure as in Example 178 is repeated except that (175) is used in place of (174) to obtain (179) in the form of colorless crystals.

mp: 45°–53° C.

bp: 103°–106° C.(0.02 mmHg)

IR(KBr)cm$^{-1}$: 2950,2880,2838,1709,1630,1473,1462, 1379, 1365,1328,1207,1162,1110,1050,928,890,822

$^1$HNMR(CDCl3) δ: 7.98–7.50(3H,m),4.36(2H,t,J=6.7), 3.33(5H,m),2.09(2H,quint,J=5.9)

MS: 292(M)+

Example 180

2-chloro-1-(3-methoxypropyl)-6-methylbenzimidazole (180)

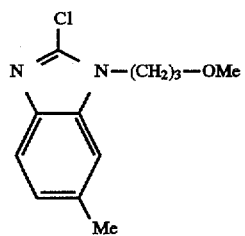

(180)

The same procedure as in Example 178 is repeated except that (176) is used in place of (174) to obtain (180) in the form of colorless crystals.

mp: 40°–44° C.

bp: 115°–117° C.(0.07 mmHg)

IR(KBr)cm$^{-1}$: 2926,2828,1475,1456,1375,1218,1123, 789

$^1$HNMR(CDCl3) δ: 7.47–7.0(3H,m),4.28(2H,t,J=6.7), 3.32(5H,m),2.46(3H,s),2.06(2H,quint,J=6.1)

MS: 238(M)+

Example 181

2,6-dichloro-1-(3-methoxypropyl)benzimidazole (181)

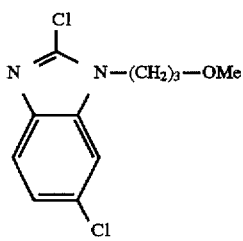

(181)

The same procedure as in Example 178 is repeated except that (177) is used in place of (174) to obtain (181) in the form of colorless crystals.

IR(Neat)cm$^{-1}$: 3074,2928,2878,1717,1613,1470,1450, 1379, 1270,1122,810

$^1$HNMR(CDCl3) δ: 7.60(1H,d,J=8.6),7.33(1H,dd,J=8.6, 2.0), 7.19(1H,d,J=2.0),4.28(2H,t,J=6.7),3.37–3.24(5H,m), 2.06(2H,quint,J=6.0)

MS: 258(M)+

Example 182

9-(3-methoxypropyl)-3-methyl-9H-[1,2,4]triazolo[4,3-a]benzimidazole (182)

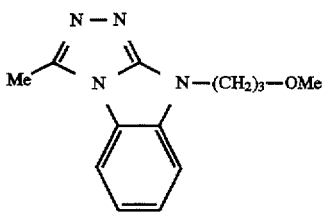

(182)

To 33 g of the compound of Example 178, 350 ml of ethanol and 315 ml of 80% hydrazine hydrate are added and the resulting mixture is heated to reflux for 22 hours. The reaction mixture is condensed to dryness and 500 ml of n-butanol and 70 ml of triethyl orthoacetate are added to the residue. The resulting mixture is heated to reflux for 2 hours and the solvent is evaporated. The residue is purified by silica gel column chromatography (chloroform:methanol= 19:1) and washed with ethyl acetate:hexane=2:1 to obtain 25 g of the captioned compound in the form of colorless crystals.

mp: 74°–75° C.

IR(KBr)cm$^{-1}$: 3400,2930,1626,1603,1499,1479,1120, 748

$^1$HNMR(CDCl3) δ: 7.70–7.05(4H,m),4.27(2H,t,J=6.8), 3.39(2H, t,J=5.7),3.31(3H,s),2.80(3H,s),2.21(2H,quint,J= 5.7)

MS: 244(M)+

Example 183

3-ethyl-9-(3-methoxypropyl)-9H-[1,2,4]triazolo [4,3-a]benzimidazole (183)

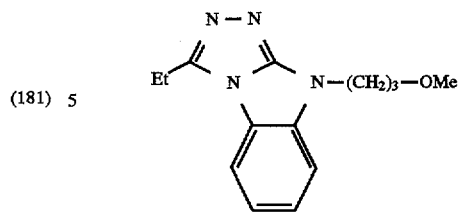

(183)

The same procedure as in Example 182 is repeated except that triethyl orthopropionate is used in place of triethyl orthoacetate to obtain (183) in the form of yellow oil.

IR(Neat)cm$^{-1}$: 3400,2980,2940,2878,1623,1603,1495, 1477, 1433,1120,748

$^1$HNMR(CDCl3) δ: 7.65–7.0(4H,m),4.28(2H,t,J=6.7), 3.58–3.05(7H,m),2.22(2H,quint,J=6.2),1.50(3H,t,J=7.7)

MS: 258(M)+

Example 184

9-(3-methoxypropyl)-3-propyl-9H-[1,2,4]triazolo[4,3-a]benzimidazole (184)

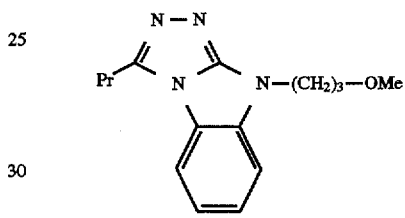

(184)

The same procedure as in Example 182 is repeated except that triethyl orthobutyrate is used in place of triethyl orthoacetate to obtain (184) in the form of yellow oil.

IR(Neat)cm$^{-1}$: 3400,2966,2934,2876,1622,1603,1495, 1477, 1323,746

$^1$HNMR(CDCl3) δ: 7.65–7.10(4H,m),4.27(2H,t,J=6.8), 3.40(2H,t,J=5.8),3.31(3H,s),3.11(2H,t,J=7.6),2.36–1.8(4H, m),1.10(3H,t,J=7.4)

MS: 272(M)+

Example 185

9-(3-methoxypropyl)-3-methyl-7-(trifluoromethyl)-9H-[1, 2,4]triazolo[4,3-a]benzimidazole (185)

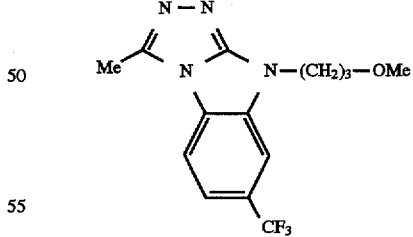

(185)

The same procedure as in Example 182 is repeated except that (179) is used in place of (178) to obtain (185) in the form of pink crystals.

mp: 190°–195° C.

IR(KBr)cm$^{-1}$: 3054,2936,2884,1638,1586,1504,1330, 1296, 1276,1270,1162,1137,1120,1102,1062

$^1$HNMR(CDCl3) δ: 7.82–7.64(2H,m),7.43(1H,d,J=8.6), 4.32(2H,t,J=6.7),3.38(2H,t,J=5.5),3.30(3H,s),2.84(3H,s), 2.23(2H,quint,J=5.8)

MS: 312(M)+

Example 186

3,7-dimethyl-9-(3-methoxypropyl)-9H-[1,2,4]triazolo[4,3-a]benzimidazole (186)

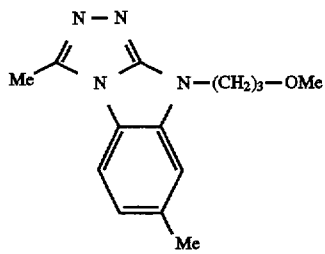
(186)

The same procedure as in Example 182 is repeated except that (180) is used in place of (178) to obtain (186) in the form of pink crystals.

mp: 113°–114° C.

IR(KBr)cm$^{-1}$: 3058,2878,1630,1591,1495,1450,1437, 1379, 1122,1019,951,822

$^{1}$HNMR(CDCl3) δ: 7.38–7.2(3H,m),4.23(2H,t,J=6.8), 3.38(2H,t, J=5.7),3.30(3H,s),2.79(3H,s),2.49(3H,s),2.19 (quint,J=6.0)

MS: 258(M+)

Example 187

7-chloro-9-(3-methoxypropyl)-3-methyl-9H-[1,2,4]triazolo[4,3-a]benzimidazole (187)

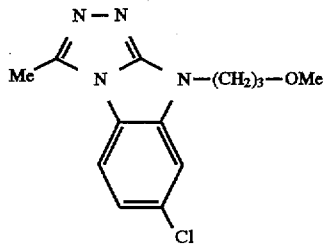
(187)

The same procedure as in Example 182 is repeated except that (181) is used in place of (178) to obtain (187) in the form of colorless crystals.

mp: 136° C.

Elementary Analysis: as C13H15N4OCl Calcd.: C;56.02, H;5.42,N;20.10,Cl;12.70 Found: C;55.90,H;5.40,N;20.03, Cl;12.60

IR(KBr)cm$^{-1}$: 2926,2872,1626,1603,1589,1495,1435, 1427, 1123,826

$^{1}$HNMR(CDCl3) δ: 7.50(1H,d,J=8.6),7.36(1H,d,J=2.0), 7.18(1H, dd,J=8.6,2.0),4.24(2H,t,J=6.7),3.37(2H,t,J=5.5), 3.31(3H, s),2.78(3H,s),2.20(2H,quint,J=6.3)

MS: 278(M+)

Example 188

2-chloro-3-[3-[4-(diphenylmethyl)piperazin-1-yl]propyl] benzimidazole (188)

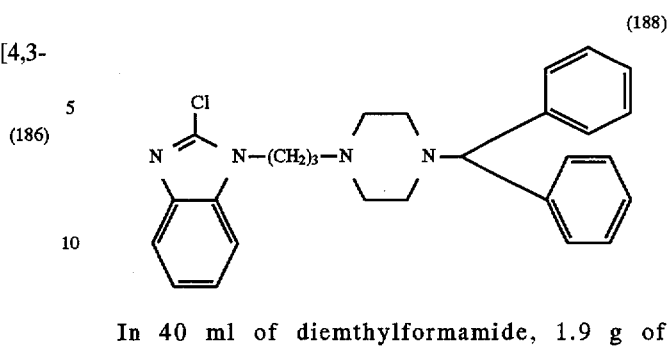
(188)

In 40 ml of diemthylformamide, 1.9 g of 2-chlorobenzimidazole and 4.3 g of 1-(3-chloropropyl)-4-(diphenylmethyl)piperazine are dissolved and 0.78 g of 60% sodium hydride is added at room temperature under stirring. The resulting mixture is stirred at 50° C. for 8 hours and ethyl acetate and water are added to carry out extraction. The organic layer is washed with water and dried. The solvent is evaporated and the residue is purified by silica gel column chromatography (ethyl acetate:hexane=1:1) to obtain 3.3 g of the captioned compound in the form of oil.

IR(Neat)cm$^{-1}$: 2962,2814,1470,1448,1379,1154,1139, 1009, 745,706

1NMR(CDCl3) δ: 7.66(1H,m),7.45–7.15(13H,m),4.25 (2H,t, J=6.8),4.22(1H,s),2.41(8H,s),2.35(2H,t,J=6.2), 1.97 (2H,quint,J=6.8)

MS: 444(M)+

Example 189

3-methyl-9-[3-[4-(diphenylmethyl)piperazin-1-yl]propyl]-9H-[1,2,4]triazolo[4,3-a]benzimidazole dihydrochloride (189)

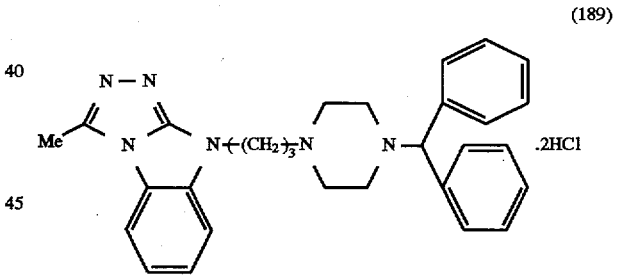
(189)

In 30 ml of ethanol, 3.3 g of the compound of Example 188 is dissolved and 18 ml of hydrazine monohydrate is added. The resulting mixture is heated to reflux for 28 hours and water and ethyl acetate are added thereto to carry out extraction. The organic layer is dried and 1.3 g of triethyl orthoacetate and 40 ml of xylene are added, followed by stirring at 160° C. for 5 hours. The solvent is evaporated and purified by silica gel column chromatography (ethyl acetate-ethanol) to obtain 0.67 g of oil. This oil is dissolved in ethyl acetate and hydrogen chloride gas is blown. The generated crystals are separated by filtration and dried to obtain 0.68 g of the captioned compound.

mp: 147°–157° C.

Example 190

2-chloro-3-[3-[4-(diphenylmethyl)piperazin-1-yl]ethyl] benzimidazole (190)

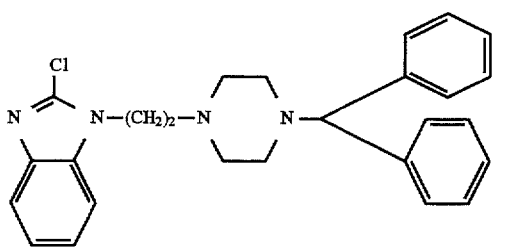

In 20 ml of DMF, 0.81 g of 2-chlorobenzimidazole and 2.1 g of 1-(2-chloroethyl)-4-(diphenylmethyl)piperazine hydrochloric acid salt are dissolved and 0.46 g of 60% sodium hydride is added. The resulting mixture is stirred at room temperature for 1 hour and then at 50° C. for 2 hours. Ethyl acetate and water are added to the resultant to carry out extraction and the organic layer is washed with water and dried. The product is recrystallized from ethyl acetate to obtain 1.2 g of the captioned compound in the form of colorless crystals.

mp: 176°–178° C.

IR(KBr)cm$^{-1}$: 2812,1473,1452,1392,1156,1009,745,706

1NMR(CDCl3) δ: 7.80–7.05(14H,m),4.27(2H,t,J=7.0), 4.19(1H,s),2.71(2H,t,J=7.0),2.5–2.3(8H,m)

MS: 430(M+)

Example 191

3-methyl-9-[3-[4-(diphenylmethyl)piperazin-1-yl]ethyl]-9H-[1,2,4]triazolo[4,3-a]benzimidazole fumaric acid salt (191)

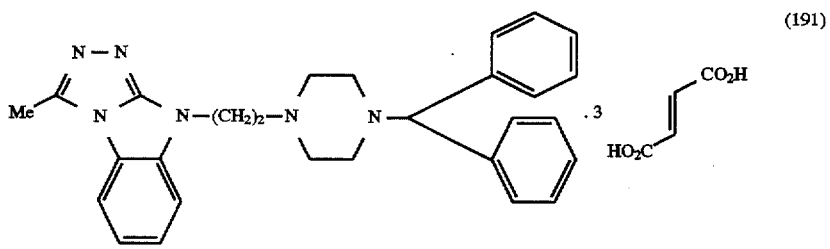

To 0.69 g of the compound of Example 190, 30 ml of ethanol and 6 ml of 80% hydrazine hydrate are added and the resulting mixture is heated to reflux for 12 hours. The mixture is condensed to dryness and ethyl acetate and water are added to carry out extraction. The organic layer is washed with water and dried. To the residue, 10 ml of triethyl orthoacetate is added and the resultant is stirred at 100° C. for 17 hours. The resultant is condensed and ethyl acetate and water are added to carry out extraction. The organic layer is washed with water and dried. The residue is subjected to purification by silica gel column chromatography (ethyl acetate-ethyl acetate:ethanol=3:1) to obtain 0.16 g of 3-methyl-9-[3-[4-(diphenylmethyl)piperazin-1-yl]ethyl]-9H-[1,2,4]triazolo[4,3-a]benzimidazole. This product is dissolved in methanol and 0.12 g of fumaric acid in methanol is added. The resultant is condensed and dried to obtain 0.27 g of the captioned compound.

mp: 190°–194° C.

Elementary Analysis: as C28H30N6.3(C4H4O4).H2O Calcd.: C;58.81,H;5.43,N;10.29 Found: C;58.81,H;5.48, N;10.04

Example 192

3-methyl-9-[3-[4-(3-indolyl)piperidin-1-yl]propyl]-9H-[1,2,4]triazolo[4,3-a]benzimidazole fumaric acid salt (192)

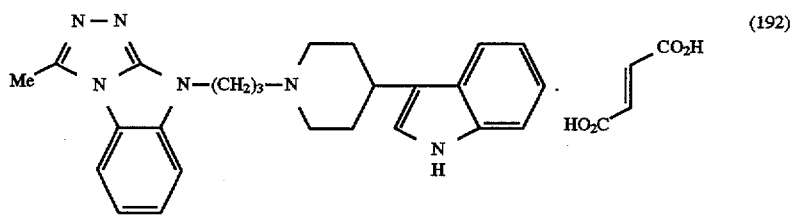

To 22.6 g of the compound of Example 182, 200 ml of 30% hydrobromic acid-acetic acid solution is added and the resulting mixture is stirred at 70° C. for 5 minutes and then at 100° C. for 3 hours. The solution is condensed to dryness and the residue is dissolved in 200 ml of dimethylformamide. To the solution, 21.4 g of 4-(3-indolyl)piperidine and 51.1 g of sodium carbonate are added and the resultant is stirred at room temperature for 30 minutes and at 60° C. for 1 hour. The reaction mixture is poured into water and the resultant is subjected to extraction with ethyl acetate. The organic layer is washed with water and dried. The solvent is evaporated and the residue is subjected to purification by silica gel column chromatography (ethyl acetate:ethanol= 2:1) to obtain 17.1 g of oil. This oil is dissolved in 150 ml of ethanol and a solution containing 4.8 g of fumaric acid in 150 ml of ethanol is added. The precipitated colorless crystals are separated by filtration and dried to obtain 19.0 g of the captioned compound in the form of colorless crystals.

mp: 209°–221° C.

Elementary Analysis: as C25H28N6.C4H4O4.1/2H2O Calcd.: C;64.79,H;6.18,N;15.63 Found: C;64.60,H;6.05, N;15.39

Examples 193–207

The same procedure as in Example 192 is repeated except that the following compounds are used in place of 4-(3-indolyl)piperidine. That is, 4-(5-chloro-3-indolyl)piperidine is used to obtain compound 195; 4-(5-fluoro-3-indolyl) piperidine is used to obtain compound 196; 4-(5-methyl-3- indolyl)piperidine is used to obtain compound 197; 4-(hydroxydiphenylmethyl)piperidine is used to obtain compound 198; 4-[hydroxybis(4-fluorophenyl)methyl]piperidine is used to obtain compound 199; 4-(diphenylmethoxy)piperidine is used to obtain compound 200; 4-(diphenylmethylene)piperidine is used to obtain compound 201; 4-[bis(4-fluorophenyl)methylene]piperidine is used to obtain compound 202; 4-(5H-dibenzo[a,d]cyclohepten-5-ylidene)piperidine is used to obtain compound 206; or 4-(10,11-dihydro-5H-dibenzo[a,d]cyclohepten-5-ylidene)piperidine is used to obtain compound 207. The same procedure as in Example 192 is repeated except that 183 is used in place of 182 to obtain compound 193; that 184 is used in place of 182 to obtain compound 194; that 185 is used in place of 182 to obtain compound 203; that 186 is used in place of 182 to obtain compound 204; or that 187 is used in place of 182 to obtain compound 205.

-continued
| Compound | Structural Formula | |
|---|---|---|
| 199 | 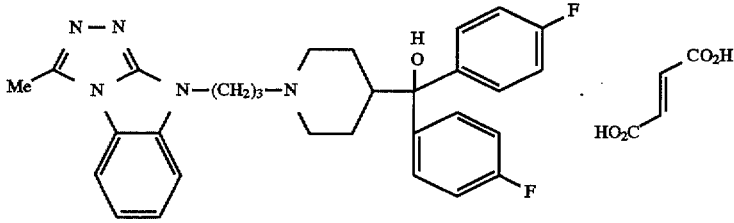 | (199) |
| 200 | 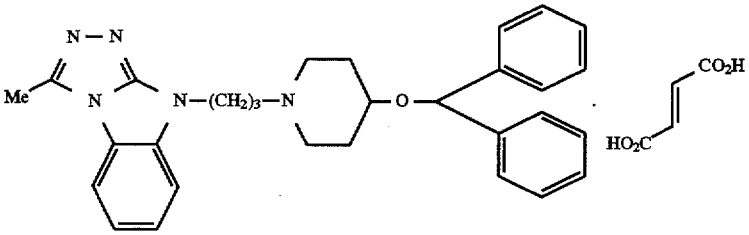 | (200) |
| 201 | 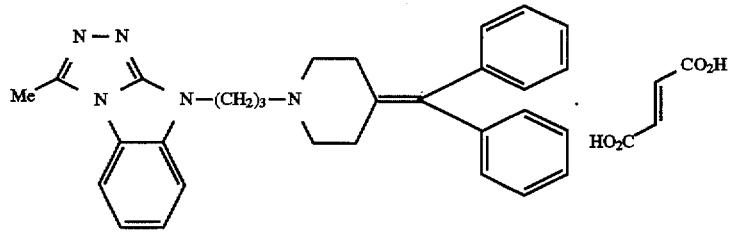 | (201) |
| 202 | 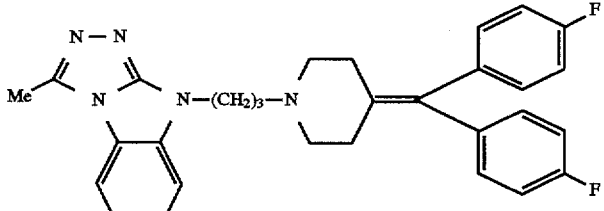 | (202) |
| 203 | 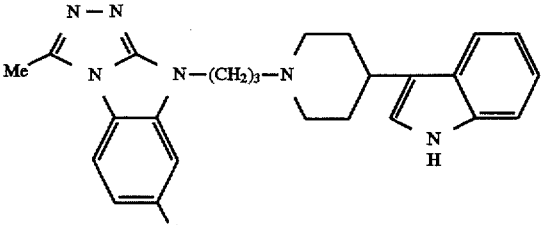 | (203) |
| 204 | 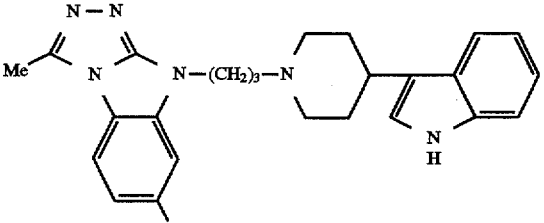 | (204) |

| Compound | Structural Formula |
|---|---|
| 205 | (205) |
| 206 | (206) |
| 207 | (207) |

193: 3-ethyl-9-[3-[4-(3-indolyl)piperidin-1-yl]propyl]-9H-[1,2,4]triazolo[4,3-a]benzimidazole fumaric acid salt 194: 3-propyl-9-[3-[4-(3-indolyl)piperidin-1-yl]propyl]-9H-[1,2,4]triazolo[4,3-a]benzimidazole fumaric acid salt 195: 3-methyl-9-[3-[4-(5-chloro-3-indolyl)piperidin-1-yl]propyl]-9H-[1,2,4]triazolo[4,3-a]benzimidazole 196: 3-methyl-9-[3-[4-(5-fluoro-3-indolyl)piperidin-1-yl]propyl]-9H-[1,2,4]triazolo[4,3-a]benzimidazole 197: 3-methyl-9-[3-[4-(5-methyl-3-indolyl)piperidin-1-yl]propyl]-9H-[1,2,4]triazolo[4,3-a]benzimidazole 198: 3-methyl-9-[3-[4-(hydroxydiphenylmethyl)piperidin-1-yl]propyl]-9H-[1,2,4]triazolo[4,3-a]benzimidazole fumaric acid salt 199: 3-methyl-9-[3-[4-[hydroxybis(4-fluorophenyl)methyl]piperidin-1-yl]propyl]-9H-[1,2,4]triazolo[4,3-a]benzimidazole fumaric acid salt 200: 3-methyl-9-[3-[4-(diphenylmethoxy)piperidin-1-yl]propyl]-9H-[1,2,4]triazolo[4,3-a]benzimidazole fumaric acid salt 201: 3-methyl-9-[3-[4-(diphenylmethylene)piperidin-1-yl]propyl]-9H-[1,2,4]triazolo[4,3-a]benzimidazole fumaric acid salt 202: 3-methyl-9-[3-[4-[bis(4-fluorophenyl)methylene]piperidin-1-yl]propyl]-9H-[1,2,4]triazolo[4,3-a]benzimidazole 203: 3-methyl-7-(trifluoromethyl)-9-[3-[4-(3-indolyl)piperidin-1-yl]propyl]-9H-[1,2,4]triazolo[4,3-a]benzimidazole 204: 3-methyl-7-methyl-9-[3-[4-(3-indolyl)piperidin-1-yl]propyl]-9H-[1,2,4]triazolo[4,3-a]benzimidazole 205: 3-methyl-7-chloro-9-[3-[4-(3-indolyl)piperidin-1-yl]propyl]-9H-[1,2,4]triazolo[4,3-a]benzimidazole 206: 3-methyl-9-[3-[4-(5H-dibenzo[a,d]cyclohepten-5-ylidene)piperidin-1-yl]propyl]-9H-[1,2,4]triazolo[4,3-a]benzimidazole 207: 3-methyl-9-[3-[4-(10,11-dihydro-5H-dibenzo[a,d]cyclohepten-5-ylidene)piperidin-1-yl]propyl]-9H-[1,2,4]triazolo[4,3-a]benzimidazole The physical properties of the above-described compounds are as follows:

193: Colorless Crystal
mp: 173°–175° C.
Elementary Analysis: as C26H30N6.1/2(C4H4O4.H2O)
Calcd.: C;68.13,H;7.14,N;17.02 Found: C;68.23,H;7.05, N;16.63

194: Colorless Crystal
mp: 150°–152° C.
Elementary Analysis: as C27H32N6.1/2C4H4O4.H2O
Calcd.: C;67.42,H;7.02,N;16.27 Found: C;67.98,H;7.29, N;15.68

195: Colorless Amorphous
mp: 138°–142° C.
Elementary Analysis: as C25H27N6Cl.C4H4O4.3/2H2O
Calcd.: C;59.03,H;5.80,N;14.24,Cl;6.00 Found: C;59.53, H;5.84,N;13.59,Cl;5.54

196: Colorless Crystal
mp: 192°–193° C.
Elementary Analysis: as C25H27N6F Calcd.: C;69.75, H;6.32,N;19.52,F;4.41 Found: C;69.62,H;6.28,N;19.31, F;4.39
IR(KBr) cm$^{-1}$: 3200,2950,2936,1624,1605,1495,1477, 1466, 1446,1381,1344,1164,938,799,745
$^1$HNMR(CDCl3) δ: 8.30(1H,brs),7.59(1H,d,J=7.9), 7.41–7.35(2H, m),7.28–7.19(3H,m),7.01(1H,d,J=2.4),6.91

(1H,td,J=6.7, 2.4),4.27(2H,t,J=6.7),2.92(2H,m),2.80(3H,s), 2.72(1H,m), 2.43(2H,t,J=6.7),2.17(2H,quint,J=6.7),2.06 (2H,m), 1.98(2H,m),1.70(2H,qd,J=9.0,3.8)

MS: 430(M)+

197: Colorless Crystal mp: 221°–224° C.

Elementary Analysis: as C26H30N6.1/2H2O Calcd.: C;71.69,H;7.17,N;19.29 Found: C;71.87,H;7.03,N;19.25

IR(KBr) cm⁻¹: 3400,3300,2926,1626,1603,1499,1477, 1444,741

¹HNMR(CDCl3) δ: 8.03(1H,brs),7.59(1H,d,J=7.8), 7.43–7.35(3H, m),7.25–7.18(2H,m),7.00(1H,dd,J=6.8,1.5), 6.93(1H,d, J=2.0),4.27(2H,t,J=6.8),2.95(2H,m),2.80(3H,s), 2.78(1H,m), 2.45(5H,m),2.18(2H,quint,J=6.8),2.11–2.0(4H, m),1.25(2H,m)

MS: 426(M+)

198: Colorless Amorphous mp: 130°–135° C.

Elementary Analysis: as C30H33N5O.C4H4O4.3/4H2O Calcd.: C;67.03,H;6.37,N;11.49 Found: C;67.18,H;6.40, N;11.15

199: Colorless Amorphous mp: 130°–136° C.

Elementary Analysis: as C30H31N5OF2.C4H4O4.H2O Calcd.: C;62.86,H;5.74,N;10.78,F;5.85 Found: C;62.72, H;5.76,N;10.43,F;5.61

200: Colorless Crystal mp: 119.5°–121° C.

Elementary Analysis: as C30H33N5O.C4H4O4.1/4H2O Calcd.: C;68.04,H;6.25,N;11.67 Found: C;67.86,H;6.24, N;11.65

201: Colorless Amorphous mp: 103°–106° C.

Elementary Analysis: as C30H31N5.C4H4O4.3/4H2O Calcd.: C;69.08,H;6.22,N;11.85 Found: C;69.01,H;6.16, N;11.55

202: Pale Yellow Amorphous

IR(KBr) cm⁻¹: 3400,2954,1626,1603,1506,1220,835, 746,559

¹HNMR(CDCl3) δ: 7.59(1H,d,J=7.8),7.38(2H,m),7.21 (1H,m), 7.06–6.94(8H,m),4.26(2H,t,J=6.8),2.80(3H,s), 2.45–2.30(10H,m),2.15(2H,quint,J=6.5)

MS: 498(M+H)+

203: Pale Pink Crystal mp: 173°–182° C.

IR(KBr) cm⁻¹: 3400,3250,2928,1638,1605,1499,1325, 1270, 1160,1118,739

¹HNMR(CDCl3) δ: 8.06(1H,brs),7.81(1H,s),7.66(1H,d, J=8.8), 7.62(1H,d,J=7.8),7.53(1H,d,J=8.3),7.36(1H,d,J=7.8) ,7.18(1H,t,J=7.6),7.10(1H,t,J=7.6),6.96(1H,d,J=2.4),4.33 (2H,t, J=6.5),2.90(2H,m),2.83(4H,m),2.42(2H,t,J=6.6), 2.19 (2H,quint,J=6.6),2.10–2.04(4H,m),1.70(2H,m)

MS: 480(M+)

204: Colorless Crystal mp: 175°–175.5° C.

IR(KBr) cm⁻¹: 3400,2930,1609,1497,1446,797,743

¹HNMR(CDCl3) δ: 8.10(1H,brs),7.63(1H,d,J=8.1),7.39 (1H,s), 7.36(1H,d,J=8.4),7.28(1H,d,J=8.4),7.18(2H,m),7.10 (1H,m), 6.98(1H,d,J=2.2),4.24(2H,t,J=6.8),2.95(2H,m),2.81 (1H,m), 2.79(3H,s),2.48(3H,s),2.43(2H,t,J=6.8), 2.16(2H, quint,J=6.8),2.1–2.0(2H,m),1.76(2H,m)

MS: 426(M+)

205: Orange Crystal mp: 214°–216° C.

Elementary Analysis: as C25H27N6Cl.1/4H2O Calcd.: C;66.51,H;6.14,N;18.61,Cl;7.85 Found: C;66.75,H;6.22, N;18.46,Cl;7.87

IR(KBr) cm⁻¹: 3400,2940,1626,1603,1497,1444,1342, 1067,743

¹HNMR(CDCl3) δ: 8.11(1H,brs),7.65(1H,d,J=7.8),7.56 (1H,d, J=2.0),7.48(1H,d,J=7.8),7.37(1H,d,J=7.8),7.18(2H, m),7.10 (1H,t,J=7.8),7.00(1H,d,J=2.0),4.26(2H,t,J=6.4), 2.92(2H, m),2.83(1H,m),2.78(3H,s),2.37(2H,t,J=6.4),2.15 (2H,quint, J=6.2),2.11–2.00(4H,m),1.80–1.75(2H,m)

MS: 447(M+H)+

206: Colorless Crystal mp: 240°–243° C.

Elementary Analysis: as C32H31N5.H2O Calcd.: C;76.31,H;6.60,N;13.90 Found: C;76.52,H;6.37,N;13.79

IR(KBr) cm⁻¹: 3400,2950,1624,1593,1499,1477,1435, 803,748

¹HNMR(CDCl3) δ: 7.57(1H,d,J=7.9),7.38–7.30(6H,m), 7.24–7.16(5H,m),6.90(2H,s),4.23(2H,t,J=6.7),2.79(3H,s), 2.46(2H,m),2.33(4H,m),2.10(6H,m)

MS: 486(M+H)+

207: Colorless Crystal mp: 234°–235° C.

IR(KBr) cm⁻¹: 3400,2946,1624,1593,1499,1479,1435, 1381, 779,748

¹HNMR(CDCl3) δ: 7.58(1H,d,J=7.8),7.40(1H,dd,J=6.8, 1.0), 7.37(1H,td,J=7.3,1.0),7.20(1H,td,J=6.8,1.5),7.15–7.05 (8H,m),4.26(2H,t,J=6.6),3.39(2H,m),2.80(2H,m), 2.79(3H, s),2.58(2H,m),2.36(6H,m),2.13(4H,m)

MS: 488(M+H)+

Example 208

5-(3-methoxypropyl)-1H-[1,5]benzodiazepine-2,4(3H,5H)-dione (208)

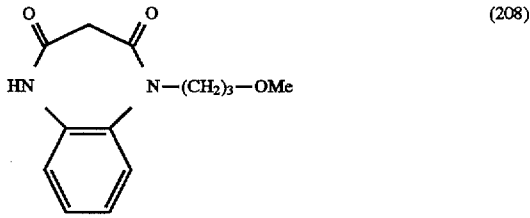

To a stirred mixture of 8 ml of malonyl dichloride and 90 ml of o-dichlorobenzene at 60° C., a solution containing 12.7 g of N-(3-methoxypropyl)-o-phenylenediamine in 10 ml of o-dichlorobenzene is added for 32 minutes in several times. The resulting mixture is stirred at 130° C. for 1.6 hours and then subjected to filtration during hot. The filtrate is concentrated and purified by silica gel column chromatography (ethyl acetate). n-hexane is added and precipitated crystals are separated by filtration and dried to obtain 9.8 g of (208).

mp: 137°–138° C.

IR(KBr) cm⁻¹: 1696,1676,1417,1243,748

¹HNMR(CDCl3) δ: 9.29(1H,s),7.41(1H,ABd,J=7.6,1.8), 7.29(1H, td,J=7.3,1.8),7.25(1H,td,J=7.3,1.8),4.33(1H,m), 3.80(1H,m), 3.36(1H,s),3.35(1H,s),3.33(1H,m),3.26(1H,m) ,3.19(3H,s), 1.87(1H,m),1.77(1H,m)

Example 209

5-(3-bromopropyl)-1H-[1,5]benzodiazepine-2,4(3H,5H)-dione (209)

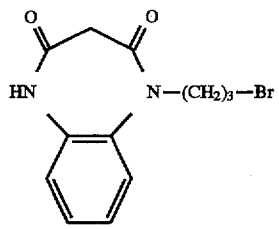

To 4.9 g of the compound of Example 208, 25 ml of 30% hydrobromic acid-acetic acid solution is added and the resulting mixture is stirred at 60° C. for 4.7 hours. The resulting mixture is poured into water and the resultant is subjected to extraction with ethyl acetate. The organic layer is washed with aqueous sodium carbonate solution and brine and dried. The resultant is purified by silica gel column chromatography (ethyl acetate) to obtain 3.3 g of (209).

mp: 154°–156° C.

IR(KBr) cm$^{-1}$: 1711,1661,1504,1415,1404,1278,754

1HNMR(CDCl3) δ: 8.96(1H,s),7.40–7.20(4H,m),4.31 (1H,brs), 3.92(1H,brs),3.36(2H,s),3.32(2H,m),2.19(2H,brs)

MS: 296(M+)

Example 210

5-[3-[4-[(4-chlorophenyl)phenylmethyl]piperazin-1-yl]propyl]-1H-[1,5]benzodiazepine-2,4(3H,5H)-dione (210)

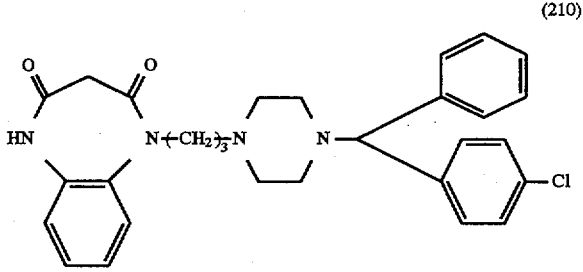

Twenty five milliliters of dimethylformamide is added to 2.3 g of the compound of Example 209, 2.6 g of 1-[(4-chlorophenyl)phenylmethyl]piperazine and 2.2g of potassium carbonate and the resulting mixture is stirred at 100° C. for 4 hours. To the mixture, 0.35 g of 1-[(4-chlorophenyl)phenylmethyl]piperazine is added and the resulting mixture is stirred at 100° C. for 2.5 hours. The precipitate is removed by filtration and the filtrate is condensed, followed by purification by silica gel column chromatography (ethyl acetate:methanol=9:1-8:1) to obtain 3.7 g of (210).

IR(KBr) cm$^{-1}$: 2814,1671,1502,1398,1091,1011,760

1HNMR(CDCl3) δ: 8.89(1H,s),7.39–7.31(5H,m), 7.27–7.11(8H, m),4.29(1H,brs),4.15(1H,s),3.70(1H,brs), 3.33(1H,s),3.31(1H,s),2.31(9H,brs),1.82(1H,brs),1.69(2H,brs)

MS: 502(M+)

Example 211

1-methyl-6-[3-[4-[(4-chlorophenyl)phenylmethyl]piperazin-1-yl]-propyl]-4H[1,2,4]triazolo[4,3-a][1,5]benzodiazepine-5(6H)-one (211)

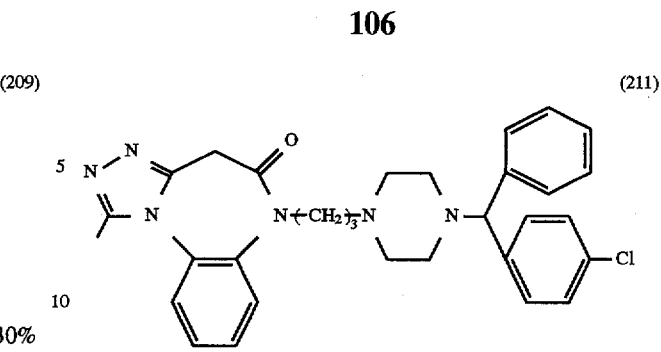

To 3.7 g of the compound of Example 210 and 1.7 g of phosphorus pentasulfide, 40 ml of pyridine is added and the resulting mixture is stirred at 100° C. for 3.1 hours. The solvent is evaporated and water and chloroform are added to carry out extraction. The organic layer is washed with water and dried. The residue is subjected to silica gel column chromatography (chloroform-2% methanol) to obtain 3.4 g of a mixture of 5-[3-[4-[(4-chlorophenyl)phenylmethyl] piperazin-1-yl]propyl]-2,3-dihydro-2-thioxo-1H-[1,5] benzodiazepin-4(5H)-one and 5-[3-[4-[(4-chlorophenyl) phenylmethyl]piperazin-1-yl]propyl]-1H-[1,5] benzodiazepine-2,4(3H,5H)-dithione. To this mixture, 40 ml of n-butanol is added and 1.7 g of acetohydrazide is added in five times while the mixture is heated to reflux. The resulting mixture is heated to reflux for another 15.8 hours. Water and ethyl acetate are added to carry out extraction and the organic layer is washed with water and dried, followed by purification by silica gel column chromatography (ethyl acetate:methanol=6:1-4.5:1) to obtain 2.2 g of (211).

IR(KBr) cm$^{-1}$: 2814,1682,1506,1427,1011,760

1HNMR(CDCl3) δ: 7.55(1H,AB,J=8.2,1.5),7.51(1H,td, J=7.0, 1.5),7.38–7.31(5H,m),7.27–7.21(4H,m),7.17(1H,t,J= 7.0), 4.30(1H,m),4.15(1H,s),4.08(1H,AB,J=14.0),3.61(1H, m), 3.36(1H,AB,J=14.3),2.60(3H,d,J=1.8),2.30(4H,brs), 2.26(4H,brs),2.10(1H,m),1.97(1H,m),1.64(1H,m),1.51 (1H,m)

MS: 540(M+)

Example 212

1-methyl-6-(3-methoxypropyl)-4H[1,2,4]triazolo[4,3-a][1,5]benzodiazepin-5(6H)-one (212)

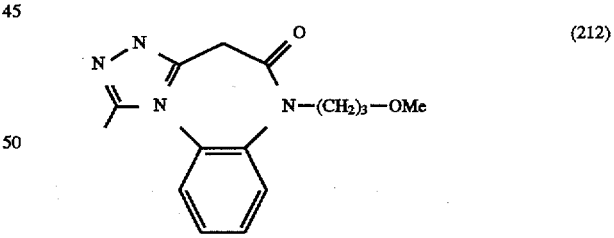

To a solution containing 1.59 g of triethyloxonium tetrafluoro borate in 30 ml of dichloromethane, 1.09 g of the compound of Example 208 is added and the resulting mixture is stirred overnight at room temperature. Aqueous sodium carbonate solution is added to the mixture and the organic layer is separated. The organic layer is condensed and purified by column chromatography to obtain 0.60 g of colorless oil. To this oil, 15 ml of n-BuOH and 0.25 g of acetohydrazide are added and the resulting mixture is heated to reflux for 12 hours. After evaporating the solvent, ether is added to crystallize the product to obtain 0.51 g of the captioned compound.

mp: 185°–190° C.

IR(KBr) cm⁻¹: 1665,1541,1510,1466,1433,1383,1120, 791

¹HNMR(CDCl3) δ: 7.6–7.2(4H,m),4.6–4.2(1H,m),4.09 (1H,ABq, J=14.3),3.9–3.4(1H,m),3.37(1H,ABq,J=14.3), 3.3–2.8(2H,m),3.10(3H,s),2.62(3H,s),1.9–1.5(2H,m)

MS: 286(M+)

Example 213

1-methyl-6-[3-[4-[(4-chlorophenyl)phenylmethyl] piperazin-1-yl]-propyl]-4H[1,2,4]triazolo[4,3-a][1,5] benzodiazepine-5(6H)-one (211)

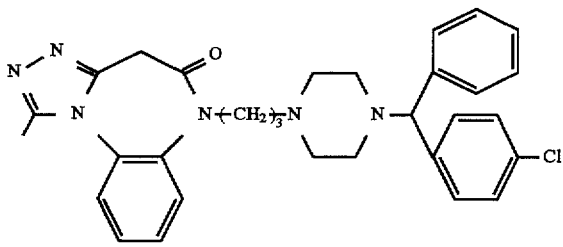
(211)

To 0.23 g of the compound of Example 212, 2 ml of 47% hydrobromic acid is added and the mixture is stirred at 110° C. for 1.5 hours. The solvent is evaporated under reduced pressure and the residue is dried. To the residue, 4 ml of dimethylformamide, 0.45 g of sodium carbonate and 0.29 g of 1-[(4-chlorophenyl)phenylmethyl]piperazine are added and the resulting mixture is stirred at 90° C. for 1.5 hours. The solvent is evaporated under reduced pressure and dichloromethane and water are added to the residue to carry out extraction. The organic layer is washed with water and dried. The solvent is evaporated and the residue is purified by silica gel column chromatography (ethyl acetate:methanol=3:2), followed by recrystallization from n-butanol to obtain 0.20 g of the captioned compound in the form of colorless crystals.

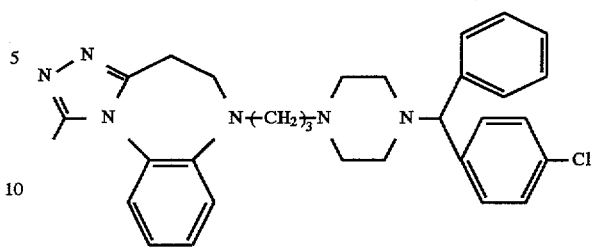
(213)

To 1.1 g of the compound of Example 211, 20 ml of tetrahydrofuran is added and then 0.17 g of lithium aluminum hydride is added. The resulting mixture is heated to reflux for 30 minutes. To the resultant, 0.82 g of lithium aluminum hydride is added and the mixture is heated to reflux for 20 minutes. To the resulting mixture, ethyl acetate and water are added and the precipitate is removed by filtration using Celite. The filtrate is condensed and purified by silica gel column chromatography (ethyl acetate:methanol=7:1-6:1) to obtain 0.30 g of (213).

IR(KBr) cm⁻¹: 2940,2814,1504,1152,1011,758

¹HNMR(CDCl3) δ: 7.39(1H,m),7.34–7.31(4H,m), 7.25–7.15(8H, m),4.17(1H,s),3.39(2H,brs),3.09(2H,brs), 2.90(2H,brs),2.47(3H,s),2.35(8H,brs),2.15(2H,t,J=7.3),1.59 (2H,quint,J=7.3)

MS: 526(M+)

Example 215

5,6-dihydro-1-methyl-6-[3-[4-[(4-chlorophenyl) phenylmethyl]piperazin-1-yl]propyl]-4H[1,2,4]triazolo[4,3-a][1,5]benzodiazepine fumaric acid salt (214)

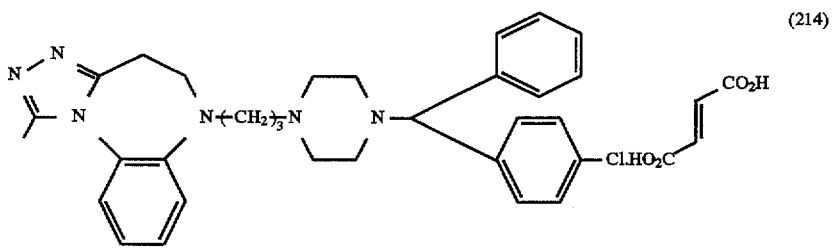
(214)

To a solution containing 0.26 g of the compound of Example 214 in methanol, 59 mg of fumaric acid in methanol is added and the resulting mixture is condensed. To the resultant, isopropanol and isopropyl ether are added. The resultant is subjected to filtration and the filtrate is dried to obtain 0.11 g of (214) in the form of amorphous.

Elementary Analysis: as C31H35N6Cl.C4H4O4 Calcd.: C,65.36;H,6.11;N,13.07; Cl,5.51 Found: C,65.58;H,6.34;N, 12.86; Cl,5.77

IR(KBr) cm⁻¹: 3390,1678,1504,984,762,648

Example 216

3-[4,5-dihydro-1-methyl-[1,2,4]triazolo[4,3-a]quinoxalin-5-yl methyl propionate

Example 214

5,6-dihydro-1-methyl-6-[3-[4-[(4-chlorophenyl) phenylmethyl]piperazin-1-yl]propyl]-4H[1,2,4]triazolo[4,3-a][1,5]benzodiazepine (213)

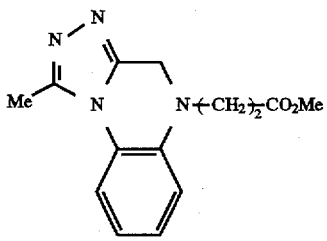

A solution containing 3.75 g of potassium t-butoxide in 10 ml of DMF is cooled to −18° C. and 3.13 g of the compound of Example 13 in 37 ml of DMF is added dropwise. Ten minutes later, the temperature is raised to room temperature and after another 40 minutes, the temperature is raised to 40° C. The mixture is stirred at this temperature for 90 minutes. Thereafter, 4.51 g of methyl 3-bromopropionate in 14 ml of DMF is added dropwise at −15° C. Fifteen minutes later, the temperature is again raised to 40° C. and the mixture is stirred for 5 hours. Saturated aqueous ammonium chloride solution is added while cooling the mixture in iced water to stop the reaction. The resulting mixture is subjected to extraction and the organic layer is washed and dried. The solvent is evaporated and the residue is purified by silica gel column chromatography to obtain 1.79 g of white crystals.

mp: 91°–94° C.

Elementary Analysis: as C14H16N4O2 Calcd.: C,61.75;H,5.92;N,20.58 Found: C,61.73;H,5.89;N,20.60

IR(KBr) cm$^{-1}$: 2958,1734,1504,1433,1261,1220,1195, 748

$^1$HNMR(CDCl3) δ: 8.03(1H,d,J=8.30),7.29(1H,t,J=7.81), 7.04–6.92(2H,m),4.51(2H,s),3.71(3H,s),3.71(2H,t,J=7.33), 2.86(3H,s),2.70(2H,t,J=7.33)

Example 217

3-[4,5-dihydro-1-methyl-[1,2,4]triazolo[4,3-a]quinoxalin-5-yl] propionic acid

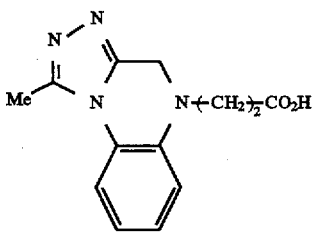

In 5 ml of ethanol, 245 mg of the compound of Example 216 is added and 1.35 ml of 1N aqueous potassium hydroxide solution is added dropwise while cooling the mixture in iced water, followed by stirring the mixture for 30 minutes. The resulting mixture is washed with chloroform and pH is adjusted to 4. The mixture is subjected to extraction with chloroform and the organic layer is dried. The solvent is evaporated and the residue is recrystallized from 2-propanol to obtain 159 mg of the captioned compound in the form of white crystals.

mp: 196°–197° C.

Elementary Analysis: as C13H14N4O2 Calcd.: C,60.45;H,5.46;N,21.69 Found: C,60.42;H,5.45;N,21.73

IR(KBr) cm$^{-1}$: 2838,2498,1700,1502,1435,1267,1207, 1015,750

$^1$HNMR(CDCl3) δ: 7.46(1H,dd,J=8.24,1.43),7.23(1H,dd, J=7.91, 1.76),7.05–6.80(2H,m),4.66(2H,s),3.75(2H,t,J= 6.38), 2.76(3H,s),2.72(2H,t,J=6.38)

Example 218

5-(3-bromopropyl)-4,5-dihydro-1-methyl[1,2,4]triazolo[4,3-a]quinoxaline

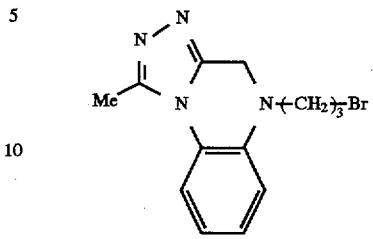

In 20 ml of anhydrous tetrahydrofuran, 1.51 g of the compound of Example 216 is dissolved and the solution is cooled to 0° C. To the resultant, 0.3 g of lithium aluminum hydride is added and the resulting mixture is stirred at room temperature for 3 hours. The mixture is again cooled to 0° C. and water is added. After stirring the mixture, the mixture is subjected to filtration using Celite. The solvent in the filtrate is evaporated and the residue is subjected to extraction with chloroform. The organic layer is condensed and subjected to purification by silica gel chromatography to obtain 0.86 g of colorless crystals. This product is dissolved in 15 ml of chloroform and the solution is cooled to 0° C. To this solution, 1 ml of thionyl bromide is added and the resulting mixture is stirred overnight at room temperature, followed by heating to reflux for 2 hours. Aqueous sodium carbonate solution is added and the organic layer is separated and dried. The solvent is evaporated and the residue is purified by column chromatography to obtain 0.25 g of the captioned compound in the form of colorless crystals.

IR(KBr) cm$^{-1}$: 1502,1431,750

$^1$HNMR(CDCl3) δ: 7.47(1H,m),7.18(1H,m),7.02–6.85 (2H,m), 4.44(2H,s),3.53(2H,t,J=7.0),3.49(2H,t,J=6.1),2.78 (3H,s), 2.23(2H,m)

MS: 306(M+)

The PAF-antagonizing action and antiallergic actions of the compounds represented by the formula (I) will now be described.

1. Test for Antiallergic Action (Rat PCA Reaction)

The antiallergic action was evaluated by passive cutaneous anaphylaxis (PCA) test using rats. The test was carried out using Wister male rats having body weights of 150–200 g.

Physiological saline containing anti-dinitrophenyl group (DNP) mouse IgE monoclonal antibody (commercially available from Seikagaku Kogyo Co., Ltd.) was intracutaneously injected in the skin of the back of each rat. Twenty three hours later, a suspension of the test compound in olive oil was orally administered at a dose of 50 mg/kg to each rat. One hour later, 0.5 ml of physiological saline containing 2 mg/ml of ovalbumin modified with dinitrophenyl hapten and 1% Evans blue were administered to each rat via femoral vein. Thirty minutes later, the rat was killed by cutting the carotid artery. The skin was peeled off and the portion stained in blue was cut out. The cut out portion was minced in formaldehyde and the pigment was extracted at 60° C. for 48 hours. The minced skin was removed by centrifugation (1500×g, 10 min.) and the absorbance at 620 nm of the supernatant was measured. Based on a preliminarily prepared calibration curve, the pigment leaked to the topical portion was quantified. As a control, olive oil alone was administered and the ratio of the amount of the pigment in test groups to the amount of the pigment in control group is expressed as inhibition rate. The results are shown in Table 1.

2. Histamine-Antagonizing Action

A suspension of a test compound in olive oil was orally administered at a dose of 50 mg/kg to each rat of the same kind as those used in 1. One hour later, physiological saline containing 1% Evans blue was intravenously administered at a dose of 3 ml/kg. Immediately thereafter, 50 μl of 900 μM histamine solution was intracutaneously administered to each rat. Thirty minutes later, the pigment in the blue-stained portion in the skin was extracted and quantified as mentioned above. Using the amount of the pigment when olive oil was administered as control, the inhibition rate which is the ratio of the amount of the pigment when the test compound was administered to the control was calculated. The results are shown in Table 1.

TABLE 1

| Compound No. | Inhibition Rate (%) Anti-PCA | Antihistamine |
| --- | --- | --- |
| 4 | 44 | 76 |
| 45 | 49 | 43 |
| 46 | 65 | 72 |
| 49 | 58 | 65 |
| 52 | 65 | 47 |
| 75 | 42 | 19 |
| 189 | 43 | 57 |
| 192 | 74 | 38 |
| 199 | 48 | 53 |
| 214 | 75 | 87 |

As is apparent from the above-described test results, the compounds represented by the formula (I) and salts thereof have excellent antihistamine property and antiallergic property.

3. in vitro Platelet Agglutination Inhibition Test

To determine the PAF-antagonizing property of the compounds, the PAF-induced agglutination of rabbit platelets in vitro is utilized. To obtain platelet-rich plasma (PRP), venous blood is taken from rabbit auricular vein into a plastic centrifugal tube containing 1.0% sodium citrate solution. The ratio of sodium citrate solution to blood is 1:10. The obtained citrate-containing blood is centrifuged at 70×g (625 rpm) at room temperature for 20 minutes and the PRP in the upper layer is transferred to another plastic tube. The remaining lower layer is further centrifuged at 1500×g (2800 rpm) for 10 minutes and the platelet poor plasma (PPP) in the upper layer is recovered. The platelet agglutination is measured by using aggregometer commercially available from Niko Bioscience, Inc. An aliquote of the PRP is poured into a cubette for measurement. Immediately thereafter, aspirin, creatinin phosphate and creatinin phosphokinase are added to final concentrations of 0.1 mM, 7 mM and 45 U/ml, respectively. Then a solution of a test compound is added and the resulting mixture is stirred at 37° C. for 2 minutes. To the resultant, PAF (final concentration: 10 ng/ml) is added to induce platelet aggregation. The platelet aggregation rate is calculated from the relative maximum value in each aggregation curve taking the transmittance of PPP as the maximum aggregation (100% aggregation). Using the aggregation rate when physiological saline was added as a control, the inhibition rate which was the ratio of the aggregation rate when the test compound was added to the control was calculated and the IC50 values were determined by interpolation.

The results are shown in Table 2.

TABLE 2

| Compound No. | PAF-Induced Platelet Aggregation IC50 (μg/ml) | Compound No. | PAF-Induced Platelet Aggregation IC50 (μg/ml) |
| --- | --- | --- | --- |
| 4 | 2.0 | 52 | 5.4 |
| 53 | 1.8 | 63 | 4.4 |
| 64 | 1.6 | 65 | 2.0 |
| 66 | 1.9 | 73 | 4.5 |
| 75 | 0.21 | 77 | 0.072 |
| 78 | 2.4 | 80 | 0.044 |
| 81 | 0.68 | 85 | 1.4 |
| 86 | 2.2 | 87 | 3.1 |
| 88 | 0.86 | 90 | 0.56 |
| 92 | 0.66 | 127 | 0.23 |
| 128 | 1.7 | 129 | 0.17 |
| 130 | 0.32 | 131 | 0.13 |
| 132 | 0.036 | 133 | 0.063 |
| 134 | 0.051 | 135 | 0.88 |
| 138 | 0.81 | 140 | 0.24 |
| 142 | 0.51 | 143 | 0.22 |
| 145 | 0.91 | 147 | 0.087 |
| 148 | 0.32 | 149 | 0.55 |
| 150 | 0.51 | 151 | 0.76 |
| 154 | 0.19 | 155 | 1.2 |
| 156 | 0.58 | 160 | 0.071 |
| 161 | 0.54 | 163 | 0.32 |
| 164 | 0.36 | 165 | 0.74 |
| 189 | 0.31 | 193 | 0.84 |
| 194 | 0.045 | 195 | 0.14 |
| 196 | 0.013 | 197 | 0.025 |
| 198 | 0.074 | 199 | 0.12 |
| 200 | 0.023 | 201 | 0.16 |
| 205 | 2.3 | 206 | 2.1 |
| 214 | 4.0 | | |

As is apparent from the above-described test results, the compounds of the formula (I) and salts thereof have excellent PAF-antagonizing property.

4. Binding Test Using [$^3$H]-PAF (PAF receptor binding test)

Cell membrane fraction of rabbit platelets was prepared in accordance with the method by Hwang et al (Biochemistry; 22; 4756, (1983)). In 10 mM Tris buffer containing 0.25% bovine serum albumin, 50 mg of this membrane fraction was suspended and tritium-labelled PAF [$^3$H]-PAF; 0.4 nM) and a test compound were added thereto. After incubating the resulting mixture at 25° C. for 60 minutes, the mixture was subjected to filtration through a filter paper made of glass fibers. The filter paper was washed with cold Tris buffer three times and then transferred to a vial. A scintillator was added thereto and the dose of radioactivity was measured with a liquid scintillation counter. The inhibition rate (binding ability) of the test compound was calculated according to the following equation and IC50 values were determined by interpolation.

$$\text{Inhibition Rate (\%)} = \left\{ 1 - \left[ \frac{(A-B)}{(C-B)} \right] \right\} \times 100$$

(wherein A represents amount bound in the presence of the compound, B represents amount bound by non-specific binding which is the dose of [$^3$H]-PAF bound radioactivity in the presence of 1 μM of PAF, and C represents total amount bound which is the dose of [$^3$H]-PAF bound radioactivity.

The results are shown in Table 3. As a control agent, WEB2086 (Japanese Laid-open Patent Application (Kokai) No. 65-176591) disclosed as a PAF-antagonist was used.

TABLE 3

| Compound No. | Receptor Binding Inhibition IC50 (µg/ml) | Compound No. | Receptor Binding Inhibition IC50 (µg/ml) |
| --- | --- | --- | --- |
| 4 | 1.0 | 43 | 3.0 |
| 44 | 0.80 | 45 | 0.32 |
| 46 | 0.18 | 49 | 1.7 |
| 52 | 3.5 | 53 | 1.5 |
| 54 | 0.5 | 55 | 0.37 |
| 56 | 0.48 | 57 | 1.2 |
| 58 | 0.28 | 64 | 0.46 |
| 65 | 4.8 | 69 | 0.36 |
| 72 | 1.9 | 73 | 3.1 |
| 74 | 0.23 | 75 | 0.41 |
| 77 | 0.097 | 76 | 0.13 |
| 78 | 0.059 | 80 | 0.33 |
| 81 | 1.5 | 85 | 0.11 |
| 86 | 3.00 | 87 | 0.10 |
| 88 | 0.34 | 90 | 0.99 |
| 127 | 0.077 | 128 | 0.63 |
| 129 | 0.17 | 130 | 0.070 |
| 131 | 0.045 | 132 | 0.026 |
| 133 | 0.017 | 134 | 0.005 |
| 135 | 0.021 | 138 | 0.72 |
| 140 | 0.006 | 142 | 0.087 |
| 143 | 0.040 | 145 | 0.22 |
| 147 | 0.034 | 148 | 0.029 |
| 149 | 0.105 | 150 | 0.083 |
| 151 | 0.060 | 154 | 0.091 |
| 155 | 0.072 | 156 | 0.029 |
| 160 | 0.097 | 161 | 0.16 |
| 163 | 0.18 | 164 | 0.12 |
| 165 | 0.40 | 189 | 0.14 |
| 191 | 3.2 | 192 | 0.69 |
| 193 | 2.9 | 194 | 1.1 |
| 195 | 0.11 | 196 | 0.24 |
| 197 | 0.032 | 198 | 0.21 |
| 199 | 0.035 | 200 | 0.03 |
| 201 | 0.17 | 205 | 1.3 |
| 206 | 0.88 | WEB 2086 | 0.05 |

As is apparent from the above-described test results, the compounds represented by the formula (I) and salts thereof have excellent PAF receptor-antagonizing property.

5. PAF-induced Bronchial Hyperresponsiveness Model in Guinea Pigs

The test was carried out using Hartley male guinea pigs having body weights of 300–400 g.

A) Evaluation of Bronchial Responsiveness

Guinea pigs were retained on body plethysmo boxes without anesthesia and the respiratory resistances (Rrs) were determined by osscilation method. Each animal with which the Rrs was being continuously measured was made to inhale aerosol of acetylcholine (Ach) solutions with serially increased concentrations by 2-fold from 31 µg/ml to 4000 µg/ml such that the animal was made to aspirate the aerosol with each concentration for 1 minute each. The Ach threshold value which is required for the Rrs to reach 1.5 cm $H_2O$/ml/sec was determined. The baseline of Rrs was 0.2–0.5 cm $H_2O$/ml/sec. The Ach threshold value means the value calculated taking the value when a guinea pig is made to inhale 1000 ug/ml of Ach aerosol for 1 minute as 1 unit. The above-described operation was carried out using Animal Ast (registered trademark) commercially available from Chest M. I. Co., Ltd.

b) Induction and Evaluation of Bronchial Hyperresponsiveness

By the method of A), the bronchial responsiveness of guinea pigs, that is, the Ach threshold values were determined. Subsequently, each animal was made to inhale aerosol of 100 µg/ml of PAF solution for 10 minutes. Forty minutes after the completion of the inhalation, the bronchial responsiveness was again measured by the method of A). The bronchial hyperresponsiveness was detected based on the ratio between the Ach threshold value before and after the inhalation of PAF (Ach respiration threshold value after inhalation of PAF/Ach respiration threshold value before inhalation of Ach; Post/Pre value). That is, if the bronchial hyperresponsiveness is strongly promoted, the Post/Pre value is lower than 1.0, and if it is not promoted, the Post/Pre value is about 1.0. A suspension of a test compound in olive oil was orally administered to each guinea pig and the determined Post/Pre value was compared with that of the control group to which olive oil was administered to evaluate the inhibition effect. The results are shown in Table 4. As a control agent, WEB 2086 disclosed as a PAF-antagonist was used.

TABLE 4

| Compound No. | Dose (mg/kg) | Post/Pre |
| --- | --- | --- |
| Control | | 0.57 |
| 46 | 0.3 | 1.64 |
| 46 | 0.1 | 1.14 |
| 52 | 1 | 1.37 |
| 73 | 1 | 1.18 |
| 192 | 1 | 1.81 |
| WEB 2086 | 3 | 0.89 |

As is apparent from the above-described results, the compounds represented by the formula (I) have excellent pAF-antagonizing property and have effect to inhibit bronchial hyperresponsiveness.

We claim:

1. A tricyclic triazolo derivative of the formula (I):

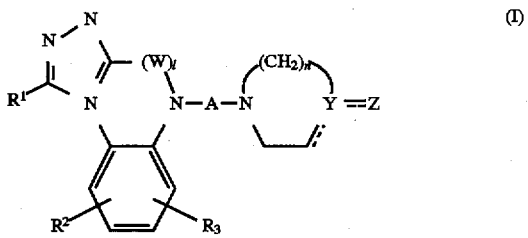

wherein $R^1$ represents hydrogen, lower alkyl or $C_3$-$C_5$ cycloalkyl; $R^2$ and $R^3$ respectively represent hydrogen, lower alkyl, lower alkoxy or halogen; W represents C=O or $CR^4R^5$, wherein $R^4$ and $R^5$ respectively represent hydrogen or lower alkyl; A represents $C_1$-$C_5$ straight or branched chain (i) alkylene, which may be substituted with an OH group or which may contain one oxygen atom forming an ether having the formula $-(CH_2)_a-O-(CH_2)_b-$ wherein a and b are each 1 to 4 and wherein the sum of a and b is up to 5, (ii) alkenylene, or (iii) alkynylene group; 1 represents 1, n represents 1 to 3, $=\!\!\!=$ represents single bond or double bond; Y represents N or C; Z represents $C(B)Ar^1Ar^2$ (wherein B represents hydrogen, hydroxy or methoxy, $Ar^1$ and $Ar^2$ respectively represent hydrogen or aryl which may be substituted with 1–3 substituent groups selected from the group consisting of $C_1$-$C_6$ alkyl, $C_1$-$C_6$ alkoxy, alkylcarbonyl, alkylsulfonyl, halogen, haloalkyl, alkylamino, nitro, cyano, hydroxy, mercapto and alkylthio), $CAr^1Ar^2$ (wherein $Ar^1$ and $Ar^2$ represent the same meanings as mentioned above), O—$CHAr^1Ar^2$ (wherein $Ar^1$ and $Ar^2$ represent the same meanings as mentioned above) or phenyl, naphthyl, quinolyl, benzimidazolyl, benzofuranyl, benzothiophenyl, benzisoxazolyl, benzthiazolyl, imidazopyridinyl, or a group selected from the group consisting of

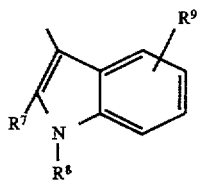

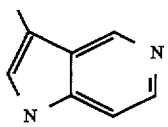

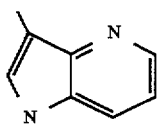

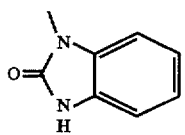

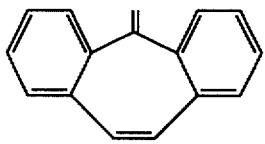

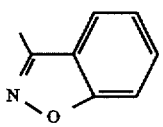

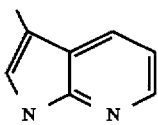

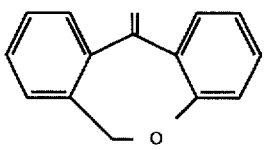

and

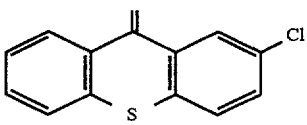

wherein $R^7$ and $R^8$ respectively represent hydrogen or lower alkyl, $R^9$ represents hydrogen, lower alkyl, lower alkoxy or halogen; ≡ represents single bond or double bond); and pharmaceutically acceptable salts thereof.

2. The tricyclic triazolo derivative of claim 1 which is represented by the formula (Ia):

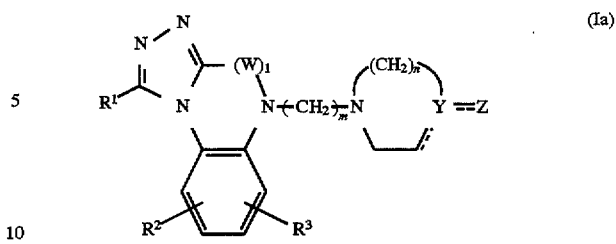

(Ia)

(wherein $R^1$, $R^2$, $R^3$, 1, n, Y, ≡ and Z represent the same meanings as mentioned above, and m represents an integer of 1 to 4)
and pharmaceutically acceptable salts thereof.

3. A tricyclic triazolo derivative of the formula (I):

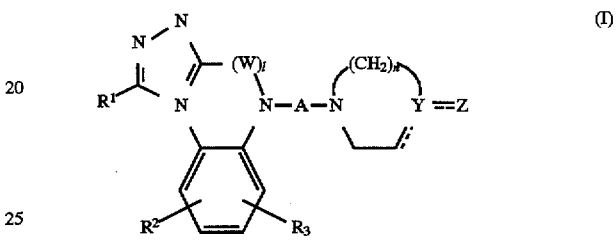

(I)

wherein $R^1$ represents hydrogen, lower alkyl or $C_3$–$C_5$ cycloalkyl; $R^2$ and $R^3$ each independently represent hydrogen, lower alkyl, lower alkoxy or halogen; W represents C=O or $CR^4R^5$, wherein $R^4$ and $R^5$ each independently represent hydrogen or lower alkyl; A represents $C_1$–$C_5$ straight or branched chain (i) alkylene which may be substituted with an OH group or which may contain one oxygen atom forming an ether having the formula –(CH$_2$)$_a$– O–(CH$_2$)$_b$– wherein a and b are each 1 to 4 and wherein the sum of a and b is up to 5, (ii) alkenylene, or (iii) alkynylene group; l represents 1, n represents 1 to 3, ≡ represents single bond or double bond; Y represent N or C; Z represents C(B)Ar$^1$Ar$^2$, CAr$^1$Ar$^2$, O-CHAr$^1$Ar$^2$, phenyl, naphthyl quinolyl, benzimidazolyl, benzofuranyl, benzothiophenyl, benzisoxazolyl, benzthiazolyl, imidazopyridinyl, or a group selected from the group consisting of

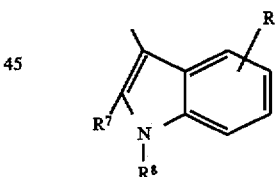

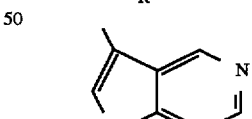

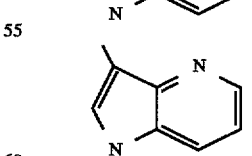

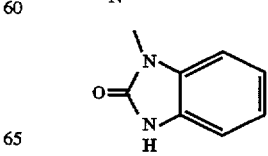

-continued

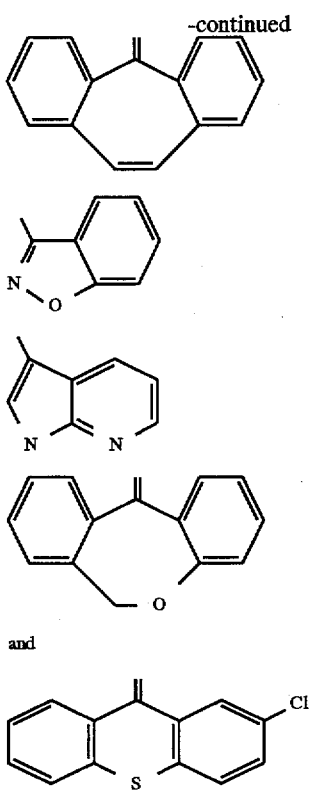

and wherein B represents hydrogen, hydroxy or methoxy, $Ar^1$ and $Ar^2$ are each independently hydrogen or a substituted or unsubstituted aryl group, wherein said substituted aryl group contains from 1 to 3 substituents, each selected from the group consisting of $C_1$–$C_6$ alkyl, $C_1$–$C_6$ alkoxy, alkylcarbonyl, alkylsulfonyl, halogen, halogenated alkyl, alkylamine, nitro, cyano, hydroxy, mercapto, and alkylthio; $R^7$ and $R^8$ respectively represent hydrogen or lower alkyl, $R^9$ represents hydrogen, lower alkyl, lower alkoxy or halogen; = represents a single bond or double bond; and pharmaceutically acceptable salts thereof.

4. A dihydrotriazolo quinoxaline derivative of the formula (II):

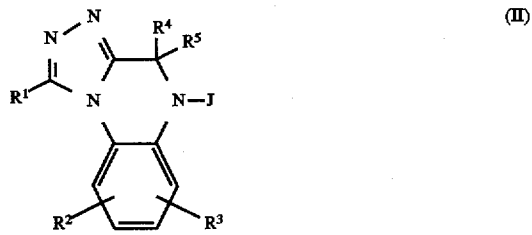

wherein $R^1$ represents hydrogen, lower alkyl, or $C_3$–$C_5$ cycloalkyl; $R^2$ and $R^3$ each independently represent hydrogen, lower alkyl, lower alkoxy, or halogen; $R^4$ and $R^5$ each independently represent hydrogen or lower alkyl; J represents hydrogen, -A-B wherein A represents $C_1$–$C_5$ straight or branched chain (i) alkylene, which may be substituted with an OH group or which may contain one oxygen atom forming an ether having the formula –(CH$_2$)$_a$–O–(CH$_2$)$_b$– wherein a and b are each 1 to 4 and wherein the sum of a and b is up to 5, (ii) alkenylene, or (iii) alkynylene group, and B represents halogen, —OR$^{10}$ wherein R$^{10}$ represents a protective group for alcohol, or -A' —CO$_2$L wherein L represents hydrogen or lower alkyl and A' represents a $C_1$–$C_4$ straight or branched chain alkylene.

5. The derivative according to claim 1, wherein said pharmaceutically acceptable salts are acid salts.

6. A process for producing the triazolo derivative of formula (I) as claimed in claim 1, comprising the step of reacting a compound of the formula (V):

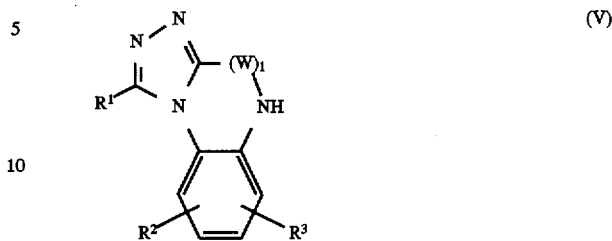

wherein $R^1$, $R^2$, $R^3$, and 1 represent the same meanings as mentioned above and W is $CR^4R^5$,
with a compound of the formula (VI):

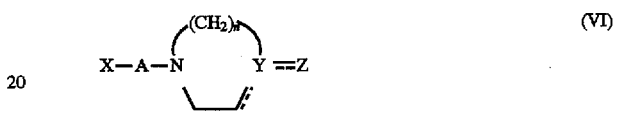

wherein X represents halogen, and A, Y, Z, n and = represent the same meanings as mentioned above, in the presence of an inorganic base selected from the group consisting of sodium hydride, sodium hydride/potassium hydride mixture, calcium hydride, sodium amide and potassium hydroxide, or an organic base.

7. The derivative according to claim 1, wherein $Ar^1$ and $Ar^2$ are selected from the group consisting of phenyl, napthyl, furyl, thienyl, pryidyl, pyrimidinyl, oxazolyl, isoxazolyl, thiazolyl, isothiaolyl, imidazolyl, pyrazolyl, and beuzofuranyl.

8. The process according to claim 6, wherein said inorganic base is a sodium hydride/potassium hydride mixture.

9. The derivative according to claim 4, wherein $R^{10}$ is selected from the group consisting of methyl, ethyl, isopropyl, benzyl, tetrahydropyranyl, methoxymethyl, and methylthiomethyl.

10. The process according to claim 6, wherein said reaction is carried out in the presence of said organic base.

11. The process according to claim 10, wherein said organic base is selected from the group consisting of pyridine, triethylamine, and potassium t-butoxide.

12. An anti-inflammation composition comprising an effective amount of the derivative according to claim 1 or a pharmaceutically acceptable salt thereof and a pharmaceutically acceptable carrier.

13. An anti-allergy composition comprising an effective amount of the derivative according to claim 1 or a pharmaceutically acceptable salt thereof, and a pharmaceutically acceptable carrier.

14. An anti-PAF composition comprising an effective amount of the derivative according to claim 1 or a pharmaceutically acceptable salt thereof, and a pharmaceutically acceptable carrier.

15. The process according to claim 11, wherein said organic base is potassium t-butoxide.

16. The tricyclic triazolo derivative and pharmaceutically acceptable salts thereof according to claim 1, wherein said A in formula (I) represents methylene, ethylene, trimethylene, tetramethylene, pentamethylene, methylethylene, ethylethylene, methyltrimethylene, ethyltrimethylene, methyltetramethylene or a group selected from the group consisting of

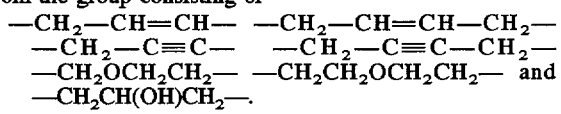

* * * * *